United States Patent [19]
Landes et al.

[11] Patent Number: 6,028,173
[45] Date of Patent: Feb. 22, 2000

[54] HUMAN CHROMOSOME 16 GENES, COMPOSITIONS, METHODS OF MAKING AND USING SAME

[75] Inventors: Gregory Landes; Timothy Burn, both of Northborough; Timothy Connors; William Dackowski, both of Hopkinton; Terence Van Raay, Hudson; Katherine Klinger, Sudbury, all of Mass.

[73] Assignee: Genzyme Corporation, Framingham, Mass.

[21] Appl. No.: 08/665,259

[22] Filed: Jun. 17, 1996

Related U.S. Application Data

[60] Provisional application No. 60/000,596, Jun. 30, 1995.

[51] Int. Cl.$^7$ .............................. C07K 1/00; C07K 14/00; C07K 17/00; A61K 38/00
[52] U.S. Cl. .......................... 530/350; 530/300; 530/325; 530/364
[58] Field of Search .............................................. 530/350

[56] References Cited

U.S. PATENT DOCUMENTS

| | | |
|---|---|---|
| 4,675,285 | 6/1987 | Clark et al. . |
| 5,252,475 | 10/1993 | Reth . |
| 5,550,037 | 8/1996 | Francavilla et al. . |
| 5,565,331 | 10/1996 | Tessier-Lavigne et al. . |

FOREIGN PATENT DOCUMENTS

| | | |
|---|---|---|
| 0 668 291 A2 | 8/1995 | European Pat. Off. . |
| 40 21 458 | 8/1991 | Germany . |
| WO 92/13071 | 8/1992 | WIPO . |
| WO 95/13367 | 5/1995 | WIPO . |
| WO 97/02346 | 1/1997 | WIPO . |

OTHER PUBLICATIONS

Genbank Accession No. AA048205.
Genbank Accession No. B54665.
Genbank Accession No. L37368.
Genbank Accession No. L48734.
Genbank Accession No. L48738.
Genbank Accession No. L48741.
Genbank Accession No. L48747.
Genbank Accession No. L48753.
Genbank Accession No. L48757.
Genbank Accession No. L48758.
Genbank Accession No. L48759.
Genbank Accession No. L48760.
Genbank Accession No. L48770.
Genbank Accession No. L48771.
Genbank Accession No. L48792.
Genbank Accession No. L75916.
Genbank Accession No. L75917.
Genbank Accession No. L75924.
Genbank Accession No. L75925.
Genbank Accession No. L75926.
Genbank Accession No. L75927.
Genbank Accession No. P15880.
Genbank Accession No. P25566.
Genbank Accession No. P34436.
Genbank Accession No. P34480.
Genbank Accession No. P41233.
Genbank Accession No. P41234.
Genbank Accession No. S34195.
Genbank Accession No. S41688.
Genbank Accession No. U18771.
Genbank Accession No. U65581.
Genbank Accession No. X73460.
Genbank Accession No. Z48149.
Giorda et al. Analysis of the structure and expression of the augmenter of liver regeneration (ALR) gene *Molecular Medicine* 2(1):97–108 (1996).
Luciani et al., "Cloning of two novel ABC transporters mapping on human chromosome 9" *Genomics* 21:150–159 (1994).
Rudinger, J., "Characteristics of the amino acids as components of a peptide hormone sequence" in: Peptide Hormones, J.A. Parsons, Ed., Univeristy Park Press, Baltimore, MD, pp. 1–7 (1976).
Sambrook et al., in: Molecular Cloning, A Laboratory Manual, 2nd Ed., Cold Spring Harbor Laboratory Press, pp. 10.27–10.28, 16.3–16.4, 17.2 (1989).
Baker et al. (1982) in "The Study of Biology" Addison–Wesley Publishing Company, Reading, MA (p. 9).
Houdebine (1994) "Production of pharmaceutical proteins from transgenic animals" *J. Biotech.* 34:269–87.
Altschul et al. "Basic local alignment search tool" *J. Mol. Biol.* (1990) 215:403–10.
The American PKD1 Consortium "Analysis of the genomic sequence for the autosomal dominant polycystic kidney disease (PKD1) gene predicts the presence of a leucine–rich repeat" *Hum. Mol. Genet.* (1995) 4(4):575–82.
Baskaran et al. "Uniform amplification of a mixture of deoxyribonucleic acids with varying GC content" *Genome Research* (1996) 6:633–38.
Brown et al. "Physical mapping, cloning, and identification of genes within a 500–kb region containing BRCA1" *PNAS USA* (1995) 92:4362–6.
Burn et al. "Increased exon–trapping efficiency through modifications to the pSPL3 splicing vector" *Gene* (1995) 161(2):183–7.
Carter et al. "Cloning and characterization of the mouse cytochrome c oxidase subunit IV gene" *Arch. Biochem. Biophys.* (1991) 288(1):97–106.
Church et al. "Identification of human chromosome 9 specific genes using exon amplification" *Hum. Mol. Genet.* (1993) 2(11):1915–20.
Church et al. "Isolation of genes from complex sources of mammalian genomic DNA using exon amplification" *Nature Genet.* (1994) 6:98–105.

(List continued on next page.)

*Primary Examiner*—Nita Minnifield
*Attorney, Agent, or Firm*—Antoinette F. Konski; Baker & McKenzie

[57] ABSTRACT

This invention provides an isolated human netrin polypeptide. Netrins define a family of diffusable factors involved in axon outgrowth.

6 Claims, 29 Drawing Sheets

OTHER PUBLICATIONS

Colamarino et al. "The axonal chemoattractant netrin–1 is also a chemorepellent for trochlear motor axons" *Cell* (1995) 81:621–9.

Dodd et al. "Axon guidance: A compelling case for repelling growth clones" *Cell* (1995) 81:471–4.

Duyao et al. "A gene from chromosome 4p16.3 with similarity to a superfamily of transporter proteins" *Hum. Mol. Genet.* (1993) 2(6):673–6.

Duyk et al. "Exon trapping: a genetic screen to identify candidate transcribed sequences in cloned mammalian genomic DNA" *PNAS USA* (1990) 87:8995–9.

The European Chromosome 16 Tuberous Sclerosis Consortium "Identification and characterization of the tuberous sclerosis gene on chromosome 16" *Cell* (1993) 75:1305–15.

The European Polycystic Kidney Disease Consortium "The polycystic kidney disease 1 gene encodes a 14 kb transcript and lies within a duplicate region on chromosome 16" *Cell* (1994) 77:881–94.

Gärtner et al. "Mutations in the 70K peroxisomal membrane protein gene in Zellweger syndrome" *Nature Genet.* (1992) 1:16–23.

Germino et al. "Positional cloning approach to the dominant polycystic kidney disease gene, PKD1" *Kidney Int.* (1993) 43(Supp 39):S20–S25.

Gottesman et al. "Biochemistry of multidrug resistance mediated by the multidrug transporter" *Ann. Rev. Biochem.* (1993) 62:385–427.

Graack et al. "YmL9, a nucleus–encoded mitochondrial ribosomal protein of yeast, is homologous to L3 ribosomal proteins from all natural kingdoms and photosynthetic organelles" *Eur. J. Biochem.* (1992) 206:373–80.

Harris et al. "A long–range restriction map between the α–globin complex and a marker closely linked to the polycystic kidney disease 1 (PKD1) locus" *Genomics* (1990) 7:195–206.

Harris et al. "Guidance cues at the drosophila CNS midline: identification and characterization of two drosophila netrin/UNC–6 homologs" *Neuron* (1996) 17:217–28.

Hedgecock et al. "The unc–5, unc–6, and unc–40 gene guide circumferential migrations of pioneer axons and mesodermal cells on the epidermis in c. elegans" *Neuron* (1990) 2:61–85.

Higgins "ABC transporters: from microorganisms to man" *Annu. Rev. Cell. Biol.* (1992) 8:67–113.

Higgins "The ABC of channel regulation" *Cell* (1995) 82:693–6.

The Huntington's Disease Collaborative Research Group "A novel gene containing a trinucleotide repeat that is expanded and unstable on Huntington's Disease chromosomes" *Cell* (1993) 72:971–83.

Kamijo et al. "The 70–kDa peroxisomal membrane protein is a member of the Mdr (P–glycoprotein)–related ATP–binding protein superfamily" *J. Biol. Chem.* (1990) 265(8):4534–40.

Kelly et al. "Assembly and function of the two ABC transporter proteins encoded in the human major histocompatibility complex" *Nature* (1992) 355–641–4.

Kennedy et al. "Netrins are diffusible chemotropic factors for commissural axons in the embryonic spinal cord" *Cell* (1994) 78:425–35.

Kerem et al. "Identification of the cystic fibrosis gene: genetic analysis" *Science* (1989) 245:1073–80.

Kerppola et al. "The membrane–bound proteins of periplasmic permeases form a complex" *J. Biol. Chem.* (1991) 266(15):9857–65.

Korenberg et al. "Human genome organization: Alu, lines and the molecular structure of metaphase chromosome bands" *Cell* (1988) 53:391–400.

Kuwano and Wool "The primary structure of rat ribosomal protein L3" *Biochem. Biophys. Res. Comm.* (1992) 187(1):58–64.

Liu et al. "Large–scale cloning of human chromosome 2–specific yeast artificial chromosomes (YACs) using an interspersed repetitive sequences (IRS)–PCR approach" *Genomics* (1995) 26:178–91.

Luciani et al. "The ATP binding cassette transporter ABC1, is required for the engulfment of corpses generated by apoptotic cell death" *EMBO J.* (1996) 15(2)226–35.

Mimmack et al. "Energy coupling to periplasmic binding protein–dependent transport systems: stoichiometry of ATP hydrolysis during transport in vivo" *PNAS USA* (1989) 86:8257–61.

Mitchell et al. "Genetic analysis of netrin genes in drosophila: netrins guide CNS commissural axons and peripheral motor axons" *Neuron* (1996) 17:203–15.

Mosser et al. "Putative X–linked adrenoleukodystrophy gene shares unexpected homology with ABC transporters" *Nature* (1993) 361:726–30.

Okumura et al. "In situ hybridization mapping of the hu man chromosome 16: evidence for a high frequency of repetitive DNA sequences" *Cytogenet. Cell Genet.* (1994) 67:61–7.

Ouellette et al. "Drug resistance and p–glycoprotein gene amplification in the protozoan parasite Leishmania" *Res. Microbiol.* (1991) 142–737–46.

Parimoo et al. "cDNA selection and other approaches in positional cloning" *Anal. Biochem.* (1995) 228–1–17.

Payne et al. "A mutational hot–spot in the hisM gene of the histidine transport operon in *Salmonella typhimurium* is due to deletion of repeated sequences and results in an altered specificity of transport" *Mol. Gen. Genet.* (1985) 200:493–6.

Peckham et al. "Retrovirus activation in embryonal carcinoma cells by cellular promoters" *Genes Dev.* (1989) 3:2062–71.

Plumbridge "Sequence of the nagBACD operon in *Escherichia coli* K12 and pattern of transcription within the nag regulon" *Mol. Microbiol.* (1989) 3(4):505–15.

Reeves et al. "An improved assay for the determination of Huntington's Disease allele size" *Am. J. Hum. Genet.* (1994) 55:A238 (Abstract only).

Rich et al. "Effect of deleting the R domain on CFTR–generated chloride channels" *Science* (1991) 253:205–7.

Riley et al. "A novel, rapid method for the isolation of terminal sequences from yeast artificial chromosome (YAC) clones" *Nuc. Acids Res.* (1990) 18(10):2887–90.

Saccone et al. "The highest gene concentrations in the human genome are in telomeric bands of metaphase chromosomes" *PNAS USA* (1992) 89:4913–17.

Schulze & Nierhaus "Minimal set of ribosomal components for reconstruction of the peptidyltransferase activity" *EMBO J.* (1982) 1(5):609–13.

Serafini et al. "The netrins define a family of axon outgrowth–promoting proteins homologous to C. elegans UNC–6" *Cell* (1994) 78:409–24.

Shepherd et al. "Preparation and screening of an arrayed human genomic library generated with the P1 cloning system" *PNAS USA* (1994) 91:2629–33.

Shustik et al. "Analysis of multidrug resistance (MDR–1) gene expression in chronic lymphocytic leukaemia (CLL)" *Br. J. Haematol.* (1991) 79:50–6.

Simonic et al. "cDNA sequence for bovine riobosomal protein L3 carrying a bipartite nuclear targeting motif, identified also in many other ribosomal proteins" *Biochem. Biophys. Acta* (1994) 1219–706–10.

Singer "The structure and insertion of integral proteins in membranes" *Annu. Rev. Cell Biol.* (1990) 6:247–96.

International Search Report for PCT/US96/10469.

International Search Report for PCT/US97/00785.

George et al. "Current Methods in Sequence Comparison and Analysis" in *Macromolecular Sequencing and Synthesis*, D. Schlesinger, (ed), Alan R. Liss, Inc, NY (1988) pp. 127–149.

Watson "Molecular Biology of the Gene" $3^{rd}$ Edition (1987) The Benjamin/Cummings Publishing Company, Inc. USA p. 608.

L48741

| | | |
|---|---|---|
| Exon Trap | | LHLEGPFISREKRGIHPEAHLRSFEADAFQDLLATYGPLINVRIVTLDPELGRSHEVFRILTXRSICVSLGHSVADLRAAEDAVWSGATF |
| C. elegans | 150 | -HLEGPFIS--KRG-HPE----S---------YG---N-IVT--PEL--E---------VS-GHS-A-L---E-AV-SGA-- |
| E. coli | 128 | LHLEGP------K-GIH------R--A-A--D-L------D----VTL-PE----EV--L----I-VS-GHS-A-L--A----G-TF |
| H. influenza | 126 | LH-E-P--S-EK-G-H----R---------D-L---G-D------T--E---------I-VS-GHS-A--A--A----GATF |

| | | |
|---|---|---|
| Exon Trap | | ITHLFNAMLPFHHRDPGIVGLLTSDRLPAGRCIFYGMIADGIHINPAALRIAHRAHPQGLVLVIDAIPALGLGNGRHILGQQEVEVDGLT |
| C. elegans | 242 | ITHLFNAM---HHRDPG--GLLTS--L-------YG-I-DG-HT---ALRLA-----GLVLVIDAI-ALG---G-H-LG-Q---V-GL- |
| E. coli | 213 | -THL-NAM-P-------GL-------L----I--G-IADG-H---A-R-A-R-----L-LVIDA--------G------------- |
| H. influenza | 211 | -THL-NAM-P--------G-----------------G-I-DG-H-N----RI--------L-VID-I-A----G----L------G-T |

L75917

| | | |
|---|---|---|
| Exon Trap | | CDCHPVGAAGKICNQTTGQCPCKDGVTGLTCNRCAPGFQQSRSPVAPCV |
| netrin-2 | 381 | CDCHPVGAAGKICNQTTGQCPCKDGVTGLTCNRCAKGFQQSRSPVAPC- |
| netrin-1 | 406 | CDCHPVGAAG-TCNQTTGQCPCKDGVTG-TCNRCAKG-QQSRSP-APC- |
| UNC-6: | 410 | C-CHPVG--G--CNQ---GQC-CK-GVTG-TCNRCAKG-QQSRS-V-PC- |

```
Exon Trap      425  HSPSLSAETPIPGPTEDSSFVQPQCDSHCKPARGSYRISLKKFCKKDY
netrin-2            ----------I-------S---P-DCDS-CKPA-G-Y-I--KK-CKKDY
netrin-1       450  ----------P-PT--SS---P-DCDS-CK----G---I--KK-CKKDY
```

L48770-48771

```
RAB26 RT-PCR        MLVGDSGVGKTCLLVRFKDGAFLAGTFISTVGIDFRNKVLDVDGVKAKLQMWDTAGQERFRSVTHAYYRDAHALLLLMDVINKASFDN
rat Rab26      1    MLVGDSGVGKTCLLVRFKDGAFLAGTFISTVGIDFRNKVLDVDG-K-KLQ-WDTAGQERFRSVTHAYYRDAHALLLLYD-TNK-SFDN
```

L48792

```
Exon Trap           FQNHFEPGVYVCAKCGYELFSSRSKYAHSSFWPAFTETIIADSVAKRPEHNRSFALKV·SCGKCGNGLGHEFINDGPKPGQSRF
pilB Protein   410  -----F--PG-YV-----G--LFSS---KY------WP-FT---I-A-SV-------V·-------------LGH-F---DGP------
S. cerevisiae  68   -----E-GVY-CA-CD--L-SS----K-------WPAF--E---------------A---C--C---LGH-F---G-K-------
C.elegans      55   F--HFE-G-YVC------CG-ELF-S---K-----WPAF--E-------------V·-C--C---LGH-F-NDGPK--------
H.influenza    241  -----F--G-YV-----G-----FSS--K-----WP-FT--I-D-V---------·-------GN-LGH-F--DGPK-G--R-
```

FIG. 2B

| | |
|---|---|
| 1 | GGAGCTCGGTTGGAAACCCCCCGAGGCATAATAGGCGCTCGATAAATGTGCAATAGGTGAACATGTGGTGGC |
| 73 | TTGCAGCCGTCTGGGGGAGACAGCAGGTTCTGGGCTGGGCAGGGAATTATTGGATCAACGGGCATCTTACA |
| 145 | GGAAAGACTCTCAGCTCCCTGCCGCCTAGGACTGTCCAGCCCATCTATGCCCTCTCCCAGCCTGTGCCCCA |
| 217 | AAGCTGGAGCTGCCACTCTAGGGGTGAGGGGTGGGGTGGGAGGGGAGGCGAAGCACTGCGGCCTGAGTTG |
| 289 | CAGGTGGGGGAGGGGAGGCGGAGCTTCTTTGTTGCAGAAGGTGCCAGGAGGGGCAGGGCCAGTGGAGAGG |
| 361 | TGGAGGTGGGAGAGGCCCCAGCCAGGGCTGGGACAGGTGGCTGGGTCCCTGGGGAGCAATAAGTCCCGCT |
| 433 | TGGGCGCTGTGGGGAGGCCCTTCCTAACTCCCAAACACCATCTGTGAGGGCTGGGGGTGGGGGCAGAGTAGC |
| 505 | GTGTGCAGAGGACTGTTCCTGGGGAGAGGCCCTGTGACCAGCGGCCTCCTCCCTGGGAGCTGGCGGTACAA |
| 577 | TGGCCCTCTGGGCCCACGGCCTCCCGCCGCTGCTGCTGACCCAGATGAACAATTGGGGCAGGGCTGAGCCCC |
| 649 | AGGCACCTACTTTCCCCCACCCCAGAAGCCACCAGACGTTCTGCAGACCCAGTCCTGGCTCACAGGGAAGC |
| 721 | TGAGCTGGAGACAAAGCCAGCCCCTCTGATGAGGGTGGAAGAGGCTGCTGGCCACTGTCCCTCTTGCAGCCT |
| 793 | GGCTGGCAGCCAGTCTGGCAGTGCCCTGACGTCCAGAGACAGCTTGGGTTTCCCCAGAGGCTTGTCTCTGG |
| 865 | CCAGTGGGACCCCTCTGTCAGGCCTGGGCTTTTCTCTCCACTGTCCCAGAATGATGATCTCAGCCCCCATAG |
| 937 | TCCCCCCAGGGTTCCTCCCACCCTTAGGGTGGGGTGTCGGGGGTGGGGGTTGGGAGCCAGAAGGACCTTGA |
| 1009 | AGAGGGTGGTTGGGACGTTTCAGGTTCTAAGCTTGACCCACAGAGCGGAGCGTGAGCCCCGTCAGGTTGAGG |
| 1081 | TCCCTCAACTTGTAAAGGACACAATTCCATTCTCTTTATCAGGAAGCTGAGGGGCAGGGCCCTGTGGCAGA |
| 1153 | GAGAGAGCCCCTTAGCCCTCTCTGTTCAGTCCTCCGGTGCCCCCATCCCTGTGCATCTGTGGCTGTCACATG |
| 1225 | CAGATGTGTGGCAAGGAGAAGGTGCCCACCAGCCAGTGTCAGTTGCTCCAGGAGCCAAGCCAGGTGCCCTAT |
| 1297 | CACCCTGTCTTCCCGTTCCTCCCCTCCATGGTCAGGCCCTCCTGCTCCCTCCTCTGGTCCTTCAGTTTCCCC |
| 1369 | TAGGAGGCTTCCGTGTCCTCCTGCCCCTCCTCTCCCAACAGCGGGATGCGTCTACCTCTCCATTCTCTTCC |
| 1441 | TCCTGGTCCTTGCTCATCTCTGGTCGTGTCCAGGGTAGCACCCACGTGGCCTCCTCCACCAGCTGCAGGCCT |
| 1513 | GGCCTCCCATCTGAAACGGGCATTCAGGCCTCGATGCTGGCCCTGCACGGAACTTGTTCCCTGCCCCTCCC |
| 1585 | TGGGATGCTTGGCCTCCTCTGTCAAGGACCTGAAAGTCGGAGGGGAGGAGGTTTCTCTGACCAGAGCTGTTC |
| 1657 | CTGGACCCTCTTTGGTGGTGTCGCTCCCAGGCACAGCTACCCCATCCCCAGCTAGTCCCCAGGCACCCAGC |
| 1729 | TGGGCTTCTGCCTCAGTTTCCCTGCCCAAACGTGCTGTGACGTAGGGCAGTGGGCTCCGGGTTGCGACCAGC |
| 1801 | CCCTTCCCATGATTAAACCCTACTCCCTGCCCCTGCAGAGGGGTCCTCAACAGCTAACCAAGCCCCCGAACC |
| 1873 | CCAAGAAGCCACCCCATCCCACCCTCCAGCTTCCATGTCCTCCCTGCCAGCTGGGCCCGTGGCAGAGGTGCC |
| 1945 | CCTAGAAACTTGCAGACCCAGGGAGCTTTGGGATCAGAATCTGGCCTGGTGCAGGGATGCTGGCCTCATGT |
| 2017 | CTTAGCCCAGCTCAGGCCCATGGGGGTGCCCCCCCTTCCTCAACATGGGCAGGAGACACTCCAATTTGTGCAG |
| 2089 | CTCTCGACTTGGGCCTGATGCCACTTGAGACTCATCAAATCCAACAGCTTCAGAGCGCGTGCTGAGTAACAG |
| 2161 | GCATCTGGCAGGTGAGGAAACAGGAGCCCAAGACATGCAGCCAGAAATGGGGCAGTTGGATTCAAAATTAGA |
| 2233 | CCTGACCGAATCCTGGGTTCCTTCTACTCGAGTAGATGCTGCTTTGGGGATGACCCTTCAACTGGTGGTTAC |
| 2305 | TTGGCTTCCCTACCTGGGGAACATCCAGGGCCTCTGCTGTCAGACCCGGGGCCTTGCCTGCCTGATGGTCTT |
| 2377 | CAGGGAGGAGCCGACCCAGACCCCCGTCCAGCACGTGGCACAGCCCAGGAGCAGTAAAGACCTGGCTGTGG |
| 2449 | GCCCAGGACCCTGCTGGGTGGTCCCCACGGGCTGCGAAGGCTGAGCTGCCCCCTCCAGACCCCTCCCGCC |
| 2521 | AGCGCATTCCTGCCTCCCGGCCCCTCCCCTGGCTCCCGGGCCTCCAGCCCCCTTCCCCGCTGGCCCAGCC |
| 2593 | CGCGTCTGAATCTGCTTCTGATTCCAGCTCTGCGGATGAGGCCCCCTCCCCTCCCCTGCCTCCTTCCCGACCC |
| 2665 | GAGCAGCCCCGCCCCGGCTGGGCCCGGGCTTGCGCCTGCTGCGCCCCCACCCCTCCTGGCACAGCTCGT |
| 2737 | CCGCCCTCGCTGCAGCCGGGAGGAGCGGCGGCCCGTGCACCGCAGGCCCGCCGCCCACGGCCCTTCCCG |
| 2809 | GGAGGCCGGGAGACCTGCTCCGCCCGGCCCTCGGTGGGTGAGTGCGAGCGGCGGGTGGGGCCTCCGCGGGCG |

FIG. 3A

```
2881  GAGGCACCGGGAGCGGGGGCGACGCCTGTCATCGCTCTAGGCCCAGCGGGAGGACGCGCCAACATCCCCGCT
2953  GCTGTGCTGGGCCCGGGCGTGCCCGCCGCTGCTCCCACCTCTGGGCCGGGCTGGGCCGCCGGGGCCCT
3025  GTTCCTCGGCATTGCGGGCCTGGTGGGCAGAGCCGCGGAGAGGGCTTCTTTTCCCCAAGGGCAGCGTCTTGG
3097  GGCCCGGCCACTGGCTGACCCGCAGCGGCTCCGGCCATGCCTGGCTGGCCCTGGGGCTGCTGCTGACGGCA
3169  GGCACGCTCTTCGCCGCCCTGAGTCCTGGGCCGCCGGCGCCGGCCGACCCCTGCCACGATGAGGGGGTGCG
3241  CCCCGCGGCTGCGTGCCAGGACTGGTGAACGCCGCCCTGGGCCGCGAGGTGCTGGCTTCCAGCACGTGCGGG
3313  CGGCCGGCCACTCGGGCCTGCGACGCTCCGACCCGGCGACGGGCACACTCCCCGCCCTCCTTACTTCCCCA
3385  GGGGGCACGGCCAGCCCTCTGTGCTGGCGCTCGGAGTCCCTGCCTCGGGCGCCCTCAACGTGACTCTCACG
3457  GTGCCCCTGGGCAAGGCTTTTGAGCTGGTCTTCGTGAGCCTGCGCTTCTGCTCAGCTCCCCCAGCTCCGTG
3529  GCCCTGCTCAAGTCTCAGGACCATGGCCGCAGCTGGGCCCCGCTGGGCTTCTTCTCCTCCCACTGTGACCTG
3601  GACTATGGCCGTCTGCCTGCCCCTGCCAATGGCCCAGCTGGCCCAGGGCCTGAGGCCCTGTGCTTCCCCGCA
3673  CCCCTGGCCCAGCCTGATGGCAGCGGCCTTCTGGCCTTCAGCATGCAGGACAGCAGCCCCCAGGCCTGGAC
3745  CTGGACAGCAGCCCAGTGCTCCAAGACTGGGTGACCGCCACCGACGTCCGTGTAGTGCTCACAAGGCCTAGC
3817  ACGGCAGGTGACCCCAGGACATGGAGGCCGTCGTCCCTTACTCCTACGCAGCCACCGACCTCCAGGTGGGC
3889  GGGCGCTGCAAGTGCAATGGACATGCCTCACGGTGCCTGCTGGACACACAGGGCCACCTGATCTGCGACTGT
3961  CGGCATGGCACCGAGGGCCCTGACTGCGGCCGCTGCAAGCCCTTCTACTGCGACAGGCCATGGCAGCGGGCC
4033  ACTGCCCGGGAATCCCACGCCTGCCTCGGTGAGGCCTTGGAGGGTGGCCTGGGGACCTTGGACACAACCAGC
4105  CTGCCCCTGACCCATCCCTCCCTGCAGCTTGCTCCTGCAACGGCCATGCCCGCCGCTGCCGCTTCAACATGG
4177  AGCTGTACCGACTGTCCGGCCGCCGCAGCGGGGGTGTCTGTCTCAACTGCCGGCACAACACCGCCGGCCGCC
4249  ACTGCCACTACTGCCGGGAGGGCTTCTATCGAGACCCTGGCCGTGCCCTGAGTGACCGTCGGCTTGCAGGG
4321  GTGAGCCACCACCGGCCACCTGCAGGCCCTCACCCTCTGACTTCCCAGATCCCCAGACAGGCTTCTGACCAG
4393  GCCCTTCCCACCTCTGTCCTCAGCCTGCGACTGTCACCCGGTTGGTGCTGCTGGCAAGACCTGCAACCAGAC
4465  CACAGGCCAGTGTCCCTGCAAGGATGGCGTCACTGGCCTCACCTGCAACGGCTGCGCGCTGGCTTCCAGCA
4537  AAGCCGCTCCCCAGTGGCGCCCTGTGTTAGTGAGTGACCCTGCCCGCCTCAGCCACCAAGCCAAGGCCACC
4609  CCAGCTCCCTGCTGTTGTCCCGTCTATTCCCCGAGCCCTGCAGATCTCTCTGCCCCTCCATCGCAGGCCATT
4681  CTCCCTCCCTCTCTGCAGAGACCCCTATCCCTGGACCCACTGAGGACAGCAGCCCTGTGCAGCCCCAGGGTG
4753  AGTGGACACAGGACAGGGCCCCAGACTGGCATGACTTTGGGGAGGGGCTCTGGGAGGAGAGGGTGGGAA
4825  AGGGAGTCTGTGCCAGCCTCCCACCTTCTACCCAGACTGTGACTCGCACTGCAAACCTGCCCGTGGCAGCTA
4897  CCGCATCAGCCTAAAGAAGTTCTGCAAGAAGGACTATGGTAGGTGCCCTCAGGCCTCCGCGGACCTTCCCA
4969  CCTTCCTCCTCTCCCTACCTTCCCTCCTCCGCCAGCTTCCCCTTGGAACGCCTTGACCCTTGCTGGGCCCA
5041  AGGCCCATCCTCATCCCTCAGGTCCTCCACGGGCAGCGACCCCGCCCTTCAGCCCCCACTGCCCTCCTGGT
5113  GTCCTCCCCGTGCCTCCCCCTACCGCGGGCAGGCCGCCCCTTCCTGACCCCGCCCCCTCTCGCTCTCCCCGC
5185  AGCCGGTGCAGGTGGCCGGTGGGTGCCGCGGCGAGGCGCGCGGGCGCGTGGACACGCTTCCCGGTGGCCGTGCT
5257  CGCCGTGTTCCGGAGCGGAGAGGAGCGCGCGCGGCGGGGAGTAGCGCGCTGTGGGTGCCCGCCGGGATGC
5329  GGCCTGCCGGCTGCCCGCGCCTGCTCCCCGGCCGCGCTACCTCCTGCTGGGGGCGGGCCTGGAGCCGCGGC
5401  TGGGGCGCGGGGGGCCGGGGCCCGGGCTCATCGCCGCCCGCGGAAGCCTGCGTGCTACCCTGGAGGGACGC
5473  GTGGACGCGCGCCCTGCGGAGGCTGCAGCGACGCGAACGGCGGGGGCCTGCAGCGCCGCCTGAGCCCGCCG
5545  GCTGGGCAGGCCGGCCGCTGCTCCCACATCTAGGCGCACGTTCACCCTGTGCCTTCGCCTGCCAAGGAGTCC
5617  TTGCTCGGTCGCGCGTGTCGCCACCTGGCCGCGCCCCGTCCCGCGGCAGCTCCCTCGGTACCTCCCG
5689  TCTGGCCCTGGGGGATGTGACCGGCGCACGGACAGCCCGCCCCGCACAGAGGCAGATGATATGGCACACCC
```

FIG. 3B

```
5761  GGAGGACCCCATGGTCTCCCGCCCTCTGGCTGTCGGCCCTGTCCCAGGGGCACTGGGATACCCGGAAGGCTG
5833  TGAATCCTTCGTGATGCCGGGCCCTCTGGGGATCTCAGATCATCCCCGGGCCGCTGTGATGCACCCCCAC
5905  CTGTGCCGGCGACCCGCCAGGAGCGCACTGACCTCCCCAAAGACTGTGGCCACCGCAGGCGCCTTGGACCCCC
5977  ATGGGGACAGGGCGTCCCCTGCCTCCTGCAGCCCCACGAGGGCGGCGGCCTTGGCCCTGCGGCTGGGCGTC
6049  CGCGTCCGGCGCCCCGCGGCGTCTGCTGCCGGGTCCCGTAACTTTCTTGGCCGCCTGTGTCCCCGTCTGCC
6121  GGCTCCGTCCGGCCGTCCCTCTCTCTGCCCGCGTCTCTGACCCTCGGCGCACAGCTCCTCAGCTCAGGGCCC
6193  GTCCCAGAACCTCCTTCCAGCCCTTCTCCCCCGACTCGGGAAGGGACGTCGTGCCCACGCGGTTCCGGATCC
6265  ACGCGTGACCCGGCCGGACCGCGACTCCGACAGGCGGCTGTCCGGGCCCCGATGCCCTCGGCAGGGCCGTG
6337  CCACCCCCGCCCTTGTTGTCCCCCCGGGACCGGCACTGCCGTTTGCCTCCTCTCCGCACGGGACCGGTTC
6409  CCGGCCGGCCCCAGCTTCCGCCGCTGCCGGCCGCCGACCGTCAGCGCGCATGCCCAGAGCCCGGGCAGGCCGGA
6481  GCCCCGCCGGCTCTCCGGGGTTGGGCACAGGGCGACAGCTGGCGGGGGCGGGCCGAGCACGCGCGTGCGCA
6553  GAAAGGCCGGCGCGGCAGGCTGAGGAGAAAGCGGCGCGCGGAGGTGGGTGCGCTCGGGGCGTGCGGGGGCG
6625  CGCGGCGGGTGGCGGGTGGCGGGGCCCGGTCCCCGCTGTCACCGCGGTCGGCGCGTGCTGGGGCGGGAGC
6697  GTGGGGCCGGCTGCGTGCCCCATTCGAGGCGGGGATCCCCGGCCACGCGCCGGTTCGGGCTCCAGAGCC
6769  CGGCACCGCCCGGCGCTGCAGCTGCGGCTTGGCCT
```

FIG. 3C

```
  1   ATGCCTGGCTGGCCCTGGGGGCTGCTGCTGACGGCAGGCACGCTCTTCGCCGCCCTGAGTCCTGGGCCGCC
       M  P  G  W  P  W  G  L  L  L  T  A  G  T  L  F  A  A  L  S  P  G  P  P
 72   GGCGCCCGCCGACCCCTGCCACGATGAGGGGGGTGCGCCCGCGGCTGCGTGCCAGGACTGGTGAACGCCG
       A  P  A  D  P  C  H  D  E  G  G  A  P  R  G  C  V  P  G  L  V  N  A
143   CCCTGGGCCGCGAGGTGCTGGCTTCCAGCACGTGCGGGCGGCCGGCCACTCGGGCCTGCGACGCCTCCGAC
       A  L  G  R  E  V  L  A  S  S  T  C  G  R  P  A  T  R  A  C  D  A  S  D
214   CCGCGACGGGCACACTCCCCGCCCTCCTTACTTCCCCAGGGGGCACGGCCAGCCCTCTGTGCTGGCGCTC
       P  R  R  A  H  S  P  A  L  L  T  S  P  G  G  T  A  S  P  L  C  W  R  S
285   GGAGTCCCTGCCTCGGGCGCCCCTCAACGTGACTCTCACGGTGCCCCTGGGCAAGGCTTTTGAGCTGGTCT
       E  S  L  P  R  A  P  L  N  V  T  L  T  V  P  L  G  K  A  F  E  L  V
356   TCGTGAGCCTGCGCTTCTGCTCAGCTCCCCCAGCCTCCGTGGCCCTGCTCAAGTCTCAGGACCATGGCCGC
       F  V  S  L  R  F  C  S  A  P  P  A  S  V  A  L  L  K  S  Q  D  H  G  R
427   AGCTGGGCCCCGCTGGGCTTCTTCTCCTCCCACTGTGACCTGGACTATGGCCGTCTGCCTGCCCCTGCCAA
       S  W  A  P  L  G  F  F  S  S  H  C  D  L  D  Y  G  R  L  P  A  P  A  N
498   TGGCCCAGCTGGCCCAGGGCCTGAGGCCCTGTGCTTCCCGCACCCCTGGCCCAGCCTGATGGCAGCGGCC
       G  P  A  G  P  G  P  E  A  L  C  F  P  A  P  L  A  Q  P  D  G  S  G
569   TTCTGGCCTTCAGCATGCAGGACAGCAGCCCCCAGGCCTGGACCTGGACAGCAGCCCAGTGCTCCAAGAC
       L  L  A  F  S  M  Q  D  S  S  P  P  G  L  D  L  D  S  S  P  V  L  Q  D
640   TGGGTGACCGCCACCGACGTCCGTGTAGTGCTCACAAGGCCTAGCACGGCAGGTGACCCCAGGGACATGGA
       W  V  T  A  T  D  V  R  V  V  L  T  R  P  S  T  A  G  D  P  R  D  M  E
711   GGCCGTCGTCCCTTACTCCTACGCAGCCACCGACCTCCAGGTGGCGGGCGCTGCAAGTGCAATGGACATG
       A  V  V  P  Y  S  Y  A  A  T  D  L  Q  V  G  G  R  C  K  C  N  G  H
782   CCTCACGGTGCCTGCTGGACACACAGGGCCACCTGATCTGCGACTGTCGGCATGGCACCGAGGGCCCTGAC
       A  S  R  C  L  L  D  T  Q  G  H  L  I  C  D  C  R  H  G  T  E  G  P  D
```

FIG. 4A

```
853  TGCGGCCGCTGCAAGCCCTTCTACTGCGACAGGCCATGGCAGCGGGCCACTGCCCGGGAATCCCACGCCTG
      C  G  R  C  K  P  F  Y  C  D  R  P  W  Q  R  A  T  A  R  E  S  H  A  C
924  CCTCGCTTGCTCCTGCAACGGCCATGCCCGCCGCTGCCGCTTCAACATGGAGCTGTACCGACTGTCCGGCC
      L  A  C  S  C  N  G  H  A  R  R  C  R  F  N  M  E  L  Y  R  L  S  G
995  GCCGCAGCGGGGGTGTCTGTCTCAACTGCCGGCACAACACCGCCGGCCGCCACTGCCACTACTGCCGGGAG
      R  R  S  G  G  V  C  L  N  C  R  H  N  T  A  G  R  H  C  Y  C  R  E
1066 GGCTTCTATCGAGACCCTGGCCGTGCCCTGAGTGACCGTCGGCTTGCAGGGCCTGCGACTGTCACCCGGT
      G  F  Y  R  D  P  G  R  A  L  S  D  R  R  A  C  R  A  C  D  C  H  P  V
1137 TGGTGCTGCTGGCAAGACCTGCAACCAGACCACAGGCCAGTGTCCCTGCAAGGATGGCGTCACTGGCCTCA
      G  A  A  G  K  T  C  N  Q  T  T  G  Q  C  P  C  K  D  G  V  T  G  L
1208 CCTGCAACCGCTGCGCGCCTGGCTTCAGCAAAGCCGCTCCCAGTGGCGCCCTGTGTTAAGACCCCTATC
      T  C  N  R  C  A  P  G  F  Q  Q  S  R  S  P  V  A  P  C  V  K  T  P  I
1279 CCTGGACCCACTGAGGACAGCAGCCCTGTGCAGCCCCAGGACTGTGACTCGCACTGCAAACCTGCCCGTGG
      P  G  P  T  E  D  S  S  P  V  Q  P  Q  D  C  D  S  H  C  K  P  A  R  G
1350 CAGCTACCGCATCAGCCTAAAAGAAGTTCTGCAAGAAGGACTATGCGGTGCAGGTGGCCGTGGGTGCGCGCG
      S  Y  R  I  S  L  K  K  F  C  K  K  D  Y  A  V  Q  V  A  V  G  A  R
1421 GCGAGGCGCGCGGCGCGTGGACACGCTTCCCGGTGGCGGTGCTGGCCGTGTTCCGGAGCGGAGAGGAGCGC
      G  E  A  R  G  A  W  T  R  F  P  V  A  V  L  A  V  F  R  S  G  E  E  R
1492 GCGCGGCGCGGGAGTAGCGCGCTGTGGGTGCCCGCCGGGGATGCGGCCTGCGGCTGCCCGCGCCTGCTCCC
      A  R  R  G  S  S  A  L  W  V  P  A  G  D  A  A  C  G  C  P  R  L  L  P
1563 CGGCCGCCGCTACCTCCTGCTGGGGGGCGGGCCTGGAGCCGCGGCTGGGGCGCGGGGGCCGGGGCCCG
      G  R  R  Y  L  L  L  G  G  G  P  G  A  A  A  G  G  A  G  G  R  G  P
1634 GGCTCATCGCCGCCCGCGGAAGCCTCGTGCTACCCTGGAGGGACGCGTGGACGCGGCGCCTGCGGAGGCTG
      G  L  I  A  A  R  G  S  L  V  L  P  W  R  D  A  W  T  R  R  L  R  R  L
1705 CAGCGACGCGAACGGCGGGGGCGCTGCAGCGCCGCCTGA
      Q  R  R  E  R  R  G  R  C  S  A  A
```

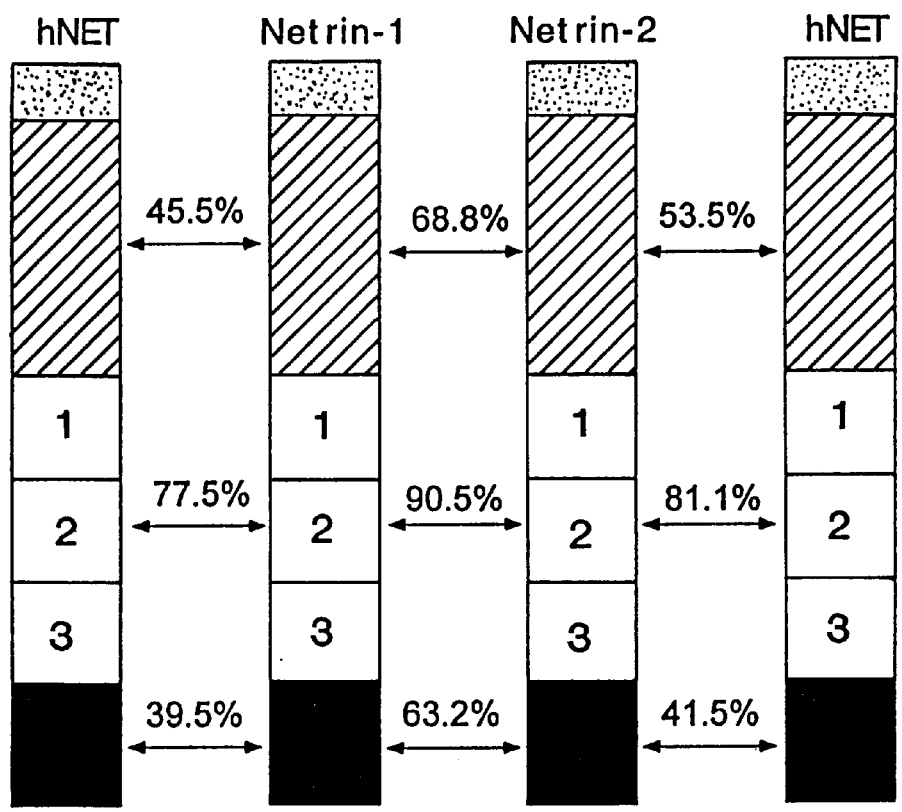
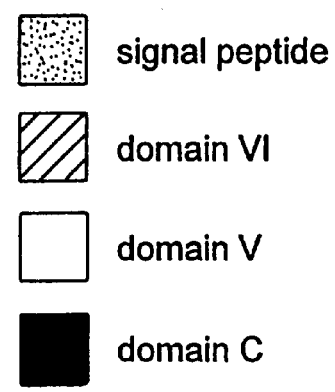
FIG. 6

```
1
G AAG GTC CTG GTG ACG GTC CTG GAA CTC TTC CTG CCA TTG CTG CTG TTT TCT GGG ATC CTC ATC TGG CTC CGC TTG AAG ATT CAG TCG GAA
  K   V   L   V   T   V   L   E   L   F   L   P   L   L   L   F   S   G   I   L   I   W   L   R   L   K   I   Q   S   E

AAT GTG CCC AAC GCC ACC ATC TAC CCT GGC CAG TCC ATC CAG GAG CTG CCT CTG TTC ACC TTC CCT CCG CCA GGA GAC ACC TGG GAG
  N   V   P   N   A   T   I   Y   P   G   Q   S   I   Q   E   L   P   L   F   T   F   P   P   P   G   D   T   W   E
              100                                                       200

CTT GCC TAC ATC CCT TCT CAC AGT GAC GCT GCC AAG GCC GTC ACT GAG ACA GTG CGC AGG GCA CTT GTG ATC AAC ATG CGA GTG CGC GGC
  L   A   Y   I   P   S   H   S   D   A   A   K   A   V   T   E   T   V   R   R   A   L   V   I   N   M   R   V   R   G

TTT CCC TCC GAG AAG GAC TTT GAG GAC TAC ATT AGG TAC GAC AAC TGC TCG TCG AGT TAC ACA CGG TTC CAC ACT TCC CTT TTC CCG GTG AAA GAG ACA GAA GGC TGG CAT ACT ACT TCC CTG TTT TTT CCA AAC CCA GGA CCA AGG GAA CTA ACA TCC CCT
  F   P   S   E   K   D   F   E   D   Y   I   R   Y   D   N   C   S   S   S   Y   T   R   F   S   Y   T   R   R   N   Y   M   W   T   Q   T   G
                              300                                                       400                                                       500

AAC CAC AGC AAG GAG CCC CTG GCG CTA GCG GTC AAA TAT AAA TAT AAG GAC GAG GTC CCT GCG GTG CAG CAT GCT GTG GAC CGG GCC ATC ATG GAG TAC CAT GCC GAT GCC
  N   H   S   K   E   P   L   A   L   A   V   K   Y   K   Y   H   L   R   F   S   Y   T   R   R   N   Y   M   W   T   Q   T   G

TCC TTT TTC CTG AAA GAG ACA GAA GGC TGG CAT ACT ACT TCC CTG TTT TTT CCA AAC CCA GGA CCA AGG GAA CTA ACA TCC CCT
  S   F   F   L   K   E   T   E   G   W   H   T   T   S   L   F   F   P   N   P   G   P   R   E   L   T   S   P

GAT GGC GAA CCT GGG TAC ATC CGG GAA GGC TTC CTG GCC GTG CAG CAT GCT GTG GAC CGG GCC ATC ATG GAG TAC CAT GCC GAT GCC
  D   G   E   P   G   Y   I   R   E   G   F   L   A   V   Q   H   A   V   D   R   A   I   M   E   Y   H   A   D   A
                              600

FIG. 8A
```

```
GCC ACA CGC CAG CTG TTC CAG AGA CTG ACG GTG ACC ATC AAG AGG TTC CCG TAC CCC GAC CCC TTC ATC GCA GAC CCC TTC CTC GTG GCC ATC
 A   T   R   Q   L   F   Q   R   L   T   V   T   I   K   R   F   P   Y   P   P   F   I   A   D   P   F   L   V   A   I
                                                                                                 800
CAG TAC CAG CTG CCC CTG CTG CTG CTG AGC TTC ACC TAC ACC GCG CTC ACC ATT GCC CGT GCT GTC CAG GAG AAG GAA AGG AGG
 Q   Y   Q   L   P   L   L   L   L   S   F   T   Y   T   A   L   T   I   A   R   A   V   Q   E   K   E   R   R
CTG AAG GAG TAC ATG CGC ATG ATG GGG CTC AGC AGC TGG CAC TGG AGT GCC TGG TTC CTC TTG TTT CTC CTC ATC GCC
 L   K   E   Y   M   R   M   M   G   L   S   S   W   L   H   W   S   A   W   F   L   L   F   L   L   I   A
900
GCC TCC TTC ATG ACC CTG CTC TTC TGT GTC AAG GTG AAG CCA AAT GTA GCC ATG GTC TTC AGC TTC TTC TTC CTC GCC TTC
 A   S   F   M   T   L   L   F   C   V   K   V   K   P   N   V   A   M   V   S   F   F   F   L   A   F
                                1000
CTG CTG TGC TTC GCC ATC TCT ACC ATC ATC TCC TTC GCC TAC TTC ATG GTC TTC AGC TTC TTC TTC AGC CAG AAG CTC TGC GGA GGC
 L   L   C   F   A   I   S   T   I   I   S   F   A   Y   F   M   V   S   F   F   F   S   Q   K   L   C   G   G
                                                                1100
TTC CTC TAC TTT CTG GCC ATG GCA ATG GGA GCC CAG CTC ATT GGG AAA TTT GAG GCG ATG CTG CTG GAC TGC TCC TGC CTC
 F   L   Y   F   L   A   M   A   M   G   A   Q   L   I   G   K   F   E   A   M   L   L   D   C   S   C   L
                                                                1200
CTG TCT AAT GTC GCC ATG GGA GCC CAG CTC ATT GGG AAA TTT GAG GCG AAG GGC ATG CTG CTG GAC TGG CGA GAC CTG CTG AGT
 L   S   N   V   A   M   G   A   Q   L   I   G   K   F   E   A   K   G   M   L   L   D   W   R   D   L   L   S
                                                        1300
CCC GTC AAC GTG GAC GAC GAC TTC TGC TTC GGG CAG GTG CTG GGG ATG CTG CTG GAC TCT GTG CTC TAT GGC CTG GTG ACC TGG TAC
 P   V   N   V   D   D   D   F   C   F   G   Q   V   L   G   M   L   L   D   S   V   L   Y   G   L   V   T   W   Y
```

FIG. 8B

```
ATG GAG GCC GTC TTC CCA GGG CAG TTC GGC GTG CCT CAG CCC TGG TAC TTC ATC ATG CCC TCC TAT TGG TGT GGG AAG CCA AGG GCG
 M   E   A   V   F   P   G   Q   F   G   V   P   Q   P   W   Y   F   I   M   P   S   Y   W   C   G   K   P   R   A

1500
GTT GCA GGG AAG GAG GAA GAC AGT GAC CCC GAG AAA GCA CTC AGA AAC GAG TAC TTT GAA GCC GAG CCA GAG GAC CTG GTG GCG GGG
 V   A   G   K   E   E   D   S   D   P   E   K   A   L   R   N   E   Y   F   E   A   E   P   E   D   L   V   A   G

ATC AAG ATC AAG CAC CTG TCC AAG GTG TTC AGG GTG GGA AAT AAG GAC AGG GCG GCC GTC ATG CTC CTC ACA GGT CTC AAC CTG TAC GAG GGA
 I   K   I   K   H   L   S   K   V   F   R   V   G   N   K   D   R   A   A   V   M   L   L   T   G   L   N   L   Y   E   G

1600
CAG ATC ACC AGC GGG TAT GAA ATT TCC CAG GAT ATG GTT CAG ATC CGG AAG AGC CTG GGC CTG TGC CCG CAG CAC GAT ATC CTG TTT GAC
 Q   I   T   S   G   Y   E   I   S   Q   D   M   V   Q   I   R   K   S   L   G   L   C   P   Q   H   D   I   L   F   D

1700
GCA TAC ATC AGC GGG TAT GAA ATT TCC CAG GAT ATG GTT CAG ATC CGG AAG AGC CTG GGC CTG TGC CCG CAG CAC GAT ATC CTG TTT GAC
 A   Y   I   S   G   Y   E   I   S   Q   D   M   V   Q   I   R   K   S   L   G   L   C   P   Q   H   D   I   L   F   D

AAC TTG ACA GTC GCA GAG CAC CTT TAT TTC TAC GCC CAG CTC AAG GGC CTG TCA CGT CAG AAG TGC CCT GAA GAA GTC AAG CAG ATG CTG
 N   L   T   V   A   E   H   L   Y   F   Y   A   Q   L   K   G   L   S   R   Q   K   C   P   E   E   V   K   Q   M   L

1800
CAC ATC ATC GGC CTG GAG GAC AAG TGG AAC TCA CGG AGC CGC TTC CTG AGC GGG GGC ATG AGG CGC AAG CTC TCC ATC GCC CTC
 H   I   I   G   L   E   D   K   W   N   S   R   S   R   F   L   S   G   G   M   R   R   K   L   S   I   A   L

1900
ATC GCA GGC TCC AAG GTG CTG ATA CTG GAC GAG CCC ACC TCG GGC ATG GAC GCC ATC TCC AGG AGG GCC ATC TGG GAT CTT CTT CAG CGG
 I   A   G   S   K   V   L   I   L   D   E   P   T   S   G   M   D   A   I   S   R   R   A   I   W   D   L   L   Q   R

```
CAG AAA AGT GAC CGC ACC ATC GTG CTG CTG ACC ATC CAC TTC ATG GAC GAG GCT GAC CTG CTG GGA GAC CGC ATC GCC ATC ATG GCC AAG GGG
 Q   K   S   D   R   T   I   V   L   L   T   I   H   F   M   D   E   A   D   L   L   G   D   R   I   A   I   M   A   K   G
                                        2100                                        2200

GAG CTG CAG TGC TGC GGG TCC TCG CTG TTC CTC CAG CTG GTC CAC CAC CAC TTC CTC AAG CAG AAA TAC GGT GCC TAT CAC ATG ACG CTG GTG AAG GAG CCG CAC TGC AAC
 E   L   Q   C   C   G   S   S   L   F   L   Q   L   V   H   H   H   F   L   K   Q   K   Y   G   A   Y   H   M   T   L   V   K   E   P   H   C   N

CCG GAA GAC ATC TCC CAG CTG GTC TTT GAA GGT CTC TTT GCT AAA CTG GAG AAG CCC AAC GTG CCC AAC GCC ACG CTG GAG AGC AGC GCT GGG GCC GAG CTG TCT TTC ATC CTT CCC
 P   E   D   I   S   Q   L   V   F   E   G   L   F   A   K   L   E   K   P   N   V   P   N   A   T   L   E   S   S   A   G   A   E   L   S   F   I   L   P
                    2300                                        2400

AGA GAG AGC ACG CAC GAG GAA GTC TTC CTT CGG AGG TTT GTC GCC AGC GAC TGG GCT GTC AAG CTC AAC ACT GGG CTC GCC CTG CAC CAG CAA TTC TGG GCC ATG GAC CCC TCC GAC GGC ATT GGA GCA CTC ATC GAG
 R   E   S   T   H   E   E   V   F   L   R   R   F   V   A   S   D   W   A   V   K   L   N   T   G   L   A   L   H   Q   Q   F   W   A   M   D   P   S   D   G   I   G   A   L   I   E

ACC ACC ATG GAG GAA GTC TTC CTT CGG AGG TTT GTC GCC AGC GAC TGG GCT GTC AAG CTC AAC ACT GGG CTC GCC CTG CAC CAG CAA TTC TGG GCC ATG GAC CCC TCC GAC GGC ATT GGA GCA CTC ATC GAG
 T   T   M   E   E   V   F   L   R   R   F   V   A   S   D   W   A   V   K   L   N   T   G   L   A   L   H   Q   Q   F   W   A   M   D   P   S   D   G   I   G   A   L   I   E
                                                                2500                                                            2600

CAG CAC GAG AGG CGC ACC GCT GTC AAG ATG GTG GCG GCA CAG GTC CTC GTC ACC TGC GTC ACC CTG GCC CTC CTG GCC ATC TAC AGC
 Q   H   E   R   R   T   A   V   K   M   V   A   A   Q   V   L   V   T   C   V   T   L   A   L   L   A   I   Y   S

TGG CGC GAG TGG AAA ATG GTG GCG GCA CAG GTC CTC GTC ACC TGC GTC ACC CTG GCC CTC CTG GCC ATC TAC AAC TAC TCC TCG GAG
 W   R   E   W   K   M   V   A   A   Q   V   L   V   T   C   V   T   L   A   L   L   A   I   N   Y   S   S   E
2700
```

FIG. 8D

```
2800
CTC TTC GAC GAC CCC ATG CTG AGG CTG ACC TTG GGC GAG TAC GGC AGA ACC GTC CCC TTC TCA GTT CCC GGG ACC TCC CAG CTG GGT
 L   F   D   D   P   M   L   R   L   T   L   G   E   Y   G   R   T   V   P   F   S   V   P   G   T   S   Q   L   G

2900
CAG CAG CTG TCA GAG CAT CTG AAA GAC GCA CTG CAG GCT GAG GGA CAG GAG CCC CGC GAG GTG CTC GGT GAC CTG GAG GAG TTC TTG ATC
 Q   Q   L   S   E   H   L   K   D   A   L   Q   A   E   G   Q   E   P   R   E   V   L   G   D   L   E   E   F   L   I

3000
TTC AGG GCT TCT GTG GAG GGG GGC TTC AAT GAG GAG CGC TGC CTT GTG GCA GCG TCC TTT AGA GAT GTG GGA GAG CGC ACG GTC AAC
 F   R   A   S   V   E   G   G   F   N   E   E   R   C   L   V   A   A   S   F   R   D   V   G   E   R   T   V   N

3100
GCC TTG TTC AAC AAC CAG GCG TAC CAC TCT CCA GCC ACT GCC GTC GTG GAC AAC CTT CTG TTC AAG CTG CTG TGC GGG CCT CAC
 A   L   F   N   N   Q   A   Y   H   S   P   A   T   A   V   V   D   N   L   L   F   K   L   L   C   G   P   H

3200
GCC TCC ATT GTG GTC TCC AAC TTC CCC CAG CCC CGG AGC GCC TTG CAG GCT GCC AAG GAC CAG TTT AAC GAG GGC CGG AAG GGA TTC GAC
 A   S   I   V   V   S   N   F   P   Q   P   R   S   A   L   Q   A   A   K   D   Q   F   N   E   G   R   K   G   F   D

3300
ATT GCC CTC AAC CTG CTC TTC GCC ATG GCA TTT TTG GCC AGT ACG TTC TCC ATC CTG GCG GTC AGC GAG AGG GCC GTG CAG GCC AAG CAT
 I   A   L   N   L   L   F   A   M   A   F   L   A   S   T   F   S   I   L   A   V   S   E   R   A   V   Q   A   K   H

3400
GTG CAG TTT GTG AGT GGA GTC CAC GTG GCC AGT TTC TGG CTC TCT GCT CTG CTG TGG GAC CTC ATC CCC AGT CTG CTG
 V   Q   F   V   S   G   V   H   V   A   S   F   W   L   S   A   L   L   W   D   L   I   P   S   L   L
```

FIG. 8E

```
CTG CTG GTG GTG TTT AAG GCC TTC GAC GTG CGT GCC TTC ACG CGG GAC ACC CTG CTG CTC TAC GGC
 L   L   V   V   F   K   A   F   D   V   R   A   F   T   R   D   T   L   L   L   Y   G
                                                                                      3500
TGG GCC ATC ATC CCC CTC ATG TAC CTG ATG GTC ACC TTC CTC ATG AAC TTC TTC TTG GGG GCG GCC ACT GCC ATC TTC AAC ATC CTG
 W   A   I   I   P   L   M   Y   L   M   V   T   F   L   M   N   F   F   L   G   A   A   T   A   I   F   N   I   L
3600
TCA GGC ATC GCC ACC TTC CTG ATG GTC ACC ATC ATG CGC ATC CCA GCT GTA AAA CTG GAA GAA CTT TCC AAA ACC CTG GAT CAC GTG TTC
 S   G   I   A   T   F   L   M   V   T   I   M   R   I   P   A   V   K   L   E   E   L   S   K   T   L   D   H   V   F
              3700
CTG GTG CCC AAC CAC TGT CTG CCC ATG GCA GTC AGC TTC TAC CAG GAG AAC TTC TAT GCC TGG AGC GCC CCG GGG GTC TTT GTG GCC TCC GAG GTC
 L   V   L   P   N   H   C   L   P   M   A   V   S   F   Y   Q   E   N   F   Y   A   W   S   A   P   G   V   F   V   A   S   E   V
                                3800
GCC GCC CAC TAC TGC AAG AAA TAT AAC ATC CAG TAC CTC ATC CTC TTC CTC ATC GAG ACC AAC CTG CTT CAG AGA CTC CGG GGC ATC CTG TGC GCC CTC
 A   A   H   Y   C   K   K   Y   N   I   Q   Y   L   I   L   F   L   I   E   T   N   L   L   Q   R   L   R   G   I   L   C   A   L
ATG GCC GCC TCA GGG TGC GCC TAC CTC ATT CTT TTC CTG TTT CCT GTG CTT CCT GAG GAC CAA GAT GTA GCG GAC GAG AGG ACC CGG ATC CTG
 M   A   A   S   G   C   A   Y   L   I   L   F   L   F   P   V   L   P   E   D   Q   D   V   A   D   E   R   T   R   I   L
                                                                   4000
CGG AGG AGG CGG ACA TTA TAC ACA GAA TTA TAC ACC CGG ATG CCT GTG CTT CCT GAG GAC CAA GAT GTA GCG GAC GAG AGG ACC CGG ATC CTG
 R   R   R   R   T   L   Y   T   E   L   Y   T   R   M   P   V   L   P   E   D   Q   D   V   A   D   E   R   T   R   I   L
```

```
                                                 4700
CTG TGC ACC CGG CTG GCC ATC ATG GTG CAG GGG CAG TTC AAG TGC CTG GGC AGC CCC CAG CAC CTC AAG AGC AAG TTC GGC AGC GGC TAC
 L   C   T   R   L   A   I   M   V   Q   G   Q   F   K   C   L   G   S   P   Q   H   L   K   S   K   F   G   S   G   Y

4800
TCC CTG CGG GCC AAG GTG CAG AGT GAA GGG CAA CAG GAG CAA GGG GAA GAG CTG GCG GAG TTC AAG GCC TTT GTG GAC CTG ACC TTT CCA GGC AGC GTC
 S   L   R   A   K   V   Q   S   E   G   Q   Q   E   Q   G   E   E   L   A   E   F   K   A   F   V   D   L   T   F   P   G   S   V

4900
CTG GAA GAT GAG CAC CAA GGC ATG GTC CAT TAC CAC CTG CCG GGC CGT GAC CTC AGC TGG GCG AAG GTT TTC GCC CAC CTG AGC TTC GCC CAC CTG CAG CCG CCC ACC
 L   E   D   E   H   Q   G   M   V   H   Y   H   L   P   G   R   D   L   S   W   A   K   V   F   A   H   L   S   F   A   H   L   Q   P   P   T

5000
AAG GAA AAG TAC GGC GTG GAC GAC TAC TCC GTG AGC CAG ATC TCG CTG GAA CAG GTC TTC CTG AGC TTC GCC CAC CTG CAG CCG CCC ACC
 K   E   K   Y   G   V   D   D   Y   S   V   S   Q   I   S   L   E   Q   V   F   L   S   F   A   H   L   Q   P   P   T

GCA GAG GAG GGG CGA TGA GGGGTGGCGCTGTCTCGCCATCAGGGACAGGACAGGACAAGCAGGGCCCATCTTACATCCCTCTCTCCAAGTTTATCTCATCCTTTATTT
 A   E   E   G   R   *

TTAATCACTTTTTTCTATGATGGATATGAAAAATTCAAGCAGTATGCACAGAATGACGAGTCCAGCCCTCATGCCCAGATCAGCATGCCATCTCCATGTCTGCATACTCT
GGAGTCACTTCCTGAGATCACTTCCCAGAGAGACCCAGCTGTGGCAGGCTGTGGGGCAGTCTGTGGGTCAGCTGACCCAGAGAGCTCCGGTGTCTCTGGGGTTGAATTTCTCCAGG
CACTCCCTGGAGAGAGACCAGATCAGAGCCGGGCCAGTGACTTGTCCAAGTTTACACACGACTAATCTCCCCTCGGAGGCTCTTAGATTAGTGTCGGCCATCTGATTCTGAGAGGC
AATGGACCATGCAGATCAGAAGCCATCTCCACAGTGTCAGGTGAGGAAGCTGCTGTGTGCTCAGTTGCTCTGATTAGTGTCGGCACAGAAGCAGTCTCTGTTTCCACACTGCCTCCAGAGTCGGT
AGTCACCGGGAAGCTGGGCAGGCAGAGGCACCGTCCAGAAGCTCGAAGCTCGAAGTGGCCACAGGAGGAAGTGGCAGAGCAGTCTCTGTTTCCACCTGCACCCTCAGGAAGTCGCC
CGCCCCAGGACAGCAGGACGAGCCACCCTTCAAGGACACATTGTGACCTTCAAGGACACATTGAATAAATGCTGAGGGGACACAAAAAAAAAAAAAAAAAAAA
AAAAAAAAAAAAAAAAAAAAAA

FIG. 8H
```

```
abc1   CMEEEPTHLRLGVSIQNLVKVYRDGMK--VAVDGLALNFYEGQITSFLGHNGAGKTTTMSILTGLFPPTSGTAYILGK      989
abc2   -MEEEPTHLPLVVCVDKLTKVYKNDKK--LALNKLSLNLYENQVVSFLGHNGAGKTTTMSILTGLFPPTSGSATIYGH       90
hABC3  YFEAEPEDLVAGIKIKHLSKVFRVGNKDRAAVRDLNLNLYEGQITVLLGHNGAGKTTTLSMLTGLFPPTSGRAYISGY      575
        *                 *   .                   *  *****************.*.********* abc1   DIRSEMSSIRQNLGVCPQHNVLFDMLTVEEHIWFYARLKGLSEKHVKAEMEQMALDVGLPPSKLKSKTSQLSGGMQRK     1067
abc2   DIRTEMDEIRKNLGMCPQHNVLFDRLTVEEHLWFYSRLKSMAQEEIRKETDKMIEDLELS-NKRHSLVQTLSGGMKRK      167
hABC3  EISQDMVQIRKSLGLCPQHDILFDNLTVAEHLYFYAQLKGLSRQKCPEEVKQMLHIIGLE-DKWNSRSRFLSGGMRRK      652
        .*  *   *:*.** ***:.:** ***.**::**: **. ::.                   .   .*****:**

abc1   LSVALAFVGGSK VVILDEPTAGVDPYSRRGIWELLLKYRQGRTIILSTHHMDEADILGDRIAIISHGKLCCVGSSLFL    1145
abc2   LSVAIAFVGGSF AIILDEPTAGVDPYARRAIWDLILKYRPGRTILLSTHHMDEADLLGDRIAIISHGKLKCCGSPLFL     245
hABC3  LSIGIALIAGSK VLILDEPTSGMDAISRRAIWDLLQRQKSDRTIVLTHFMDEADLLGDRIAIMAKGELQCCGSSLFL      538
        **  :* :.  ::****:*:* * *.**:*::*:  .**::*:*:****:****:: :*: *..* abc1   KNQLGTGYYILTLVKKDVESSLSSCRNSSTVSCLKKEDSVSQSSSDAGLGSDHESDTLTIDVSA SNLIRKHVSEARL     1223
abc2   KGAYXDGYRLTLVKQPAEPGTSQEPGLASSPSGCPRLSSCSEPQ-----------------   VSQFIRKHVASSLL      303
hABC3  KQKYGAGYHMTLVKEPHCNPED-----------------------------------------   ISQLVHHHVPNATL      766
        *          *:**:                                                 .*::::**.::

abc1   VEDIGHELTVLPYEAAKEGAFVELFHEIDDRLSDLGISSYGISETTLEEIFLKVAEE-------SGVDAETSDG-TLP     1294
abc2   VSDTSTELSYILPSEAVKKGAFERLFQQLEHSLDALHLSSFGLMDTTLEEVFLKVSEEDQSLENSEADVKESRKDVLP      380
hABC3  ESSAGAELSFILPRESTHR--FEGLFAKLEKKQKELGIASFGASITTMEEVFLRVGKLVD----SSMDIQAIQLPALQ      838
        *. . **: :**     .  :* **    :. * : :*       *:***:**  :         .:   :* *

FIG. 9A
```

```
abc1  ARRNRRAFG---------------DKQSCLHPFTEDDAVDPND----SDIDPESR-ETDLLSGMD---------------              1339
abc2  GAEGLTAVGGQAGNLARCSELAQSQASLQSASSVGSARGEEGTGYSDGYGDYRPLFDNLQDPDNVSLQEAEMEALAQV                 459
hABC3 YQHERRASD---------------WAVDSNLCGAMDPSD--GIGALIEEER-------------------------                  872
          *                                  .                 .

abc1  GKGSYQLKGWKLTQQQFVALLWKRLLIARRSRKGFFAQIVLPAVFVCIALVFSLIVPPFGKYPSLELQPWMYNEQYTF                 1417
abc2  GQGSRKLEGWWLKMRQFHGLLVKRFHCARRNSKALCSQILLPAFFVCVAMTVALSVPEIGDLPPLVLSPSQYHNYTQP                 537
hABC3 -TAVKLNTGLALHCQQFWAMFLKKAAYSWREWKMVAAQVLVPLTCVTLALLAINYSSELFDDPMLRLTLGEYGRTVVP                 949
         *  *     *      *     * .**        * . . *  *.  ..*. .   ..             * abc1  VSNDAP----------------EDMGTQELLNALTKDPGFGTRCMEGNP-----IPDTPCLAGEE-----DWTISPVPQS              1471
abc2  RGNFIPYANEERQEYRLRLSPDASPQQLVSTFRLPSGVGATCVLKSPANGSLGPMLNLSSGESRLLAARFFDSMCLES                 615
hABC3 FS--VP----------------GTSQLGQQLS--------------------------------------------EHLK              967
       *                                                                          * abc1  IVDLFQNGNWTMKNPSPACQCS------SDKIKKMLPVCPPGAGGLPPPQRKQTADILQNLTGRNISDYLVKTYVQIIA               1545
abc2  FTQGLPLSNFVPPPPSPAPSDSPVXPDEDSLQAWNMSLPPTAG--PETWTSAPSLPRLVHEPVRCTCSAQTGFSCPSS                 692
hABC3 DALQAE---------------GQE------------------------------------PREVLGDLEEFLIFRASVEGGGFNERCLVA    1006
                                                                       * abc1  KS-LKNKIWVNEFRYGGFSLGVSNSQALPPSHEVNDAIKQMKKLLKLTKDTSADRFLSSLGRFMAGLDTKNNVKVWFNN                 1623
abc2  VGGHPPQMRVVTGDILTDITGHNVSEYLLFTSDRFRLHRYGAITFGNVQKSIPASFGARVPPMVRKIAVRRVAQVLYNN                 771
hABC3 AS------------------------------------------------------------------FRDVGERTVVNALFNN          1024
                                                                                       .  **

abc1  KGWHAISSFLNVINNAILRANLQKGE-NPSQYGITAFNHPLNLTKQQLSEVALMTTSVDVLVSICVIFAMSFVPASFVV                 1701
abc2  KGYHSMPTYLNSLNNAILRANLPKSKGNPAAYXITVTNHPMNKTSASLSLDYLLQG-TDVVIAIFIIVAMSFVPASFVV                 849
hABC3 QAYHSPATALAVVDNLLFKLLCGPHA------SIVVSNFPQPRSALQAAKDQFNEGRKGFDIALNLLFAMAFLASTFSI                 1097
       * *    .      ** ***      .     * ..**          *.   .  * .** **.***.

FIG. 9B
```

```
abc1   FLIQERVSKAKHLQFISGVKPVIYWLSNFVWDMCNYVVPATLVIIIFICFQQKSYVSSTNLPVLALLLLLYGWSITPLM  1780
abc2   FLVAEKSTKAKHLQFVSGCNPVIYWLANYVWDMLNYLVPATCCVIILFVFDLPAYTSPTNFPAVLSLFLLYGWSITPIM   928
hABC3  LAVSERAVQAKHVQFVSGVHVASFWLSALLWDLISFLIPSLLLLVVFKAFDVRAFTRDGHMADTLLLLLLYGWAIIPLM  1176
       .  .*..**.          .         *   .  .. .  *.    .     *.*****.*.**.* abc1   YPASFVFKIPSTAYVVLTSVNLFIGINGSVATFVLELFTNNK-LNDINDILKSVFLIFPHFCLGRGLIDMVKN------  1852
abc2   YPASFWFEVPSSAYVFLIVINLFIGITATVATFLLQLFEHDKDLKVVNSYLKSCFLIFPNYNLGHGLMEMAYN------  1001
hABC3  YLMNFFFLGAATAYTRLTFNILSGIATFLMVTIMRIPAVKL--EELSKTLDHVFLVLPNHCLGMAVSSFYENYETRRYC  1254
       *     *   ..  .  ... .  ..         .      .. **. *.. *                 * abc1   ------------------QAMADALERFGE-NRFVSPLSWDL--VGRNLFAMAVEGVVFFLITVLIQYRFFIRPR----------PVKAKLP  1913
abc2   ------------------EYINEYYAKIGQFDKMKSPFEWDI--VTRGLVAMTVEGFVGFFLTIMCQYNFLRQPQ----------RLPVSTK  1063
hABC3  TSSEVAAHYCKKYNIQYQENFYAWSAPGVGRFVASMAASGCAYLILLFLIETNLLQRLRGILCALRRRTLTELYTRMP  1333
                            *            *    *   *  .  * .  **. .* *.  ** .*                   .

abc1   PLNDEDEDVRRERQRILDGGGQ----NDILEIKELTKIYRRK---RKPAVDRICIGIP-PGECFGLLGVNGAGKSTTFKM  1985
abc2   PVED-DVDVASERQRVLRGDAD----NDMVKIENLTKVYKSRKIGRILAVDRLCLGVCVPGECFGLLGVNGAGKTSTFKM  1138
hABC3  VLPE-DQDVADERTRILAPSPDSLLHTPLIIKELSKVYEQR---VPLLAVDRLSLAVQ-KGECFGLLGFNGAGKTTFKM  1408
         *    *    * *.*            ..****. *...        ***   *   ***** *.*** abc1   LTGDTPVTRGDAFLNKNSILSNIHEVHQNMGYCPQFDAITELLTGREHVEFFALLRGVPEKEVGKFGEWAIRKLGLVKY  2064
abc2   LTGDESTTGGEAFVNGHSVLKDLLQVQQSLGYCPQFDVPVDELTAREHLQLYTRLRCIPWKDEAQVVKWALEKLELTKY  1217
hABC3  LTGEESLTSGDAFVGGHRISSDVGKVRQRIGYCPQFDALLDHMTGREMLVMYARLRGIPERHIGACVENTLRGLLEPH  1487
       ***    . * ** .   .    .    .  *******          ***.     *          .   *    *

FIG. 9C
```

```
abc1  GEKYASNYSGGNKRKLSTAMALIGGPPVVFLDEPTTGMDPKARRFLWNCALSIVKEGRSVVLTSHSMEECEALCTRMAI  2143
abc2  ADKPAGTYSGGNKRKLSTAIALIGYPAFIFLDEPTTGMDPKARRFLWNLILDLIKTGRSVVLTSHSMEECEALCTRLAI  1296
hABC3 ANKLVRTYSGGNKRKLSTGIALIGEPAVIFLDEPSTGMDPVARRLLWDTVARARESGKAIITSHSMEECEALCTRLAI   1566
       *    .   ********* .*****  ********.******.*** *** ** *    .    *****************.**

abc1  MVNGRFRCLGSVQHLKNRFGDGYTIVVRIAGSNP--DLKPVQEFFGLAFPGSVLKEKHRNMLQYQLPSSLSSLARIFSI  2220
abc2  MVNGRLHCLGSIQHLKNRFGDGYMITVRTKSSQ---NVKDVVRFFNRNFPEAHAQGKTPYKVQYQLKSEHISLAQVFSK  1372
hABC3 MVQGQFKCLGSPQHLKSKFGSGYXLRAKVQSEGQQEALEEFKAFVDLTFPGSVLEDEHQGMVHYHLPGRDLSWAKVFGI  1645
      . .  .  *  *   . .             *                . *   .    *   * abc1  LSQSKKRLHIEDYSVSQTTLDQVFVNFAKDQSDDD----------HLKDLSLHKN-QTVVDVAVLTS------------  2276
abc2  MEQVVGVLGIEDYSVSQTTLDNVFVNFAKKQSDNVEQQEAEPSSLPSPLGLLSLLRPRPAPTELRALVADEPEDLDTED  1451
hABC3 LEKAKEKYGVDDYSVSQISLEQVFLSFAHLQPPTAEEGR---------------------------------------  1684
         .     ..******  .* ... *  *  ** abc1  -----FLQDEKVKESYV-----  2288
abc2  EGLISFEEERAQLSFNTDTLC  1472
hABC3 ---------------------
```

FIG. 9D

```
GGCGGCTAGCGGCGGAGGCCCCTTCCTGTACTTCAGGGATCGGCCACCATGTCCCACCGGAAGTTTTCCGCCCCTCGGCACGGACACCTGGGCTTCCTGC      100
                                           M  S  H  R  K  F  S  A  P  R  H  G  H  L  G  F  L        17

CCCATAAGAGGAGCCACCGGCACCGGGACGTGGCCCGGCAAGGTGAAGACTGGCCCCGTGCACCTCACGGCCTTCCTGGGCTACAAGGC            200
 P  H  K  R  S  H  R  H  R  G  K  V  K  T  W  P  R  D  D  P  S  Q  P  V  H  L  T  A  F  L  G  Y  K  A    51

GGGCATGACCCACACCCTGCGCGAGGTGCACCGGCCTCAAAATTCCAAAGGGAGGAGGTGACAATTGTAGAAACGCCCCTA            300
 G  M  T  H  T  L  R  E  V  H  R  P  G  L  K  I  S  K  R  E  E  V  E  A  V  T  I  V  E  T  P  P  L     84

GTGGTGGTGGGCGTGGTGGGCTACGTGGCCACCCCTCGAGGTCTCCGGAGCTTCAAGACCATCTTTGCAGAACACCTCAGTGATGAGTGCCGGCGCGAT      400
 V  V  G  V  V  G  Y  V  A  T  P  R  G  L  R  S  F  K  T  I  F  A  E  H  L  S  D  E  C  R  R  R       117

TCTACAAGGACTGGCACAAGAGCAAGAAGAAGAAGGCCTTCACCAAGGCCTGCAAGAGGTGGCGGGACACAGACGGGAAAAAGCAGCTACAGAAGGACTTCGC      500
 F  Y  K  D  W  H  K  S  K  K  K  K  A  F  T  K  A  C  K  R  W  R  D  T  D  G  K  K  Q  L  Q  K  D  F  A  151

CGCCATGAAGAAGTACTGCAAGGTCATTCGAGTCATTGTGCACACTCAGATGAAACTCCTGCCCTTCCGGCAGAAGGCCCACATCATGGAGATCCAG      600
 A  M  K  K  Y  C  K  V  I  R  V  I  V  H  T  Q  M  K  L  L  P  F  R  Q  K  K  A  H  I  M  E  I  Q     184

CTGAACGGTGGCACGGTTGCGGAGAAGGTGGCCCAGGCCCGGCTGGAGAAGCAGGTGCCCGTGCACAGCGTGTTCAGCCAGAGTGAGGTCATTG      700
 L  N  G  G  T  V  A  E  K  V  A  W  A  Q  A  R  L  E  K  Q  V  P  V  H  S  V  F  S  Q  S  E  V  I     217

ATGTCATTGCTGTCACCAAGGGTCGAGGCGTCAAAGGGGTCACAAGCCGCTGGCATACCAAGAAGCTGCCGCGGAAGACCCATAAGGGCCTGCGCAAGGT      800
 D  V  I  A  V  T  K  G  R  G  V  K  G  V  T  S  R  W  H  T  K  K  L  P  R  K  T  H  K  G  L  R  K  V   251
```

FIG. 11A

```
GGCCTGCATTGGGCCTGGCCACCCCGCTGGCGCGTGTGGGCTGCTCCATTGCTCGGGCCAGAGGGCTATCACCACCGCACGGAGCTCAACAAGAAGATC      900
 A  C  I  G  A  W  H  P  A  R  V  G  C  S  I  A  R  A  G  Q  K  G  Y  H  H  R  T  E  L  N  K  K  I      284

TTCCGCATCGGGCGCCCACTACGGGGAAGTGAACAACGACTTCGTCATGCTGAAGGGTGTTATTGCTGGTACCAAGAAGCGGGTCATTACGCTGAGAAAGTCCCT     1000
 F  R  I  G  R  G  P  H  M  E  D  G  K  L  V  K  N  N  A  S  T  S  Y  D  V  T  A  K  S  I  T  P  L      317

GTGGCTTCCCCACTACGGGGAAGTGAACAACGACTTCGTCATGCTGAAGGGTTGTATTGCTGGTACCAAGAAGCGGGTCATTACGCTGAGAAAGTCCCT     1100
 G  F  P  H  Y  G  E  V  N  N  D  F  V  M  L  K  G  C  I  A  G  T  K  K  R  V  I  T  L  R  K  S  L      351

CCTGGTGCATCACAGTCGCCAAGCCGTGGAGAATATTGAGCTCAAGTTCATTGACACCACCTCCAAGTTCGGCCATGGCCGCTTCCAGACAGCCCAAGAG     1200
 L  V  H  H  S  R  Q  A  V  E  N  I  E  L  K  F  I  D  T  T  S  K  F  G  H  G  R  F  Q  T  A  Q  E      384

AAGAGGGCCTTCATGGGCCCCCAAATGAAGAAGCATCTGAGAAAGGAAACCCCGGAGACTGTAGGCTGTGTGGGTGATGAACCCTGAAGC             1300
 K  R  A  F  M  G  P  P  Q  K  K  H  L  E  K  E  T  P  E  T  S  G  D  L  *                              407

GCACCGGACTGTCTGCCCCAATGTCTAACAAAGGCCGAGGCGACTCTTCCTGCGAGTCTCAGAGCGCTGTGTAACGCCCAAGGGGTTCACCTTGCCT     1400

GCTGCCTAGACAAAGCCGATTCATTAAGACAGGGGAATTGCAATAGAAAGAGTAATTCACACGAGCTGGCGCTGTGCGGGAGACCGAGTTTATGTTT     1500

TATTATTACTCAAATCGATCTCTTTGAGCAAAAAAAAAAAAAAAAAAAAAA                                                    1548
```

FIG. 11B

| | |
|---|---|
| HUMAN L3 | MSHRKFSAPRHGSLGFLPRKRSSRHRGKVKSFPKDDPSKPVHLTAFLGYK |
| BOVINE L3 | ----------------------------S------------- |
| MURINE L3 | ----------------------------A------------- |
| SEM L3 | --------H-----H---H------TW-R----Q--------- |

| | |
|---|---|
| HUMAN L3 | AGMTHIVREVDRPGSKVNKKEVVEAVTIVETPPMVVVGIVGYVETPRGLR |
| BOVINE L3 | ----------------------------I------------- |
| MURINE L3 | ------------------------------------------- |
| SEM L3 | -----TL---H---L-IS-R-E----------L----V----A------ |

| | |
|---|---|
| HUMAN L3 | TFKTVFAEHISDECKRRFYKNWHKSKKKAFTKYCKKWQDEDGKKQLEKDF |
| BOVINE L3 | ----I--------------------------A-------R-- |
| MURINE L3 | -------------------------------DT--------- |
| SEM L3 | S---I----L----R-----D----------A--R-R-T------Q--- |

| | |
|---|---|
| HUMAN L3 | SSMKKYCQVIRVIAHTQMRLLPLRQKKAHLMEIQVNGGTVAEKLDWARER |
| BOVINE L3 | ---------------V------------------------ |
| MURINE L3 | N----------I---------------------------- |
| SEM L3 | AA-----K-----V----K---F------I----L--------VA--QA- |

| | |
|---|---|
| HUMAN L3 | LEQQVPVNQVFGQDEMIDVIGVTKGKGYKGVTSRWHTKKLPRKTHRGLRK |
| BOVINE L3 | ------------------------------------------- |
| MURINE L3 | -------S----------------------------------- |
| SEM L3 | --K----HS--S-S-V----A----R-V-----------------K---- |

| | |
|---|---|
| HUMAN L3 | VACIGAWHPARVAFSVARAGQKGYHHRTEINKKIYKIGQGYLIKDGKLIK |
| BOVINE L3 | ------------------------------------------- |
| MURINE L3 | --------------T---------------------------- |
| SEM L3 | -------------GC-I------------L----FR--R-PHME----V- |

| | |
|---|---|
| HUMAN L3 | NNASTDYDLSDKSINPLGGFVHYGEVTNDFVMLKGCVVGTKKRVLTLRKS |
| BOVINE L3 | ------------------------------------------- |
| MURINE L3 | ---------------------------I--------------- |
| SEM L3 | -----S--VTA---T-----P-----N---------IA----I----- |

| | |
|---|---|
| HUMAN L3 | LLVQTKRRALEKIDLKFIDTTSKFGHGRFQTMEEKKAFMGPLKKDRIAKE |
| BOVINE L3 | ---------------------------V-------------- |
| MURINE L3 | ------------------------------------------- |
| SEM L3 | ---HHS-Q-V-N-E------------AQ--R-----Q--HLEKET |

| | |
|---|---|
| HUMAN L3 | EGA---- |
| BOVINE L3 | ------- |
| MURINE L3 | ------- |
| SEM L3 | PETSGDL |

FIG. 12

```
          10                20                30                40                50                60                70
CGG GAC ACC AAG TTT AGG GAG GAC TGC CCG GAT CGC CCG GAG GAA CTG GGC CGC CAC AGC TGG GCT GTC CTC
 R   D   T   K   F   R   E   D   C   P   D   R   P   E   E   L   G   R   H   S   W   A   V   L 80                90               100               110               120               130               140
CAC ACC CTG GCC GCC TAC TAC CCC GAC CTG CCC ACC CCA GAA CAG CAG GAC ATG GCC CAG TTC ATA CAT
 H   T   L   A   A   Y   Y   P   D   L   P   T   P   E   Q   Q   D   M   A   Q   F   I   H 150               160               170               180               190               200               210
TTA TTT TCT AAG TTT TAC CCC TGT GAG GAG TGT GCT GAA GAC CTA AGA AAA AGG CTG TGC AGG AAC CAC CCA
 L   F   S   K   F   Y   P   C   E   E   C   A   E   D   L   R   K   R   L   C   R   N   H   P 220               230               240               250               260               270               280
GAC ACC CGC ACC CGG ACA TGC TTC ACA CAG TGG CTG TGC CAC AAT GAA GTG AAC CGC AAG CTG GGC
 D   T   R   T   R   T   C   F   T   Q   W   L   C   H   N   E   V   N   R   K   L   G 290               300               310               320               330               340               350
AAG CCT GAC TTC GAC TGC TCA AAA GTG GAT GAG CGC TGG GAC GGC TGG AAG GAT GCC TCC TGT GAC TAG
 K   P   D   F   D   C   S   K   V   D   E   R   W   D   G   W   K   D   G   S   C   D  *

360               370               380               390               400               410               420               430               440
AGGGT GGTCA GCCAG AGCTC ATGGG ACAGC TAGCC AGGCA TGGTT GGATA GGGGC AGGGC ACTCA TTAAA GTGCA TCACA 450               460
GCCAG AAAAA AAAAA AAAAA AAAAA AAAAA AAA
```

FIG. 13

```
rALR    1  MRTQQKRDIKFREDCPQDREELGRNTWAFLHTLAAYYPDMPTPEQQQDMAQFIHIFSKFY
hALR       ------RDTKFREDCPPDREELGRHSWAVLHTLAAYYPDLPTPEQQQDMAQFIHLFSKFY
                  **** ********.. **********.****.* rALR   61  PCEECAEDIRKRIDRSQPDTSTRVSFSQWLCRLHNEVNRKLGKPDFDCSRVDERWRDGWK
hALR       PCEECAEDLRKRLCRNHPDTRTRACFTQWLCHLHNEVNRKLGKPDFDCSKVDERWRDGWK
           ******.*. *..*.. .*.**************.******** rALR  121  DGSCD
hALR       DGSCD
           *****
```

FIG. 14

# HUMAN CHROMOSOME 16 GENES, COMPOSITIONS, METHODS OF MAKING AND USING SAME

This application claims benefit of provisional Appln 60/000,596 filed Jun. 30, 1995.

ACKNOWLEDGEMENT

This invention was made in part with Government support under Grant No. DK44853, from the National Institutes of Health. The Government may have certain rights in this invention.

BACKGROUND OF THE INVENTION

The assembly of contiguous cloned genomic reagents is a necessary step in the process of disease-gene identification using a positional cloning approach. The rapid development of high density genetic maps based on polymorphic simple sequence repeats has facilitated contig assembly using sequence tagged site (STS) content mapping. Most contig construction efforts have relied on yeast artificial chromosomes (YACs), since their large insert size uses the current STS map density more advantageously than bacterial-hosted systems. This approach has been validated for multiple human chromosomes with YAC coverage ranging from 65–95% for many chromosomes and contigs of 11 to 36 Mb being described (Chumakov et al., Nature 377 (Supp.):175–297, 1995; Doggett et al., Nature 377 (Supp.):335–365, 1995b; Gemmill et al., Nature 377 (Supp.):299–319, 1995; Krauter et al., Nature 377 (Supp.):321–333, 1995; Shimizu et al., Cytogenet. Cell Genet. 70:147–182, 1995; van-Heyningen et al., Cytogenet. Cell Genet. 69:127–158, 1995).

Despite numerous successes, the YAC cloning system is not a panacea for cloning the entire genome of complex organisms due to intrinsic limitations that result in substantial proportions of chimeric clones (Green et al., Genomics 11:658–669, 1991; Bellanne-Chantelot et al., Cell 70:1059–1068, 1992; Nagaraja et al., Nuc. Acids Res. 22:3406–3411, 1994), as well as clones that are rearranged, deleted or unstable (Neil et al., Nuc. Acids Res. 18:1421–1428, 1990; Wada et al., Am. J. Hum. Genet. 46:95–106, 1990; Zuo et al., Hum. Mol. Genet. 1:149–159, 1992; Szepetowski et al., Cytogenet. Cell Genet. 69:101–107, 1995). At least some of these cloned artifacts are a product of the recombinational machinery of yeast acting on the various types of repetitive elements in mammalian DNA (Neil et al., supra. 1990; Green et al., supra. 1991; Schlessinger et al., Genomics 11:783–793, 1991; Ling et al., Nuc. Acids Res. 21:6045–6046, 1993; Kouprina et al., Genomics 21:7–17, 1994; Larionov et al., Nuc. Acids Res. 22:4154–4162, 1994).

Accordingly, alternative cloning systems must be used in concert with YAC-based approaches to complement localized YAC cloning deficiencies, to enhance the resolution of the physical map, and to provide a sequence-ready resource for genome-wide DNA sequencing. Several exon trapping methodologies and vectors have been described for the rapid and efficient isolation of coding regions from genomic DNA (Auch et al., Nuc. Acids Res. 18:6743–6744, 1990; Duyk et al., Proc. Natl. Acad. Sci., USA 87:8995–8999, 1990; Buckler et al., Proc. Natl. Acad. Sci., USA 88:4005–4009, 1991; Church et al., Nature Genet. 6:98–105, 1994). The major advantage of exon trapping is that the expression of cloned genomic DNAs (cosmid, P1 or YAC) is driven by a heterologous promoter in tissue culture cells. This allows for coding sequences to be identified without prior knowledge of their tissue distribution or developmental stage of expression. A second advantage of exon trapping is that exon trapping allows for the identification of coding sequences from only the cloned template of interest, which eliminates the risk of characterizing highly conserved transcripts from duplicated loci. This is not the case for either cDNA selection or direct library screening.

Exon trapping has been used successfully to identify transcribed sequences in the Huntington's disease locus (Ambrose et al., Hum. Mol. Genet. 1:697–703, 1992; Taylor et al., Nature Genet. 2:223–227, 1992; Duyao et al., Hum. Mol. Genet. 2:673–676, 1993) and BRCA1 locus (Brody et al., Genomics 25:238–247, 1995; Brown et al., Proc. Natl. Acad. Sci., USA 92:4362–4366, 1995). In addition, a number of disease-causing genes have been identified using exon trapping, including the genes for Huntington's disease (The Huntington's Disease Collaborative Research Group, Cell 72:971–983, 1993), neurofibromatosis type 2 (Trofatter et al., Cell 72:791–800, 1993), Menkes disease (Vulpe et al., Nature Genet. 3:7–13, 1993), Batten Disease (The International Batten Disease Consortium, Cell 82:949–957, 1995), and the gene responsible for the majority of Long-QT syndrome cases (Wang et al., Nature Genet. 12:17–23, 1996).

A 700 kb CpG-rich region in band 16p13.3 has been shown to contain the disease gene for 90% of the cases of autosomal dominant polycystic kidney disease (PKD1) (Germino et al., Genomics 13:144–151, 1992; Somlo et al., Genomics 13:152–158, 1992; The European Polycystic Kidney Disease Consortium, Cell 77:881–894, 1994) as well as the tuburin gene (TSC2), responsible for one form of tuberous sclerosis (The European Chromosome 16 Tuberous Sclerosis Consortium, Cell 75:1305–1315, 1993). An estimated 20 genes are present in this region of chromosome 16 (Germino et al., Kidney Int. Supp. 39:S20–S25, 1993). Characterization of the region surrounding the PKD1 gene in 16p13.3, however, has been complicated by duplication of a portion of the genomic interval more proximally at 16p13.1 (The European Polycystic Kidney Disease Consortium, supra. 1994).

This chromosomal segment serves as a challenging test for large-insert cloning systems in E. coli and yeast since it resides in a GC-rich isochore (Saccone et al., Proc. Natl. Acad. Sci., USA 89:4913–4917, 1992) with an abundance of CpG islands (Harris et al., Genomics 7:195–206, 1990; Germino et al., supra. 1992), genes (Germino et al., supra. 1993) and Alu repetitive sequences (Korenberg et al., Cell 53:391–400, 1988). Chromosome 16 also contains more low-copy repeats than other chromosomes with almost 25% of its cosmid contigs hybridizing to more than one chromosomal location when analyzed by fluorescence in situ hybridization (FISH) (Okumura et al., Cytogenet. Cell Genet. 67:61–67, 1994). These types of repeats and sequence duplications interfere with "chromosome walking" techniques that are widely used for identification of genomic DNA and pose a challenge to hybridization-based methods of contig construction. This is because these techniques rely on hybridization to identify clones containing overlapping fragments of genomic DNA; thus, there is a high likelihood of "walking" into clones derived from homologues instead of clones derived from the authentic gene. In a similar manner, the sequence duplications and chromosome 16-specific repeats also interfere with the unambiguous determination of a complete cDNA sequence that encodes the corresponding protein. Furthermore, low copy repeats may lead to instability of this interval in bacteria, yeast and higher eukaryotes.

Thus, there is a need in the art for methods and compositions which enable accurate identification of genomic and cDNA sequences corresponding to authentic genes present on highly repetitive portions of chromosome 16, as well as genes similarly situated on other chromosomes.

SUMMARY OF THE INVENTION

In accordance with the present invention, there are provided isolated nucleic acids encoding a human netrin, a human ATPase binding cassette transporter, a human ribosomal L3 subtype, and a human augmenter of liver regeneration.

The present invention further provides isolated protein products encoded by a human netrin gene, a human ATPase binding cassette transporter gene, a human ribosomal L3 gene, and a human augmenter of liver regeneration geney.

Additionally, the present invention provides nucleic acid probes that hybridize to invention nucleic acids as well as isolated nucleic acids comprising unique gene sequences located on chromosome 16.

Further provided are vectors containing invention nucleic acids as well as host cells transformed with invention vectors.

Transgenic non-human mammals that express invention polypeptides are provided by the present invention.

The present invention includes antisense oligonucleotides, antibodies and compositions containing same.

Additionally, the invention provides methods for identifying compounds that bind to invention polypeptides. Such compounds are useful for modulating the activity of invention polypeptides.

BRIEF DESCRIPTION OF THE DRAWINGS

FIG. 2 shows an alignment of selected exon traps with sequences in the databases. An alignment of sequences encoded by exon trap L48741 (SEQ ID NO:1) and N-acetylglucosamine-6-phosphate deacetylase from C. elegans (SEQ ID NO:2), E. coli (SEQ ID NO:3) and Haemophilus (SEQ ID NO:4). The EGF repeat from netrin-1 (SEQ ID NO:7), netrin-2 (SEQ ID NO:6) and UNC-6 (SEQ ID NO:8) are shown aligned to one of the translated netrin-like exon trap (Genbank Accession No. L75917) (SEQ ID NO:5). An alignment of sequences from the second netrin-like exon trap (Genbank Accession No. L75916) (SEQ ID NO:9) and netrin-1 (SEQ ID NO:11 and netrin-2 (SEQ ID NO:10) is shown. An alignment of the translated Rab26-like RT-PCR product (Genbank Accession Nos. L48770-L48771) (SEQ ID NO:12) and rat Rab26 (SEQ ID NO:13). Sequences encoded by exon trap L48792 (SEQ ID NO:14) are shown aligned to sequences from the pilB transcriptional repressor from Neisseria gonorrhoeae (SEQ ID NO:15), sequences predicted by computer analysis to be encoded by cosmid F44E2.6 from C. elegans (SEQ ID NO:17), the YCL33C gene product from yeast (Genbank Accession No. P25566) (SEQ ID NO:16), and a transcriptional repressor from Haemophilus (SEQ ID NO:18). Periods denote positions where gaps were inserted in the protein sequence in order to maintain alignment.

FIG. 3 shows 6803 bp of hNET genomic sequence from P1 clone 53.8B (SEQ ID NO:19).

FIG. 4 shows 1743 bp of hNET cDNA (SEQ ID NO:20) coding for the human homologue of the chicken netrin-2 gene.

FIG. 5 shows an amino acid comparison between chicken netrin-1 (SEQ ID NO:22), chicken netrin-2 (SEQ ID NO:23) and the human homologue of netrin-2, hNET (SEQ ID NO:21). Shaded boxes denote regions of identical homology. The laminin domains V and VI and the C-terminal domain (C) are indicated by arrows with domain V divided into three sub-components (V-1 to V-3). The asterisks identify a motif for adhesion/signaling receptors.

FIG. 6 shows a graphical representation of the homology between domains of chicken netrin-1, chicken netrin-2 and the human homologue of netrin-2, hNET.

FIG. 8 shows 5.8 kb of cDNA encoding hABC3 (SEQ ID NO:24).

FIG. 9 shows an amino acid alignment of murine ABC1 (SEQ ID NO:26) and ABC2 (SEQ ID NO:27) with hABC3 (SEQ ID NO:25). Hyphens denote gaps; asterisks denote identical residues, while periods denote conservative substitutions. The location of the ATP binding cassettes is shown by the boxed regions. Numbers at the right show the relative position of the proteins.

FIG. 11 shows the nucleotide and deduced amino acid sequence of the SEM L3 cDNA (SEQ ID NO:28 & 29), respectively. The 5' upstream inframe stop codon is underlined and the arrows indicate the site of the polyA tract of the two shorter cDNA clones that were also isolated.

FIG. 12 shows a comparison of the deduced amino acid sequences from human (SEQ ID NO:30), bovine (SEQ ID NO:31), murine (SEQ ID NO:32) and the SEM L3 (SEQ ID NO:29) genes. Dashes indicate sequence identity to the human L3 gene. The nuclear targeting sequence at the N-terminal end is shaded and the bipartite motif is boxed.

FIG. 13 shows the nucleotide and deduced amino acid sequence of the hALR cDNA (SEQ ID NO:33 and 34), respectively.

FIG. 14 shows a comparison of the deduced amino acid sequences from rat ALR (SEQ ID NO:35) and human ALR (SEQ ID NO:34).

DETAILED DESCRIPTION OF THE INVENTION

Figure 1:
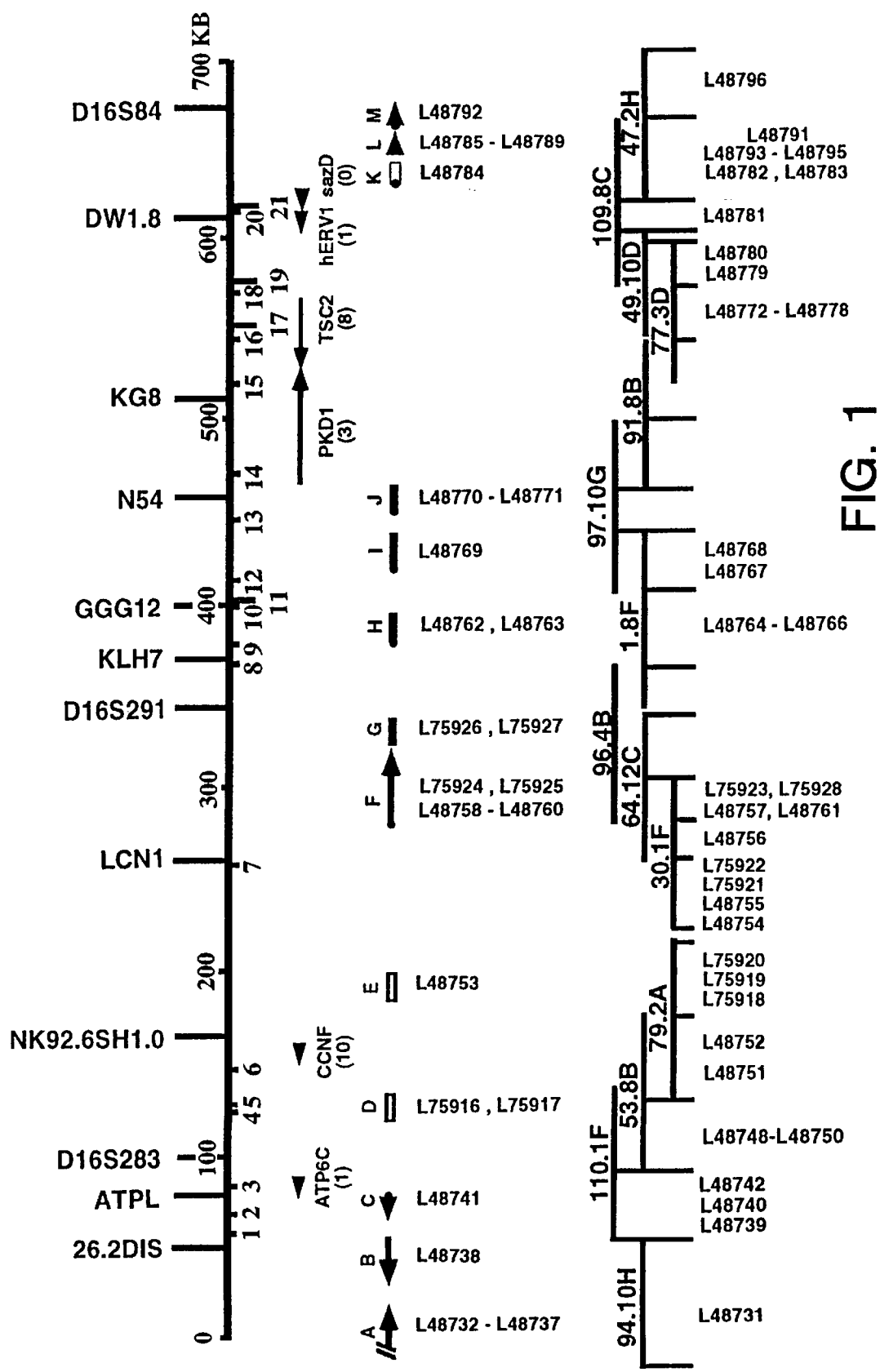
FIG. 1 shows a schematic diagram of the P1 contig and trapped exons. The horizontal line at the top shows the position of relevant DNA markers with the scale (in kilobases). The position of NotI sites is shown below the horizontal line. The position and orientation of the known genes is indicated by arrows with the number of exon traps obtained from each gene shown in parentheses. The position of the transcription units described in this report (A through M) are shown below the known genes. The Genbank Accession numbers of corresponding exon traps are shown below each transcriptional unit. P1 clones are indicated by the overlapping lines with the name of the clone shown above the line. The position of trapped exons which did not map to characterized transcripts are shown below the P1 contig. Vertical lines denote the interval within the P1 clone(s) detected by the exon traps in hybridization studies.
Figure 7:
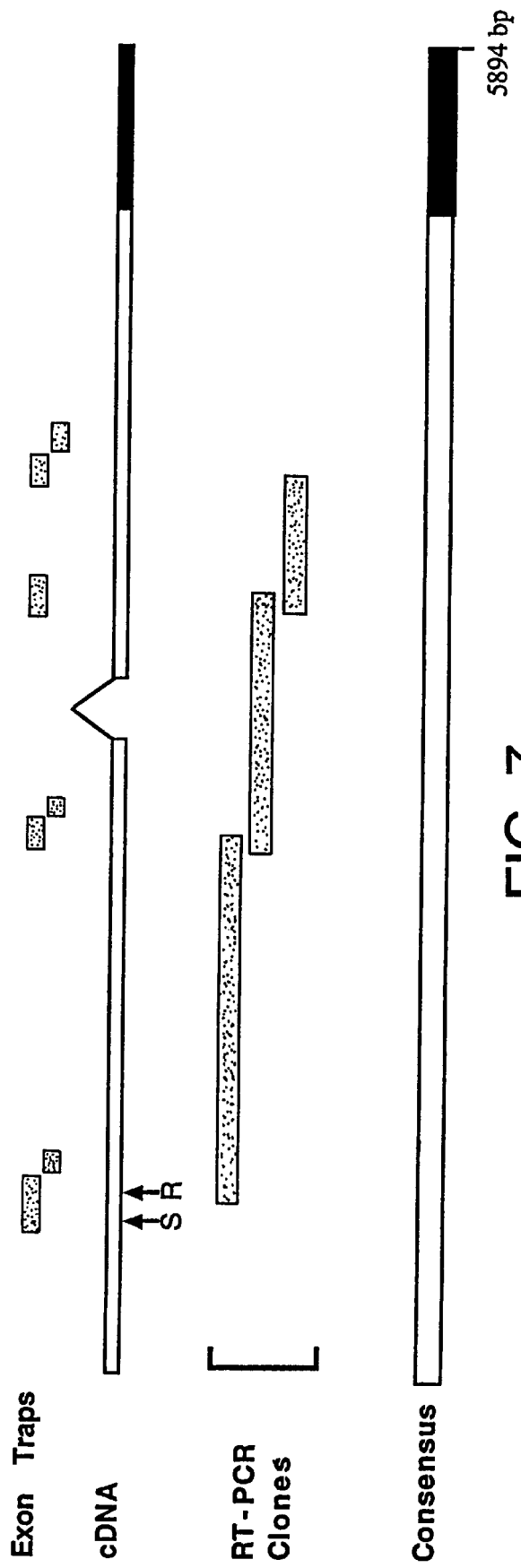
FIG. 7 shows exon traps, RT-PCR products and cDNA from the hABC3 gene. Exon traps are shown above. hABC3 cDNA is shown below the exon traps with the position of the Genetrapper selection (S) and repair (R) oligonucleotides iindicated. The position of the RT-PCR clones are shown below the cDNA. A 147 bp insertion is present in the RT-PCR product relative to the cDNA. This insertion does not disrupt the open reading frame.
Figure 10:
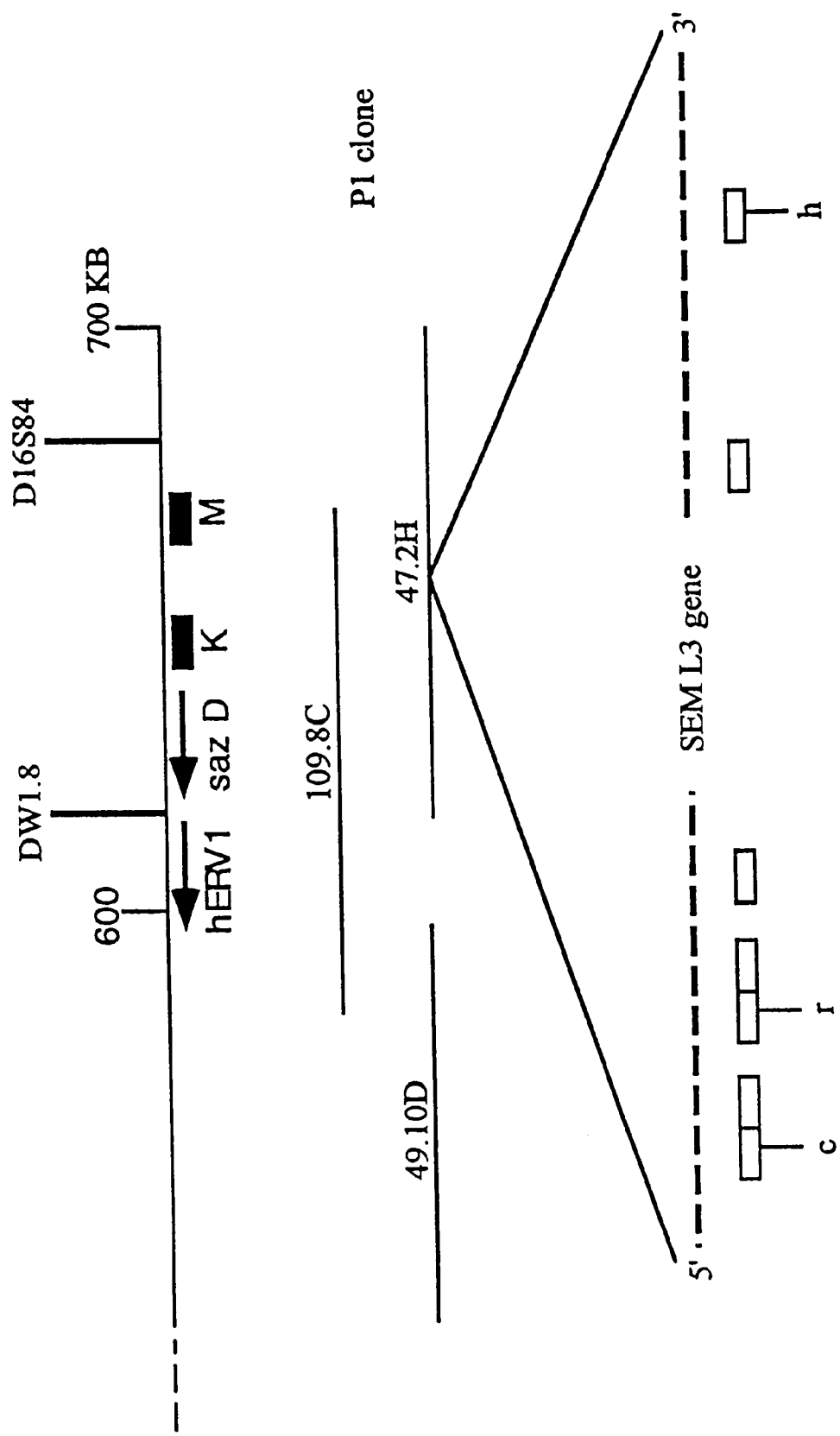
FIG. 10 shows the region of the transcriptional map of the PKD1 locus from which P1 clones 49.1D, 109.8C and 47.2H were isolated. The open boxes represent trapped exons with their relative position indicated below the SEM L3 gene. c, r and h identify the location of the capture, repair and hybridization oligonucleotides, respectively.

All patent applications, patents, and literature references cited in this specification are hereby incorporated by reference in their entirety. In case of conflict or inconsistency, the present description, including definitions, will control.

Definitions:

1. "complementary DNA (cDNA)" is defined herein as a single-stranded or double-stranded intronless DNA molecule that is derived from the authentic gene and whose sequence, or complement thereof, encodes a protein.

2. As referred to herein, a "contig" is a continuous stretch of DNA or DNA sequence, which may be represented by multiple, overlapping, clones or sequences.

3. As referred to herein, a "cosmid" is a DNA plasmid that can replicate in bacterial cells and that accommodates large DNA inserts from about 30 to about 45 kb in length.

4. The term "P1 clones" refers to genomic DNAs cloned into vectors based on the P1 phage replication mechanisms. These vectors generally accommodate inserts of about 70 to about 105 kb (Pierce et al., *Proc. Natl. Acad. Sci., USA*, 89:2056–2060, 1992).

5. As used herein, the term "exon trapping" refers to a method for isolating genomic DNA sequences that are flanked by donor and acceptor splice sites for RNA processing.

6. "Amplification" of DNA as used herein denotes a reaction that serves to increase the concentration of a particular DNA sequence within a mixture of DNA sequences. Amplification may be carried out using polymerase chain reaction (PCR) (Saiki et al., *Science*, 239:487, 1988), ligase chain reaction (LCR), nucleic acid-specific based amplification (NSBA), or any method known in the art.

7. "RT-PCR" as used herein refers to coupled reverse transcription and polymerase chain reaction. This method of amplification uses an initial step in which a specific oligonucleotide, oligo dT, or a mixture of random primers is used to prime reverse transcription of RNA into single-stranded cDNA; this cDNA is then amplified using standard amplification techniques e.g. PCR.

A P1 contig containing approximately 700 kb of DNA surrounding the PKD1 and TSC2 gene was assembled from a set of 12 unique chromosome 16-derived P1 clones obtained by screening a 3 genome equivalent P1 library (Shepherd et al., *Proc. Natl. Acad. Sci., USA* 91:2629–2633, 1994) with 15 distinct probes. Exon trapping was used to identify transcribed sequences from this region in 16p13.3.

96 novel exon traps have been obtained containing sequences from a minimum of eighteen genes in this interval. The eighteen identified genes include five previously reported genes from the interval and a previously characterized gene whose location was unknown (Table I). Additional exon traps have been mapped to genes based on their presence in cDNAs, RT-PCR products, or their hybridization to distinct mRNA species on Northern blots.

TABLE I

Database Homologies

| Gene[a] | Independent Exon Traps[b] | Clone[c] | Transcript Size | Database Homology[d] | Accession Number of Best Hit[e] | P value[f] |
|---|---|---|---|---|---|---|
| A | 6 | 2 kb (cDNA) | 8 kb | Probable protein kinase [*S. cerevisiae*] | Z48149 | 6.3e-83 |
| B | 1 | 1.3 kb (cDNA) | 2.5 | No Significant homology | | |
| C | 1 | 0.55 kb (Exon Trap) 0.6 kb (3' RACE) | 1.4 kb | N-acetylglucosamine-6-phosphate deacetylase [*C. elegans*] | P34480 | 7.4e-73 |
| D | 2 | Exon trap (159 bp) | — | Netrin-2 [*G. gallus*] | B54665 | 3.7e-11 |
|   |   | Exon trap (196 bp) | — | Netrin-2 [*G. gallus*] | B54665 | 6.1e-33 |
| E | 1 | Exon trap (100 bp) | — | ABC1 gene product [*M. musculus*] | P41233 | 0.0047 |
| F | 3 | 1.1 kb (RT-PCR) | 7 kb | ABC2 gene product [*M. musculus*] | P41234 | 3.0e-28 |
|   | 2 | 2.8 kb (cDNA) | 7 kb | ABC1 gene product [*M. musculus*] | P41233 | 7.1e-65 |
| G | 2 | 1.8 kb (cDNA) | 2.5 kb | RNA-Binding protein [*Homo sapiens*] | L37368 | 2.6e-176 |
| H | 2 | 1.2 kb (RT-PCR) | 2.5 kb | phi AP3 [*M. musculus*] | S41688 | 2.9e-169 |
| I | 1 | 0.45 kb (Exon Trap) | 3.0 + 4.5 kb | No significant homologies | | |
| J | 2 | 0.24 kb (RT-PCR) | 2 kb | Rab26 [*R. norvegicus*] | U18771 | 3.6c-56 |
| K | 1 | Exon trap (219 bp) | § | 40S Ribosomal protein S4 [*Homo sapiens*] | P15880 | 7.3e-18 |
| L | 5 | 1.7 kb (cDNA) | 1.6 kb | 60s Ribosomal protein L3 [*Homo sapiens*] | S34195 | 6.7e-233 |
| M | 1 | 0.7 kb (cDNA) | 1.3 kb | Hypothetical 17.2 Kd protein [*C. elegans*] | P34436 | 6.2e-10 |

[a]Gene as denoted in FIG. 1.
[b]Number of the trapped exon present in cloned cDNA or PCR product.
[c]Size of clone with type of clone indicated in parentheses.
[d]Significant homology in databases as determined by BLASTX.
[e]Accession Number of best hit.
[f]Smallest sum probability for the best database match.
— Northern analysis was not performed due to the small size of the exon traps.
§ Up to 200 copies of LLREP3 are present in the genome.

Exon trapping was performed using an improved trapping vector (Burn et al., *Gene* 161:183–187, 1995), with the resulting exon traps being characterized by DNA sequence analysis. In order to determine the relative efficiency of the exon trapping procedure, exon traps were compared to the cDNA sequences for those genes known to be in the interval around the PKD1 gene (FIG. 1). Single exon traps were obtained from the human homologue of the ERV1 (Lisowsky et al., *Genomics* 29:690–697, 1995) and the ATP6C proton pump genes (Gillespie et al., *Proc. Natl. Acad. Sci., USA* 88:4289–4293, 1991).

In contrast, eight individual exon traps were isolated from the TSC2 gene and ten from the CCNF gene (The European Chromosome 16 Tuberous Sclerosis Consortium, supra. 1993; Kraus et al., *Genomics* 24:27–33, 1994). Trapped sequences from three of the exons present in the PKD1 gene were obtained (The American PKD1 Consortium, *Hum. Mol. Genet.* 4:575–582, 1995; The International Polycystic Kidney Disease Consortium, Cell 81:289–298, 1995; Hughes et al., Nature Genet. 10:151–160, 1995). 16 additional exon traps from the 109.8C and 47.2H P1 clones were also obtained.

Sequences present in two exon traps (Genbank Accession Nos. L75926 and L75927), localizing to the region of overlap between the 96.4B and 64.12C P1 clones, were shown to contain sequences from the previously described human homologue to the murine RNPS1 gene (Genbank Accession No. L37368), encoding an S phase-prevalent DNA/RNA-binding protein (Schmidt et al., Biochim. Biophys. Acta 1216:317–320, 1993). A comparison of these exon traps to the dbEST database indicated that they were also contained in cDNA 52161 from the I.M.A.G.E. Consortium (Lennon et al., Genomics 33:151–152, 1996). Based on these data, the hRNPS1 gene can be mapped to 16p13.3 near DNA marker D16S291 (transcript G in FIG. 1).

Two exon traps from the 1.8F P1 clone were found to have a high level of homology to the previously described murine ΦAP3 encoding a zinc finger-containing transcription factor (Fognani et al., EMBO J. 12:4985–4992, 1993). The mΦAP3 protein, a zinc finger-containing transcription factor, is believed to function as a negative regulator for genes encoding proteins responsible for the inhibition of cell cycling (Fognani et al., supra.). The two exon traps were linked by PCR, with the resulting 1.2 kb PCR product being 85% identical at the nucleotide level to the murine ΦAP3 cDNA. Hybridization of the ΦAP3-like exon traps to the dot blotted P1 contig indicated that the gene lies in the non-overlapping region of the 1.8F P1, between the DNA markers KLH7 and GGG12 (transcript H in FIG. 1).

Significant homology was also seen between two exon traps obtained from the 97.10G P1 and the rat Rab26 gene encoding a ras-related GTP-binding protein involved in the regulation of vesicular transport (Nuoffer et al, Ann. Rev. Biochem. 63:949–990, 1994; Wagner et al., Biochem. Biophys. Res. Comm. 207:950–956, 1995). The Rab26-like exon traps were linked by RT-PCR (transcript J in FIG. 1) with the encoded sequences being 94% (83/88) identical at the protein level to Rab26 (FIG. 2).

In order to correlate exon traps with individual transcripts, cDNA library screening and PCR based approaches were used to clone transcribed sequences containing selected exon traps. RT-PCR was used to link individual exon traps together in cases where the two exon traps had homology to similar sequences in the databases. In cases where only single exon traps were available, 3' RACE or cDNA library screening was used to obtain additional sequences. Sequences from the exon traps and cloned products were used to map the position, and when possible the orientation, of the corresponding transcription units.

Six unique exon traps, containing sequences from at least eight exons, were shown to be from a transcriptional unit in the centromeric most P1 clone, 94.10H (transcript A in FIG. 1). A 2 kb cDNA linking the six exon traps was isolated and shown to hybridize to an 8 kb transcript. Additional hybridization studies indicated that the gene was oriented centromeric to telomeric, with at least 6 kb of the transcript originating from sequences centromeric of the P1 contig. Extensive homology was observed between the translated cDNA and a variety of protein kinases; however, the presence of the conserved HRDLKPEN motif (SEQ ID NO:71) encoded in exon trap L48734, as well as the partial cDNA, suggests that it encodes a serine/threonine kinase (van-der-Geer et al., Ann. Rev. Cell Bio. 10:251–337, 1994).

cDNAs were isolated using sequences derived from a separate 94.10H exon trap (Genbank Accession No. L48738) and the position and orientation of the corresponding transcription unit were determined. Two cDNA species were obtained using exon trap L48738 as a probe, with the only homology between the two species arising from the 109 bases contained in the exon trap. Using oligonucleotide probes, the transcription unit was mapped to a position near the 26–6DIS DNA marker, in a telomeric to centromeric orientation; however, only one of the cDNA species mapped to the P1 contig (transcript B in FIG. 1). Based on these data, it is likely that the second cDNA species originated from a region outside of the P1 contig, possibly from the duplicated 26–6PROX marker located further centromeric in 16p13.3 (Gillespie et al., Nuc. Acids Res. 18:7071–7075, 1990).

The 110.1F P1 clone contains at least two genes in addition to the ATP6C gene. Using BLASTX to search the protein databases, significant homology was observed between sequences encoded by exon trap L48741 and the N-acetylglucosamine-6-phosphate deacetylase (nagA) proteins from C. elegans (Wilson et al., Nature 368:32–38, 1994), E. coli (Plumbridge, Mol. Microbiol. 3:505–515, 1989) and Haemophilus (Fleischmann et al., Science 269:496–512, 1995). An alignment of the nagA proteins to the translated exon trap revealed the presence of multiple conserved regions (FIG. 2), suggesting that the exon trap contains sequences from the human nagA gene. Additional sequences from the nagA-like transcript have been cloned using 3' RACE and the transcription unit mapped to a region between NotI sites 2 and 3 in FIG. 1. The gene is oriented telomeric to centromeric with NotI site 2 being present in the 3' UTR of the RACE clone (transcript C in FIG. 1).

Two additional exon traps (Genbank Accession Nos. L75916 and L75917), mapping to the region of overlap between the 110.1F and 53.8B P1 clones (transcript D in FIG. 1), were shown to have homology with the chicken netrins (Kennedy et al., Cell 78:425–435, 1994; Serafini et al., Cell 78:409–424, 1994) and the C. elegans UNC-6 protein (Ishii et al., Neuron 9:873–881, 1992) (FIG. 2). The presence of the netrin-like exon traps in transcribed sequences based on RT-PCR using oligonucleotide primers (Table IV) was confirmed in spinal cord RNA. These results, indicate that a novel gene, hNET, encoding a human netrin gene has been isolated.

The netrins define a family of diffusable factors involved in axon outgrowth, while UNC-6 has been shown to play a role in the migration of mesodermal cells and axons (Ishii et al., supra. 1992). Given that netrins function as target-derived neural chemoattractants, it is likely that hNET has a restricted spatial and temporal pattern of expression.

Sequences encoded by exon trap, L75917, were shown to have significant homology with the C-terminal most epidermal growth factor (EGF) repeat found in the netrin and UNC-6 proteins (FIG. 2). The netrin-like trap, L75916, encodes sequences from the more divergent C-terminal domain of the netrins (FIG. 2). This region is the least conserved between UNC-6 and the netrins, with sequences being 63% conserved between netrin-1 and netrin-2 and 29% conserved between netrin-2 and UNC-6 (Serafini et al., supra. 1994).

The high level of conservation exhibited between hNET, chicken netrins 1 and 2, C. elegans UNC-6 and the laminins suggests that hNET is implicated in signaling developing neurons. For example, the chicken netrin gene product has been shown to guide and redirect migrating commissural axons to their targets in both in vitro and in vivo studies (Serafini et al., supra.; Kennedy et al., supra.). Such chemoattractants may have a significant role in axon regeneration.

Exon trapping results further show that there is a novel ATPase Binding Cassette (ABC) transporter in the PKD1 locus located between the LCN1 and D16S291 markers in a centromeric to telomeric orientation. Database searches with the exon trap sequences show homology to the murine ABC1 and ABC2 genes (Luciani et al., Genomics 21:150–159, 1994). The human homologs of murine ABC1 and ABC2 have been cloned and mapped to human chromosome 9 (Luciani et al. supra.).

Seven exon traps with homology to ABC transporters were isolated from P1 clones 30.1F, 64.12C and 96.4B. Additional sequences encoded by the ABC3 gene were obtained by RT-PCR (placenta and brain RNA as template) and library PCR (using commercially available lung cDNA library as template) using custom primers designed from the exon traps (Tables II and III). Three exon traps (L48758–L48760) were obtained from the region of overlap between the 30.1F, 64.12C and 96.4B P1 clones (transcript F FIG. 1), while a fourth exon (L48753) maps to the 79.2A P1 clone, exclusively (transcript E in FIG. 1).

TABLE II

Oligonucleotides Used to Clone Additional Sequences

| Gene[a] | Method[b] | Oligonucleotide 1[c] | Oligonucleotide 2[d] | Clone Size[e] |
|---|---|---|---|---|
| A | Genetrapper | TGACGCCGTGCCCATCCAGT (SEQ ID NO:36) | CAGCGTGGTGTTATGTTCCT (SEQ ID NO:37) | 2.0 kb |
| B | Genetrapper | TTGGGCCTGTGCTGAACTAC (SEQ ID NO:38) | CGGCAAGCTGGTGATTAACA (SEQ ID NO:39) | 1.3 kb |
| C | 3' RACE | CGGCAGAGGATGCTGTGT (SEQ ID NO:40) | GCGGAGCCACCTTCATCA (SEQ ID NO:41) | 0.6 kb |
| F | RT-PCR | GACGCTGGTGAAGGAGC (SEQ ID NO:42) | TCGCTGACCGCCAGGAT (SEQ ID NO:43) | 1.1 kb |
| H | RT-PCR | CTGTCGGGAAGGTCTCACTG (SEQ ID NO:44) | GTTCACCGCCTTGGAGGATT (SEQ ID NO:45) | 1.1 kb |
| J | RT-PCR | GTGTGGGGAAGACCTGTCTG (SEQ ID NO:46) | AGGAGGCCTTGTTGGTGACA (SEQ ID NO:47) | 0.24 kb |
| L | Genetrapper | ACGGACACCTGGGCTTC (SEQ ID NO:48) | AAACGGGAGGAGGTGGA (SEQ ID NO:49) | 1.7 kb |
| M | Genetrapper | TGTGGCTATGAGCTGTTCTC (SEQ ID NO:50) | GCAGTCCCGATTCTGAATAT (SEQ ID NO:51) | 0.7 kb |

[a]Gene as denoted in FIG. 1.
[b]Method used to clone additional sequences. Lifetechnologies Genetrapper system, 3' RACE and RT-PCR were performed as described in the Materials and Methods.
[c]Sequence of oligonucleotides used to obtain additional sequences. For the Genetrapper system, this oligonucleotide was used in the direct selection step. In the case of 3' RACE experiments, this oligo was the external prime. While in RT-PCR experiments, the designated oligonucleotide was used as a sense primer.
[d]Sequence of oligonucleotides. In the Genetrapper experiments, this oligonucleotide was used in the repair step. For 3' RACE experiments, this was the internal primer. For RT-PCR experiments, this was the antisense primer.
[e]Size of clone obtained using the primer pair.

TABLE III

Oligonucleotides Used to Clone Additional Sequences from human ABC3

| Method[a] | Oligonucleotide 1[b] | Oligonucleotide 2[c] | Clone Name[d] | Clone Size[e] |
|---|---|---|---|---|
| Genetrapper | CATTGCCCGTGCTGTCGTG (SEQ ID NO:52) | CATCGCCGCCTCCTTCATG (SEQ ID NO:53) | ABC3 (gt.1) | 5.8 kb |
| RT-PCR | CATTGCCCGTGCTGTCGTG (SEQ ID NO:52) | GCGGAGCCACCTTCATCA (SEQ ID NO:54) | ABC3 (A12) | 1.7 kb |
| RT-PCR | GACGCTGGTGAAGGAGC (SEQ ID NO:55) | ATCCTGGCGGTCAGCGA (SEQ ID NO:56) | ABC3 (3-12) | 1.1 kb |
| RT-PCR | AGGGATTCGACATTGCC (SEQ ID NO:57) | CTTCAGAGACTCAGGGCAT (SEQ ID NO:58) | ABC3 (#2) | 0.5 kb |

[a]Method used to clone additional sequences. Lifetechnologies Genetrapper system and RT-PCR were performed as described in the Materials and Methods.
[b]Sequence of oligonucleotides used to obtain additional sequences. For the Genetrapper system, this oligonucleotide was used in the direct selection step. In the case of RT-PCR experiments, the designated oligonucleotide was used as a sense primer.
[c]Sequence of oligonucleotides. In the Genetrapper experiments, this oligonucleotide was used in the repair step. For RT-PCR experiments, this was the antisense primer.
[d]Assigned name of isolated cDNA clones.
[e]Size of clone obtained using the primer pair.

TABLE IV

Oligonucleotides Used to Clone Sequences from human Netrin 2

| Method[a] | Oligonucleotide 1[b] | Oligonucleotide 2[c] | Clone Name[d] | Clone Size[e] |
|---|---|---|---|---|
| 1° RT-PCR | GCCTGTCATCGCTCTAG (SEQ ID NO:59) | CAGTCGCAGGCCCTGCA (SEQ ID NO:60) | | |
| 2° PCR | GAGGACGCGCCAACATC (SEQ ID NO:61) | CGGCAGTAGTGGCAGTG (SEQ ID NO:62) | 1121–1123 | 1264 bp |
| 1° RT-PCR | CCTGCCTCGCTTGCTCCTGC (SEQ ID NO:63) | CGGGCAGCCGCAGGCCGCAT (SEQ ID NO:64) | | |
| 2° PCR | CCTGCAACGGCCATGCCCGC (SEQ ID NO:65) | GCATCCCCGGCGGGCACCCA (SEQ ID NO:66) | 1131–1141 | 601 bp |

[a]Method used to clone sequences. For 2° PCR, the 1° RT-PCR product was diluted to a final concentration of one to a thousand.
[b]Sequence of sense-strand oligonucleotides.
[c]Sequence of anti-sense-strand oligonucleotides.
[d]Assigned name of isolated cDNA clones.
[e]Size of clone obtained using the primer pair.

Exon traps from the hABC3 transporter encoded by transcript F encode sequences with homology to the R-domain of the murine ABC1 and ABC2 genes. The R-domain is believed to play a regulatory role based on the comparison to a conserved region in CFTR. To date, only ABC1, ABC2 and CFTR have been shown to contain an R-domain (Luciani et al., supra. 1994).

Additionally, a 1.1 kb RT-PCR product which links the three exon traps from transcript F, with the RT-PCR product detecting a 7 kb message on Northern blots has been obtained. Based on a search of the dbEST database, a cDNA from this region was obtained with sequences from exon traps L75924 and L75925 being contained in cDNA 49233 from the I.M.A.G.E. Consortium (Lennon et al., supra.). The presence of both cloned reagents in the same transcription unit has been confirmed using RT-PCR.

Accordingly, the present invention provides a novel human ABC gene which has homology to the murine ABC1 and ABC2 genes. The 5.8 kb cDNA clone was isolated from a normal human lung cDNA library using custom oligonucleotides designed from the 5' most exon trap. A 6–7 kb transcript is detected by the cDNA on Northern blots, with highest levels of expression in lung and lesser amounts in brain and placenta. In view of its high level of expression in lung tissue and R-domain having homology with a conserved region in the CFTR gene, the hABC3 gene may have significant therapeutic implications for cystic fibrosis.

Five trapped exons from P1 clones 109.8C and 47.2H were shown to contain sequences with homology to the human ribosomal protein L3 cDNA, with hybridization studies indicating that the L3-like gene is oriented centromeric to telomeric (transcript L in FIG. 1). The ribosomal L3 gene product is one of five essential proteins for peptidyl-transferase activity in the large ribosomal subunit (Schulze and Nierhaus, *EMBO J*. 1:609–613, 1982). Not surprisingly, the L3 amino acid sequence is highly conserved across species. Mammalian L3 genes showing ~98% protein sequence identity have been characterized from man (Genbank Accession No. X73460), mouse (Peckham et al., *Genes Dev*. 3:2062–2071, 1989), rat (Kuwano and Wool, *Biochem. Biophys. Res. Comm*. 187:58–64,1992) and cow (Simonic et al., *Biochim. Biophys. Acta* 1219:706–710, 1994). The cumulative percent identity between the trapped exons and the reported human ribosomal protein L3 cDNA was 74% (537/724) at the nucleotide level.

A full-length cDNA encoding a novel ribosomal L3 protein subtype, SEM L3, was isolated and sequenced FIG. 11). The deduced protein sequence is 407 amino acids long and shows 77% identity to other known mammalian L3 proteins, which are themselves highly conserved. Hybridization analysis of human genomic DNA suggests this novel gene is single copy and has a tissue specific pattern of expression.

The expression pattern of the previously identified human L3 gene and the novel human SEM L3 was determined using multiple tissue Northern blots. The human L3 gene showed a ubiquitous pattern of expression in all tissues with the highest expression in the pancreas. In contrast, the novel gene described herein is strongly expressed in skeletal muscle and heart tissue, with low levels of expression in the pancreas. This novel gene, SEM L3 (Strongly Expressed in Muscle), is located in a gene-rich region near the PKD1 and TSC2 genes on chromosome 16p13-3.

The SEM L3 protein is more closely related to the above mentioned cytoplasmic ribosomal proteins than to previously described nucleus-encoded mitochondrial proteins (Graack et al., *Eur. J. Biochem*. 206:373–380, 1992). The presence of a highly conserved nuclear localization sequence in the SEM L3 further supports the hypothesis that it represents a novel cytoplasmic L3 ribosomal protein subtype and not a nucleus-encoded mitochondrial protein.

In addition, an exon trap (Genbank Accession No. L48792) from a gene which is located telomeric of the L3-like gene was obtained (transcript M in FIG. 1). Sequences encoded by transcript M were shown to have homology to pilB from *Neisseria gonorrhoeae* (Taha et al., *EMBO J*. 7:4367–4378, 1988) as well as to a computer predicted 17.2 kDa protein encoded by cosmid F44E2.6 from *C. elegans* (Wilson et al., supra. 1994).

Using sequences from exon trap L48792, a 600 bp partial cDNA was isolated and it was determined that the corresponding gene is oriented centromeric to telomeric. A 1.3 kb message was detected by the cDNA on Northern blots. Sequences conserved between the partial cDNA and the hypothetical 17.2 kDa protein were also conserved in the pilB protein from *Neisseria gonorrhoeae* (Taha et al., supra. 1988), a hypothetical 19.3 kDa protein from yeast (Genbank Accession No. P25566), and a fimbrial transcription regulation repressor from Haemophilus (Fleischmann et al., supra. 1995) (FIG. 2). The pilB protein has homology to histidine kinase sensors and has been shown to play a role in the repression of pilin production in *Neisseria gonorrhoeae* (Taha et al., supra. 1988; Taha et al., *Mol. Microbiol*. 5:137–148, 1991). However, residues conserved between pilB, transcript M and the *C. elegans*, yeast, and Haemophilus sequences do not include the conserved histidine kinase domains from pilB (Taha et al., supra. 1991). These findings suggest that the conserved region in transcript M has a function which is independent of the proposed histidine kinase sensor activity of pilB.

An additional exon trap from region of overlap between the 109.8C and 47.2H P1 clones was shown to contain human LLRep3 sequences (Slynn et al., Nuc. Acids Res. 18:681, 1990). Hybridization studies indicated that the LLRep3 sequences (transcript K in FIG. 1) were located between the sazD and L3-like genes. The region of highest gene density appears to be at the telomeric end of this cloned interval, particularly the region between TSC2 and D16S84, with a minimum of five genes mapping to this region (transcription units K, L and M, sazD and hERV1).

Also mapped to this region, was an exon trap which is 86% identical (170/197) at the nucleotide level to the previously described rat augmenter of liver regeneration (Hagiya et al., Proc. Natl. Acad. Sci., USA 91:8142–8146, 1994). ALR is a growth factor which augments the growth of damaged liver tissue while having no effect on the resting liver. Studies have demonstrated that rat ALR is capable of augmenting hepatocytic regeneration following hepatectomy.

This ALR-like exon trap was also shown to contain sequences from the recently described hERV1 gene, which encodes a functional homologue to yeast ERV1 (Lisowsky et al., supra. 1995).

A 468 bp cDNA has been obtained from the human ALR gene (FIG. 13). The ALR sequences encode a 119 amino acid protein which is 84.8% identical and 94.1% similar to the rat ALR protein (FIG. 14).

The cloning of human ALR has significant implications in the treatment of degenerative liver diseases. For example, biologically active rat ALR has been produced from COS-7 cells expressing rat ALR cDNA (Hagiya et al. supra.). Accordingly, recombinant hALR could be used in the treatment of damaged liver. In addition, a construct expressing hALR could be used in gene therapy to treat chronic liver diseases.

Forty three of the trapped exons did not have significant homology to sequences in the protein or DNA databases, nor were ESTs (expressed sequence tags) containing sequences from the exon traps observed in dbEST. The absence of ESTs containing sequences from these novel exon traps is not surprising since one of the criterion for selecting exon traps for further analysis was the presence of an EST in the database. These trapped exons are likely to represent bona fide products, since in many cases they were trapped multiple times from different P1 clones and in combination with flanking exons.

The present invention encompasses novel human genes an isolated nucleic acids comprising unique exon sequences from chromosome 16. The sequences described herein provide a valuable resource for transcriptional mapping and create a set of sequence-ready templates for a gene-rich interval responsible for at least two inheritable diseases.

Accordingly, the present invention provides isolated nucleic acids encoding human netrin (hNET), human ATPase Binding Cassette transporter (hABC3), human ribosomal L3 (SEM L3) and human augmenter of liver regeneration (hALR) polypeptides. The present invention further provides isolated nucleic acids comprising unique exon sequences from chromosome 16. The term "nucleic acids" (also referred to as polynucleotides) encompasses RNA as well as single and double-stranded DNA, cDNA and oligonucleotides. As used herein, the phrase "isolated" means a polynucleotide that is in a form that does not occur in nature.

One means of isolating polynucleotides encoding invention polypeptides is to probe a human tissue-specific library with a natural or artificially designed DNA probe using methods well known in the art. DNA probes derived from the human netrin gene, hNET, the human ABC transporter gene, hABC3, the human ribosomal protein L3 gene, SEM L3, or the human augmenter of liver regeneration gene, hALR, are particularly useful for this purpose. DNA and cDNA molecules that encode invention polypeptides can be used to obtain complementary genomic DNA, cDNA or RNA from human, mammalian, or other animal sources, or to isolate related cDNA or genomic clones by the screening of cDNA or genomic libraries, by methods described in more detail below.

The present invention encompasses isolated nucleic acid sequences, including sense and antisense oligonucleotide sequences, derived from the sequences shown in FIGS. 3, 4, 8 and 11. hNET-, hABC3-, SEM L3-, and hALR-derived sequences may also be associated with heterologous sequences, including promoters, enhancers, response elements, signal sequences, polyadenylation sequences, and the like. Furthermore, the nucleic acids can be modified to alter stability, solubility, binding affinity, and specificity. For example, invention-derived sequences can further include nuclease-resistant phosphorothioate, phosphoroamidate, and methylphosphonate derivatives, as well as "protein nucleic acid" (PNA) formed by conjugating bases to an amino acid backbone as described in Nielsen et al., Science, 254:1497, 1991. The nucleic acid may be derivatized by linkage of the α-anomer nucleotide, or by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

In general, nucleic acid manipulations according to the present invention use methods that are well known in the art, as disclosed in, for example, Sambrook et al., *Molecular Cloning, A Laboratory Manual 2d Ed.* (Cold Spring Harbor, N.Y., 1989), or Ausubel et al., *Current Protocols in Molecular Biology* (Greene Assoc., Wiley Interscience, NY, N.Y., 1992).

Examples of nucleic acids are RNA, cDNA, or genomic DNA encoding a human netrin, a human ABC transporter, a human ribosomal L3 subtype, or a human augmenter of liver regeneration polypeptide. Such nucleic acids may have coding sequences substantially the same as the coding sequence shown in FIGS. 3, 4, 8 and 11, respectively.

The present invention further provides isolated oligonucleotides corresponding to sequences within the hNET, hABC3, SEM L3, hALR genes, or within the respective cDNAs, which, alone or together, can be used to discriminate between the authentic expressed gene and homologues or other repeated sequences. These oligonucleotides may be from about 12 to about 60 nucleotides in length, preferably about 18 nucleotides, may be single- or double-stranded, and may be labeled or modified as described below.

This invention also encompasses nucleic acids which differ from the nucleic acids shown in FIGS. 3, 4, 8 and 11, but which have the same phenotype, i.e., encode substantially the same amino acid sequence set forth in FIGS. 3, 4, 8 and 11, respectively. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode proteins that are the same as those disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding human netrin, human ABC3 transporter, human ribosomal L3 subtype, and human augmenter of liver regeneration polypeptides that, by virtue of the degeneracy of the genetic code, do not necessarily hybridize to the invention nucleic acids under specified hybridization conditions. Preferred nucleic acids encoding the invention polypeptide are comprised of nucleotides that encode substantially the same amino acid sequence set forth in FIGS. 4, 8 and 11. Alternatively, preferred nucleic acids encoding the invention polypeptide(s) hybridize under high stringency conditions to substantially the entire sequence, or substantial portions (i.e., typically at least 12 to 60 nucleotides) of the nucleic acid sequence set forth in FIGS. 3, 4, 8 and 11, respectively.

Stringency of hybridization, as used herein, refers to conditions under which polynucleotide hybrids are stable. As known to those of skill in the art, the stability of hybrids is a function of sodium ion concentration and temperature. (See, for example, Sambrook et al., supra.).

The present invention provides isolated polynucleotides operatively linked to a promoter of RNA transcription, as well as other regulatory sequences. As used herein, the phrase "operatively linked" refers to the functional relationship of the polynucleotide with regulatory and effector sequences of nucleotides, such as promoters, enhancers, transcriptional and translational stop sites, and other signal sequences. For example, operative linkage of a polynucleotide to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide.

Promoter regions include specific sequences that are sufficient for RNA polymerase recognition, binding and transcription initiation. Additionally, promoter regions include sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, and the like.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Similarly, alternative codons, encoding the same amino acid, can be substituted for coding sequences of the human netrin, human ABC3 transporter, the human ribosomal L3 subtype, or the human augmenter of liver regeneration polypeptide in order to enhance transcription (e.g., the codon preference of the host cell can be adopted, the presence of G-C rich domains can be reduced, and the like).

Examples of vectors are viruses, such as baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColEl for proper episomal replication; versatile multiple cloning sites; and T7 and SP6 RNA promoters for in vitro transcription of sense and antisense RNA. Other means are well known and available in the art.

Also provided are vectors comprising a polynucleotide encoding human netrin, human ABC3 transporter, human ribosomal L3 subtype, and human augmenter of liver regeneration polypeptides, adapted for expression in a bacterial cell, a yeast cell, an amphibian cell, an insect cell, a mammalian cell and other animal cells. The vectors additionally comprise the regulatory elements necessary for expression of the polynucleotide in the bacterial, yeast, amphibian, mammalian or animal cells so located relative to the polynucleotide encoding human netrin, human ABC3 transporter, human ribosomal L3 subtype, or human augmenter of liver regeneration polypeptides as to permit expression thereof. As used herein, "expression" refers to the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al., supra). Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general. Expression vectors are useful to produce cells that express the invention receptor.

This invention provides a transformed host cell that recombinantly expresses the human netrin, human ABC3 transporter, human ribosomal L3 subtype, or human augmenter of liver regeneration polypeptides. Invention host cells have been transformed with a polynucleotide encoding a human netrin, a human ABC3 transporter, a human ribosomal L3 subtype, or a human augmenter of liver regeneration polypeptide. An example is a mammalian cell comprising a plasmid adapted for expression in a mammalian cell. The plasmid contains a polynucleotide encoding human netrin, human ABC3 transporter, human ribosomal L3 subtype, or human augmenter of liver regeneration polypeptide and the regulatory elements necessary for expression of the invention protein.

Appropriate host cells include bacteria, archebacteria, fungi, especially yeast, plant cells, insect cells and animal cells, especially mammalian cells. Of particular interest are E. coli, B. Subtilis, Saccharomyces cerevisiae, SF9 cells, C129 cells, 293 cells, Neurospora, and CHO cells, COS cells, HeLa cells, and immortalized mammalian myeloid and lymphoid cell lines. Preferred replication systems include M13, ColE1, SV40, baculovirus, lambda, adenovirus, artificial chromosomes, and the like. A large number of transcription initiation and termination regulatory regions have been isolated and shown to be effective in the transcription and translation of heterologous proteins in the various hosts. Examples of these regions, methods of isolation, manner of manipulation, and the like, are known in the art. Under appropriate expression conditions, host cells can be used as a source of recombinantly produced hNET, hABC3, SEM L3 and/or hALR.

Nucleic acids (polynucleotides) encoding invention polypeptides may also be incorporated into the genome of recipient cells by recombination events. For example, such a sequence can be microinjected into a cell, and thereby effect homologous recombination at the site of an endogenous gene encoding hNET, hABC3, SEM L3, and/or hALR an analog or pseudogene thereof, or a sequence with substantial identity to a hNET-, hABC3-, SEM L3-, or hALR-encoding gene. Other recombination-based methods such as nonhomologous recombinations or deletion of endogenous gene by homologous recombination, especially in pluripotent cells, may also be used.

The present invention provides isolated peptides, polypeptides(s) and/or protein(s) encoded by the invention nucleic acids. The present invention also encompasses isolated polypeptides having a sequence encoded by hNET, hABC3, SEM L3, and hALR genes, as well as peptides of six or more amino acids derived therefrom. The polypeptide(s) may be isolated from human tissues obtained by biopsy or autopsy, or may be produced in a heterologous cell by recombinant DNA methods as described herein.

As used herein, the term "isolated" means a protein molecule free of cellular components and/or contaminants normally associated with a native in vivo environment. Invention polypeptides and/or proteins include any natural occurring allelic variant, as well as recombinant forms thereof. Invention polypeptides can be isolated using various methods well known to a person of skill in the art.

The methods available for the isolation and purification of invention proteins include, precipitation, gel filtration, and chromatographic methods including molecular sieve, ion-exchange, and affinity chromatography using e.g. hNET-, hABC3-, SEM L3-, and/or hALR-specific antibodies or ligands. Other well-known methods are described in Deutscher et al., Guide to Protein Purification: Methods in Enzymology Vol. 182, (Academic Press, 1990). When the invention polypeptide to be purified is produced in a recombinant system, the recombinant expression vector may comprise additional sequences that encode additional amino-terminal or carboxy-terminal amino acids; these extra amino acids act as "tags" for immunoaffinity purification using immobilized antibodies or for affinity purification using immobilized ligands.

Peptides comprising hNET-, hABC3-, SEM L3-or hALR-specific sequences may be derived from isolated larger hNET, hABC3, SEM L3, or hALR polypeptides described above, using proteolytic cleavages by e.g. proteases such as trypsin and chemical treatments such as cyanogen bromide that are well-known in the art. Alternatively, peptides up to 60 residues in length can be routinely synthesized in milligram quantities using commercially available peptide synthesizers.

An example of the means for preparing the invention polypeptide(s) is to express polynucleotides encoding hNET, hABC3, SEM L3, and/or hALR in a suitable host cell, such as a bacterial cell, a yeast cell, an amphibian cell (i.e., oocyte), an insect cell (i.e., drosophila) or a mammalian cell, using methods well known in the art, and recovering the expressed polypeptide, again using well-known methods. Invention polypeptides can be isolated directly from cells that have been transformed with expression vectors, described below in more detail. The invention polypeptide, biologically active fragments, and functional equivalents thereof can also be produced by chemical synthesis. As used herein, "biologically active fragment" refers to any portion of the polypeptide represented by the amino acid sequence in FIGS. 4, 8 and 11 that can assemble into an active protein. Synthetic polypeptides can be produced using Applied Biosystems, Inc. Model 430A or 431A automatic peptide synthesizer (Foster City, Calif.) employing the chemistry provided by the manufacturer.

Modification of the invention nucleic acids, polynucleotides, polypeptides, peptides or proteins with the following phrases: "recombinantly expressed/produced", "isolated", or "substantially pure", encompasses nucleic acids, polynucleotides, polypeptides, peptides or proteins that have been produced in such form by the hand of man, and are thus separated from their native in vivo cellular environment. As a result of this human intervention, the recombinant nucleic acids, polynucleotides, polypeptides, peptides and proteins of the invention are useful in ways that the corresponding naturally occurring molecules are not, such as identification of selective drugs or compounds.

Sequences having "substantial sequence homology" are intended to refer to nucleotide sequences that share at least about 90% identity with invention nucleic acids; and amino acid sequences that typically share at least about 95% amino acid identity with invention polypeptides. It is recognized, however, that polypeptides or nucleic acids containing less than the above-described levels of homology arising as splice variants or that are modified by conservative amino acid substitutions, or by substitution of degenerate codons are also encompassed within the scope of the present invention.

The present invention provides a nucleic acid probe comprising a polynucleotide capable of specifically hybridizing with a sequence included within the nucleic acid sequence encoding human netrin, human ABC3 transporter, human ribosomal L3 subtype, or human augmenter of liver regeneration polypeptide, for example, a coding sequence included within the nucleotide sequence shown in FIGS. 3, 4, 8 and 11, respectively.

As used herein, a "nucleic acid probe" may be a sequence of nucleotides that includes from about 12 to about 60 contiguous bases set forth in FIGS. 3, 4, 8 and 11, preferably about 18 nucleotides, may be single- or double-stranded, and may be labeled or modified as described herein. Preferred regions from which to construct probes include 5' and/or 3' coding sequences, sequences predicted to encode transmembrane domains, sequences predicted to encode cytoplasmic loops, signal sequences, ligand binding sites, and the like.

Full-length or fragments of cDNA clones can also be used as probes for the detection and isolation of related genes. When fragments are used as probes, preferably the cDNA sequences will be from the carboxyl end-encoding portion of the cDNA, and most preferably will include predicted transmembrane domain-encoding portions of the cDNA sequence. Transmembrane domain regions can be predicted based on hydropathy analysis of the deduced amino acid sequence using, for example, the method of Kyte and Doolittle (*J. Mol. Biol.* 157:105, 1982).

As used herein, the phrase "specifically hybridizing" encompasses the ability of a polynucleotide to recognize a sequence of nucleic acids that are complementary thereto and to form double-helical segments via hydrogen bonding between complementary base pairs. Nucleic acid probe technology is well known to those skilled in the art who will readily appreciate that such probes may vary greatly in length and may be labeled with a detectable agent, such as a radioisotope, a fluorescent dye, and the like, to facilitate detection of the probe. Invention probes are useful to detect the presence of nucleic acids encoding human netrin, human ABC3 transporter, human ribosomal L3 subtype, or human augmenter of liver regeneration polypeptides. For example, the probes can be used for in situ hybridizations in order to locate biological tissues in which the invention gene is expressed. Additionally, synthesized oligonucleotides complementary to the nucleic acids of a polynucleotide encoding human netrin, human ABC3 transporter, human ribosomal L3 subtype, or human augmenter of liver regeneration polypeptides are useful as probes for detecting the invention genes, their associated mRNA, or for the isolation of related genes using homology screening of genomic or cDNA libraries, or by using amplification techniques well known to one of skill in the art.

Also provided are antisense oligonucleotides having a sequence capable of binding specifically with any portion of an mRNA that encodes human netrin, human ABC3 transporter, human ribosomal L3 subtype, or human augmenter of liver regeneration polypeptide so as to prevent translation of the mRNA. The antisense oligonucleotide may have a sequence capable of binding specifically with any portion of the sequence of the cDNA encoding human netrin, human ABC3 transporter, human ribosomal L3 subtype, or human augmenter of liver regeneration polypeptide. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense oligonucleotide is an antisense oligonucleotide comprising chemical analogs of nucleotides (i.e., synthetic antisense oligonucleotide, SAO).

Compositions comprising an amount of the antisense oligonucleotide, (SAOC), effective to reduce expression of the human netrin, the human ABC3 transporter, the human ribosomal L3 subtype, or the human augmenter of liver regeneration polypeptide by passing through a cell membrane and binding specifically with mRNA encoding the human netrin, the human ABC3 transporter, the human ribosomal L3 subtype, or the human augmenter of liver regeneration polypeptide so as to prevent its translation and an acceptable hydrophobic carrier capable of passing through a cell membrane are also provided herein. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

This invention provides a means to modulate levels of expression of invention polypeptides by the use of a synthetic antisense oligonucleotide composition (SAOC) which inhibits translation of mRNA encoding these polypeptides. Synthetic oligonucleotides, or other antisense chemical structures designed to recognize and selectively bind to mRNA, are constructed to be complementary to portions of the nucleotide sequences shown in FIG. 3, 4, 8 and 11, of DNA, RNA or chemically modified, artificial nucleic acids. The SAOC is designed to be stable in the blood stream for administration to a subject by injection, or in laboratory cell culture conditions. The SAOC is designed to be capable of passing through the cell membrane in order to enter the cytoplasm of the cell by virtue of physical and chemical properties of the SAOC which render it capable of passing through cell membranes, for example, by designing small, hydrophobic SAOC chemical structures, or by virtue of specific transport systems in the cell which recognize and transport the SAOC into the cell.

In addition, the SAOC can be designed for administration only to certain selected cell populations by targeting the SAOC to be recognized by specific cellular uptake mechanisms which bind and take up the SAOC only within select cell populations. For example, the SAOC may be designed to bind to a receptor found only in a certain cell type, as discussed supra. The SAOC is also designed to recognize and selectively bind to the target mRNA sequence, which may correspond to a sequence contained within the sequence shown in FIGS. 3, 4, 8 and 11. The SAOC is designed to inactivate the target mRNA sequence by either binding to the target mRNA and inducing degradation of the mRNA by, for example, RNase I digestion, or inhibiting translation of the mRNA target by interfering with the binding of translation-regulating factors or ribosomes, or inclusion of other chemical structures, such as ribozyme sequences or reactive chemical groups which either degrade or chemically modify the target mRNA. SAOCs have been shown to be capable of such properties when directed against mRNA targets (see Cohen et al., *TIPS*, 10:435, 1989 and Weintraub, *Sci. American*, January pp.40, 1990).

This invention further provides a composition composition containing an acceptable carrier and any of an isolated, purified human netrin, human ABC3 transporter, human ribosomal L3 subtype, or human augmenter of liver regeneration polypeptide, an active fragment thereof, or a purified, mature protein and active fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

Also provided are antibodies having specific reactivity with the human netrin, the human ABC3 transporter, the human ribosomal L3 subtype, or the human augmenter of liver regeneration polypeptides of the subject invention. Active fragments of antibodies are encompassed within the definition of "antibody". Invention antibodies can be produced by methods known in the art using the invention proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory 1988).

The polypeptides of the present invention can be used as the immunogen in generating such antibodies. Alternatively, synthetic peptides can be prepared (using commercially available synthesizers) and used as immunogens. Where natural or synthetic hNET-, hABC3-, SEM L3-, and/or hALR-derived peptides are used to induce a hNET-, hABC3-, SEM L3-, and/or hALR-specific immune response, the peptides may be conveniently coupled to an suitable carrier such as KLH and administered in a suitable adjuvant such as Freund's. Preferably, selected peptides are coupled to a lysine core carrier substantially according to the methods of Tam, *Proc. Natl. Acad. Sci, USA 85:5409–5413, 1988.* The resulting antibodies may be modified to a monovalent form, such as, for example, Fab, $Fab_2$, FAB', or FV. Anti-idiotypic antibodies may also be prepared using known methods.

In one embodiment, normal or mutated hNET, hABC3, SEM L3, or hALR polypeptides are used to immunize mice, after which their spleens are removed, and splenocytes used to form cell hybrids with myeloma cells and obtain clones of antibody-secreted cells according to techniques that are standard in the art. The resulting monoclonal antibodies are screened for specific binding to hNET, hABC3, SEM L3, and/or hALR proteins or hNET-, hABC3-, SEM L3-, and/or hALR-related peptides.

In another embodiment, antibodies are screened for selective binding to normal or mutated hNET, hABC3, SEM L3, or hALR sequences. Antibodies that distinguish between normal and mutant forms of hNET, hABC3, SEM L3, or hALR may be used in diagnostic tests (see below) employing ELISA, EMIT, CEDIA, SLIFA, and the like. Anti-hNET, hABC3, SEM L3, or hALR antibodies may also be used to perform subcellular and histochemical localization studies. Finally, antibodies may be used to block the function of the hNET, hABC3, SEM L3, and/or hALR polypeptide, whether normal or mutant, or to perform rational drug design studies to identify and test inhibitors of the function (e.g., using an anti-idiotypic antibody approach).

Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338, 1991; Ausubel et al., supra.).

Invention antibodies can be used to isolate invention polypeptides. Additionally, the antibodies are useful for detecting the presence of the invention polypeptides, as well as analysis of polypeptide localization, composition, and structure of functional domains. Methods for detecting the presence of a human netrin, a human ABC3 transporter, a human ribosomal L3 subtype, or a human augmenter of liver regeneration polypeptide comprise contacting the cell with an antibody that specifically binds to the polypeptide, under conditions permitting binding of the antibody to the polypeptide, detecting the presence of the antibody bound to the cell, and thereby detecting the presence of the invention polypeptide on the cell. With respect to the detection of such polypeptides, the antibodies can be used for in vitro diagnostic or in vivo imaging methods.

Immunological procedures useful for in vitro detection of the target human netrin, human ABC3 transporter, human ribosomal L3 subtype, or human augmenter of liver regeneration polypeptide in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

For in vivo imaging methods, a detectable antibody can be administered to a subject and the binding of the antibody to the invention polypeptide can be detected by imaging techniques well known in the art. Suitable imaging agents are known and include, for example, gamma-emitting radionuclides such as $^{111}$In, $^{99m}$Tc, $^{51}$Cr and the like, as well as paramagnetic metal ions, which are described in U.S. Pat. No. 4,647,447. The radionuclides permit the imaging of tissues by gamma scintillation photometry, positron emission tomography, single photon emission computed tomography and gamma camera whole body imaging, while paramagnetic metal ions permit visualization by magnetic resonance imaging.

The invention provides a transgenic non-human mammal that is capable of expressing nucleic acids encoding a human netrin, a human ABC3 transporter, a human ribosomal L3 subtype, or a human augmenter of liver regeneration polypeptide. Also provided is a transgenic non-human mammal capable of expressing nucleic acids encoding a human netrin, a human ABC3 transporter, a human ribosomal L3 subtype, or a human augmenter of liver regeneration polypeptide so mutated as to be incapable of normal activity, i.e., does not express native protein.

The present invention also provides a transgenic non-human mammal having a genome comprising antisense nucleic acids complementary to nucleic acids encoding human netrin, human ABC3 transporter, human ribosomal L3 subtype, or human augmenter of liver regeneration polypeptide so placed as to be transcribed into antisense mRNA complementary to mRNA encoding a human netrin, human ABC3 transporter, human ribosomal L3 subtype, or human augmenter of liver regeneration polypeptide, which hybridizes thereto and, thereby, reduces the translation thereof. The polynucleotide may additionally comprise an inducible promoter and/or tissue specific regulatory elements, so that expression can be induced, or restricted to specific cell types. Examples of polynucleotides are DNA or cDNA having a coding sequence substantially the same as the coding sequence shown in FIGS. 3, 4, 8 and 11. Examples of non-human transgenic mammals are transgenic cows, sheep, goats, pigs, rabbits, rats and mice. Examples of tissue specificity-determining elements are the metallothionein promoter and the L7 promoter.

Animal model systems which elucidate the physiological and behavioral roles of invention polypeptides are produced by creating transgenic animals in which the expression of the polypeptide is altered using a variety of techniques. Examples of such techniques include the insertion of normal or mutant versions of nucleic acids encoding human netrin, human ABC3 transporter, human ribosomal L3 subtype, or human augmenter of liver regeneration polypeptide by microinjection, retroviral infection or other means well known to those skilled in the art, into appropriate fertilized embryos to produce a transgenic animal. See, for example, Carver, et al., *Bio/Technology* 11:1263–1270, 1993; Carver et al., *Cytotechnology* 9:77–84, 1992; Clark et al, *Bio/Technology* 7:487–492, 1989; Simons et al., *Bio/Technology* 6:179–183, 1988; Swanson et al., *Bio/Technology* 10:557–559, 1992; Velander et al., *Proc. Natl. Acad. Sci. USA* 89:12003–12007, 1992; Hammer et al., *Nature* 315:680–683, 1985; Krimpenfort et al., *Bio/Technology* 9:844–847, 1991; Ebert et al., *Bio/Technology* 9:835–838, 1991; Simons et al., *Nature* 328:530–532, 1987; Pittius et al., *Proc. Natl. Acad. Sci. USA* 85:5874–5878, 1988; Greenberg et al., *Proc. Natl. Acad. Sci. USA* 88:8327–8331, 1991; Whitelaw et al., Transg. Res. 1:3–13, 1991; Gordon et al., *Bio/Technology* 5:1183–1187, 1987; Grosveld et al., *Cell* 51:975–985, 1987; Brinster et al., *Proc. Natl. Acad. Sci. USA* 88:478–482, 1991; Brinster et al., *Proc. Natl. Acad. Sci. USA* 85:836–840, 1988; Brinster et al., *Proc. Natl. Acad. Sci. USA* 82:4438–4442, 1985; Al-Shawi et al., *Mol. Cell. Biol.* 10(3):1192–1198, 1990; Van Der Putten et al., *Proc. Natl. Acad. Sci. USA* 82:6148–6152, 1985; Thompson et al., *Cell* 56:313–321, 1989; Gordon et al., *Science* 214:1244–1246, 1981; and Hogan et al., *Manipulating the Mouse Embryo: A Laboratory Manual* (Cold Spring Harbor Laboratory, 1986).

Another technique, homologous recombination of mutant or normal versions of these genes with the native gene locus in transgenic animals, may be used to alter the regulation of expression or the structure of the invention polypeptides (see, Capecchi et al., *Science* 244:1288, 1989; Zimmer et al., *Nature* 338:150, 1989). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of the human netrin, human ABC3 transporter, human ribosomal L3 subtype, or human augmenter of liver regeneration polypeptide.

In contrast to homologous recombination, microinjection adds genes to the host genome, without removing host genes. Microinjection can produce a transgenic animal that is capable of expressing both endogenous and exogenous human netrin, human ABC3 transporter, human ribosomal L3 subtype, or human augmenter of liver regeneration polypeptides. Inducible promoters can be linked to the coding region of the nucleic acids to provide a means to regulate expression of the transgene. Tissue-specific regulatory elements can be linked to the coding region to permit tissue-specific expression of the transgene. Transgenic animal model systems are useful for in vivo screening of compounds for identification of ligands, i.e., agonists and antagonists, which activate or inhibit polypeptide responses.

The nucleic acids, oligonucleotides (including antisense), vectors containing same, transformed host cells, polypeptides, as well as antibodies of the present invention, can be used to screen compounds in vitro to determine whether a compound functions as a potential agonist or antagonist to the invention protein. These in vitro screening assays provide information regarding the function and activity of the invention protein, which can lead to the identification and design of compounds that are capable of specific interaction with invention proteins.

In accordance with still another embodiment of the present invention, there is provided a method for identifying compounds which bind to human netrin, human ABC3 transporter, human ribosomal L3 subtype, or human augmenter of liver regeneration polypeptides. The invention proteins may be employed in a competitive binding assay. Such an assay can accommodate the rapid screening of a large number of compounds to determine which compounds, if any, are capable of binding to invention polypeptides. Subsequently, more detailed assays can be carried out with those compounds found to bind, to further determine whether such compounds act as modulators, agonists or antagonists of invention polypeptides.

In accordance with another embodiment of the present invention, transformed host cells that recombinantly express invention polypeptides can be contacted with a test compound, and the modulating effect(s) thereof can then be evaluated by comparing the human netrin, human ABC3 transporter, human ribosomal L3 subtype, or human augmenter of liver regeneration polypeptide-mediated response in the presence and absence of test compound, or by comparing the response of test cells or control cells (i.e., cells that do not express invention polypeptides), to the presence of the compound.

As used herein, a compound or a signal that "modulates the activity" of an invention polypeptide refers to a compound or a signal that alters the activity of the human netrin, the human ABC3 transporter, the human ribosomal L3 subtype, or the human augmenter of liver regeneration polypeptide so that the activity of the invention polypeptide is different in the presence of the compound or signal than in the absence of the compound or signal. In particular, such compounds or signals include agonists and antagonists. An agonist encompasses a compound or a signal that activates polypeptide function. Alternatively, an antagonist includes a compound or signal that interferes with polypeptide function. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

The following examples are intended to illustrate the invention without limiting the scope thereof.

EXAMPLE I

Contig Assembly

A. Cosmids

Multiple cosmids were used as reagents to initiate walks in YAC and P1 libraries. Clones 16–166N (D16S277), 16–191N (D16S279), 16–198N (D16S280) and 16–140N (D16S276) were previously isolated from a cosmid library (Lerner et al., *Mamm. Genome* 3:92–100, 1992). Cosmids cCMM65 (D16S84), c291 (D16S291), cAJ42 (ATP6C) and cKG8 were recovered from total human cosmid libraries (made in-house or by Stratagene, La Jolla, Calif.) using either a cloned insert (CMM65) or sequence-specific oligonucleotides as probe. The c326 cosmid contig and clone 413C12 originated from a flow-sorted chromosome 16 library (Stallings et al., *Genomics* 13(4):1031–1039, 1992). The c326 contig was comprised of clones 2H2, 77E8, 325A11 and 325B10.

B. YACs

Screening of gridded interspersed-repetitive sequence (IRS pools from Mark I, Mark II and Mega-YAC libraries) with cosmid-specific IRS probes was as previously described (Liu et al., *Genomics* 26:178–191, 1995). IRS probes were made from cosmids 16–166N, 16–191N, cAJ42, 16–198N, 325A11, cCMM65, and 16–140N. Biotinylated YAC probes were generated by nick-translating complex mixtures of IRS products from each YAC. Mixtures of sufficient complexity were achieved by performing independent DNA amplifications of total yeast DNA using various Alu primers (Lichter et al., *Proc. Natl. Acad. Sci., USA* 87:6634–6638, 1990) and then combining the appropriate reactions containing the most diverse products.

C. P1s

Chromosome walking experiments were done using a single set of membranes which contained the gridded P1 library pools (Shepherd et al., supra. 1994). The gridded filters were kindly provided by Dr. Mark Leppert and the Technology Access Section of the Utah Center for Human Genome Research at the University of Utah. P1 gridded membranes were screened using end probes derived from a set of chromosome 16 cosmids (see above) and P1 clones as they were identified. Both RNA transcripts and bubble-PCR products were utilized as end probes.

D. Probes

Radiolabeled transcripts were generated using restriction enzyme digested cosmids or P1s (AluI, HaeIII, RsaI, TaqI) as template for phage RNA polymerases T3, T7 and SP6. The T3 and T7 promoter elements were present on the cosmid-derived templates while T7 and SP6 promoter sequences were contained on the P1-based templates. Transcription reactions were performed as recommended by the manufacturer (Stratagene, La Jolla, Calif.) in the presence of [$\alpha P^{32}$]-ATP (Amersham, Arlington Heights, Ill.).

Bubble-PCR products were synthesized from restriction enzyme digested P1s (AluI, HaeIII, RsaI, TaqI). Bubble adaptors with appropriate overhangs and phosphorylated 5' ends were ligated to digested P1 DNA basically as described for YACs (Riley et al., *Nuc. Acids Res.* 18:2887–2890, 1990). The sequence of the universal vectorette primer derived from the bubble adaptor sequence was 5'-GTTCGTACGAGAATCGCT-3' (SEQ ID NO:67), and differed from that of Riley and co-workers with 12 fewer 5' nucleotides. The $T_m$ of the truncated vectorette primer more closely matched that of the paired amplimer from the vector-derived promoter sequence (SP6, T7). The desired bubble-PCR product was gel purified prior to radiolabeling (Feinberg et al., *Anal. Biochem.* 132:6–13, 1983; Feinberg and Vogelstein, *Anal. Biochem.* 137:266–267, 1984).

The specificity of all end probes was determined prior to their use on the single set of gridded P1 filter arrays. Radiolabeled probes were pre-annealed to Cot1 DNA as recommended (Life Technologies Inc., Gaithersburg, Md.) and then hybridized to strips of nylon membrane to which were bound 10–20 ng each of the following DNAs: the cloned genomic template used to create the probe; one or more unrelated cloned genomic DNAs; cloned vector (no insert); and human genomic DNA.

Hybridizations were performed in CAK solution (5xSSPE, 1% SDS, 5xDenhardt's Solution, 100 mg/mL torula RNA) at 65° C. overnight. Individual end probes were present at a concentration of 5x10$^5$ cpm/mL. Hybridized membranes were washed to a final stringency of 0.1xSSC/0.1% SDS at 65° C. The hybridization results were visualized by autoradiography. Probes which hybridized robustly to their respective cloned template while not hybridizing to unrelated cloned DNAs, vector DNA or genomic DNA were identified and used to screen the gridded P1 filters.

Hybridization to the arrayed P1 pools was performed as described for the nylon membrane strips (above) except that multiple probes were used simultaneously. Positive clones were identified, plated at a density of 200–500 cfu per 100 mm plate (LB plus 25 mg/mL kanamycin), lifted onto 82 mm HATF membranes (Millipore, Bedford, Mass.), processed for hybridization (Sambrook et al., supra.) and then rescreened with the complex probe mixture.

A single positive clone from each pool was selected and replated onto a master plate. To identify the colony purified genomic P1 clone and its corresponding probe, multiple P1 DNA dot blots were prepared and each hybridized to individual radiolabeled probes. All hybridizations contained a chromosome 16p13.3 reference probe, e.g. cAJ42, as well as a uniquely labeled P1 DNA probe.

EXAMPLE II

Exon Trapping

Genomic P1 clones were prepared for exon trapping experiments by digestion with PstI, double digestion with BamHI/BglII, or by partial digestion with limiting amounts of Sau3AI. Digested P1 DNAs were ligated to BamHI-cut and dephosphorylated vector, pSPL3B, while PstI digested P1 DNA was subcloned into PstI-cut dephosphorylated vector, pSPL3B.

Ligations were performed in triplicate using 50 ng of vector DNA and 1, 3 or 6 mass equivalents of digested P1 DNA. Transformations were performed following an overnight 16° C. incubation, with 1/10 and 1/2 of the transformation being plated on LB (ampicillin) plates. After overnight growth at 37°C., colonies were scraped off those plates having the highest tranformation efficiency (based on a comparison to "no insert" ligation controls) and miniprepped using the alkaline lysis method. To examine the proportion of the pSPL3B containing insert, a small portion of the miniprep was digested with HindIII, which cuts pSPL3B on each side of the multiple cloning site.

EXAMPLE III

RNA Preparation

Approximately 10 μg of the remaining miniprep DNA was ethanol precipitated, resuspended in 100 μl of sterile PBS and electroporated into approximately 2x10$^6$ COS-7 cells (in 0.7 ml of ice cold PBS) using a BioRad GenePulser electroporator (1.2 kV, 25 μF and 200 Ω). The electroporated cells were incubated for 10 min. on ice prior to their addition to a 100 mm tissue culture dish containing 10 ml of prewarmed complete DMEM.

Cytoplasmic RNA was isolated 48 hours post-transfection. The transfected COS-7 cells were removed from tissue culture dishes using 0.25% trypsin/1 mM EDTA (Life Technologies Inc., Gaithersburg, Md.). Trypsinized cells were washed in DMEM/10% FCS and resuspended in 400 μl of ice cold TKM (10 mM Tris-HCl pH 7.5, 10 mM KCl, 1 mM MgCl$_2$) supplemented with 1 μl of RNAsin (Promega, Madison, Wis.). After adding 20 μl of 10% Triton X-100, the cells were incubated for 5 min. on ice. The nuclei were removed by centrifugation at 1200 rpm for 5 min. at 4° C. Thirty microliters of 5% SDS was added to the supernatant, with the cytoplasmic RNA being further purified by three rounds of extraction using phenol/chloroform/isoamyl alcohol (24:24:1). The cytoplasmic RNA was ethanol precipitated and resuspended in 50 μl of H$_2$O.

Reverse transcription and PCR were performed on the cytoplasmic RNA prepared above as described (Church et al., supra. 1994) using commercially available exon trapping oligonucleotides (Life Technologies Inc., Gaithersburg, Md.). The resulting CUA-tailed products were shotgun subcloned into pAMP10 as recommended by the manufacturer (Life Technologies Inc.). Random clones from each ligation were analyzed by colony PCR using secondary PCR primers (Life Technologies Inc.).

Miniprep DNA containing the pAMP10/exon traps was prepared from overnight cultures by alkaline lysis using the EasyPrep manifold or a QIAwell 8 system according to the manufacturers' instructions (Pharmacia, Pistcataway, N.J. and Qiagen Inc., Chatsworth, Calif., respectively). DNA products containing trapped exons, based on comparison to the 177 bp "vector only" DNA product, were selected for sequencing.

EXAMPLE IV

Sequencing

Trapped exon DNA was sequenced with fluoroscein-labeled M13 universal and reverse primers using the Pharmacia Autoread Sequencing kit and Pharmacia ALF automated DNA sequencers. Sequences were assembled and analyzed using the Sequencher sequence analysis software (GeneCodes, Ann Arbor, Mich.).

Sequences from the exon traps were used to search the nonredundant nucleotide and dbEST databases using the BLASTN program (Altschul et al., *J. Mol. Biol.* 215:403–410, 1990), while protein databases were searched using BLASTX (Altschul et al., supra. 1990; Gish and States, *Nature Genet.* 3:266–272, 1993).

EXAMPLE V

RT-PCR, RACE, and cDNA Isolation

Based upon the sequence determined (above) two oligonucleotide primers (Table II) were designed for each exon trap using Oligo 4.0 (National Biosciences Inc., Plymouth, Min.).

To determine which tissue-specific library to screen for transcript or cDNA, RT-PCR reactions and/or PCR reactions were performed using different tissue-derived RNAs and/or cDNA libraries, respectively, as template with the oligonucleotide primers designed for each exon trap (above).

The oligonucleotides designed from the exons (Table II), were then used in one or more of the following positive selection formats to screen the corresponding tissue-specific cDNA library.

For RT-PCR experiments, the first oligonucleotide was used as a sense primer and the second oligonucleotide was used as an antisense primer. RT-PCR was performed as described using polyA+ RNA from adult brain and placenta (Kawasaki, In *PCR Protocols: A Guide to Methods and Applications*, Eds. Innis et al., Academic Press, San Diego, Calif., pp. 21–27, 1990). All PCR products were cloned using the pGEM-T vector as described by the manufacturer (Promega, Madison, Wis.).

To clone sequences 3' to selected exon traps, rapid amplification of cDNA ends (RACE) was performed as described (Frohman, *PCR Met. Appl.* 4:S40–S58, 1994). In 3' RACE experiments, the first oligonucleotide was used as the external primer and the second oligonucleotide was used as the internal primer.

For the Genetrapper cDNA Positive Selection System, the first oligonucleotide primer was biotinylated and used for direct selection, while the second oligonucleotide was used in the repair.

EXAMPLE VI

Nucleotide Sequence Analysis hNET: The method of exon trapping was used to recover two exon traps from the P1 clone 53.8B with significant homology to the chicken netrin-1 (96%) and netrin-2 (62.5%) genes (Serafini et al. supra.) (FIG. 5). Positive colonies were selected for sequencing by hybridization of a 6.0 kb BamHI fragment containing the two exon traps.

The resulting contig contains 6803 bp of contiguous genomic sequence (FIG. 3). This genomic sequence was then analyzed using the GRAIL2 program which identifies potential exons in addition to CpG islands and polyadenylation sites. GRAIL2 predicted five exons which had the most significant homology to the chicken netrin-2 gene. Based on this analysis and with the use of Pustell DNA and protein matrices, a gene model was constructed. The gene model predicts an open reading frame of 1743 bp.

hNET cDNA has a 5' start methionine codon, a 3' stop codon (TGA) and is 581 amino acids in length (FIG. 4). Based on this model, the gene contains 5 exons which comprise 2404 bp of genomic sequence. RT-PCR primers were designed (Table IV) from this model and used to amplify spinal cord RNA since spinal cord has been previously shown to express low levels of chicken netrin (Serafini et al. supra.). Nested PCR was required to detect RT-PCR products from human spinal cord RNA. Spinal cord RNA was reverse transcribed with random primers and primary PCR was performed using primers designed from the gene model (Table IV). The primary PCR product was then used as template for secondary PCR with a pair of nested primers (also designed from the gene model). The inclusion of betaine in the PCR reactions dramatically increased the purity and yield of the human netrin RT-PCR products (see, for example, International Publication No. WO 96/12041).

Sequence analysis of the RT-PCR products indicated that hNET contains at least six exons. The RT-PCR data indicate that the fourth predicted exon is actually split by an intron in the human netrin gene and is present as two exons. Three of the RT-PCR exons were shown to be identical to the original exon traps. Aside from the extra exon, the gene model is nearly identical to the RT-PCR products. The cDNA sequence and its predicted protein product are shown in FIG. 3. The final 207 bp of the coding region are predicted from the gene model.

hABC3: A total of 5.8 kb of cDNA sequence (FIG. 8) has been assembled for hABC3, using RT-PCR and cDNA library screening using oligonucleotide primers (Tables II and III). A 147 bp insertion is present in the RT-PCR product relative to the cDNA. This insertion does not disrupt the open reading frame and presumably results from alternative splicing of an exon. The assembled cDNA contains a 792 bp 3' untranslated region with a consensus polyadenylation—cleavage site 20 bp upstream of the polyA tail.

SEM L3: The longest cDNA is 1548 nucleotides in length (FIG. 11). All three cDNAs have an open reading frame (ORF) of 1224 nucleotide with the longest cDNA containing a 48 nucleotide 5' untranslated region. An inframe stop codon at position 7 is followed by the Kozak initiation sequence CCACCATGT (SEQ ID NO:68) (Kozak, *J. Cell Biol.* 115:887–903, 1991). The 3' UTR for each of the three cDNAs vary in length, and lacks a consensus polyadenylation cleavage site.

The longest cDNA was compared to the human, bovine and murine ribosomal L3 genes. At the nucleotide level there is only 74% identity between the SEM L3 cDNA and the consensus from these other ribosomal L3 cDNAs. This is in sharp contrast to the 89% identity shared between human, bovine, and murine L3 nucleotide sequences. There is no similarity between the 3' UTR of the cDNAs isolated here and the other L3 genes.

hALR: Sequences were cloned from the human ALR gene by 3' RACE using primers (e.g., external 5'-TGGCCCAGTTCATACATTTA-3' and internal 5'-TTACCCCTGTGAGGAGTGTG-3') (SEQ ID NO:69 and 70), respectively designed from the exon trap. A total of 468 bp have been obtained from the human ALR gene (FIG. 13).

EXAMPLE VII

Amino Acid Sequence Analysis hNET: hNET cDNA has at least 210 bp of 5' untranslated sequence and is 66% homologous to the chicken netrin-2 cDNA. The predicted protein product has 58.6% identity and 73.4% similarity to chicken netrin-2 (FIG. 5). The conserved N-terminal laminin domains found between chicken netrin-1 and netrin-2, C. elegans UNC-6 and the murine laminin protein B2 are also conserved in the human homologue (67.3% identity to chicken netrin-2 for domains V and VI; FIG. 6). Domain V contains three epidermal growth factor repeats and is 81.1% identical between the human homologue and chicken netrin-2. Domain C has the characteristic basic residue bias with an isoelectric point of 12.26 and has a partial RGD domain for potential adhesion/signaling receptors (FIG. 5).

hABC3: hABC3 cDNA contains an open reading frame of 1684 amino acids (FIG. 8). Comparison of ABC1, ABC2 and hABC3 reveals significant conservation in the regions surrounding the two ATP binding cassettes. As is the case with ABC1 and ABC2, the ATP binding cassettes of hABC3 flank a large linker domain containing numerous polar residues. The presence of these features in the linker domain suggests that this domain may play a regulatory role similar to the R-domain of CFTR (the ABC transporter responsible for cystic fibrosis).

SEM L3: The SEM L3 cDNA open reading frame predicts a 407 amino acid polypeptide of 46.3 kD (FIG. 11). In vitro transcription—translation of SEM L3 cDNA resulted in a protein product with an apparent molecular weight of 46 kD which is in close agreement with the predicted weight of 46.3 kD.

Two nuclear targeting sequences, which are 100% conserved between man, mouse and cow, diverged slightly in the SEM L3 amino acid sequence. The first targeting site is the 21 amino acid N-terminal oligopeptide. The serine and arginine present at positions 13 and 19 respectively, in human, bovine and murine L3 are replaced with histidines in SEM L3 (FIG. 12). The second potential nuclear targeting site is the bipartite motif. Here the human, bovine and murine proteins have a KKR-$(aa)_{12}$-KRR at position 341–358 while the SEM L3 gene has KKR-$(aa)_{10}$-HHSRQ at position 341–358. The second half of this bipartite motif, while remaining basic, does not match those found in other nuclear targeting motifs (Simonic et al., supra. 1994). Overall, there is 77.2% amino acid identity between the SEM L3 and the consensus from the other mammalian L3 ribosomal genes, with 56% of the nucleotide differences between SEM L3 and the human L3 being silent.

hALR: hALR cDNA sequences encode a 119 amino acid protein which is 84.8% identical and 94.1% similar to the rat ALR protein (see, FIGS. 13 and 14).

Although the invention has been described with reference to the disclosed embodiments, it should be understood that various modifications can be made without departing from the spirit of the invention. Accordingly, the invention is limited only by the following claims.

SEQUENCE LISTING (1) GENERAL INFORMATION:

(iii) NUMBER OF SEQUENCES: 73

(2) INFORMATION FOR SEQ ID NO:1:

(i) SEQUENCE CHARACTERISTICS:
      (A) LENGTH: 179 amino acids
      (B) TYPE: amino acid
      (C) STRANDEDNESS: Not Relevant
      (D) TOPOLOGY: unknown (ii) MOLECULE TYPE: peptide (xi) SEQUENCE DESCRIPTION: SEQ ID NO:1:

```
Leu His Leu Glu Gly Pro Phe Ile Ser Arg Glu Lys Arg Gly Thr His
 1               5                  10                  15

Pro Glu Ala His Leu Arg Ser Phe Glu Ala Asp Ala Phe Gln Asp Leu
                20                  25                  30

Leu Ala Thr Tyr Gly Pro Leu Asp Asn Val Arg Ile Val Thr Leu Asp
                35                  40                  45
```

```
Pro Glu Leu Gly Arg Ser His Glu Val Phe Arg Thr Leu Thr Xaa Arg
    50                  55                  60

Ser Ile Cys Val Ser Leu Gly His Ser Val Ala Asp Leu Arg Ala Ala
65                  70                  75                  80

Glu Asp Ala Val Trp Ser Gly Ala Thr Phe Ile Thr His Leu Phe Asn
                    85                  90                  95

Ala Met Leu Pro Phe His His Arg Asp Pro Gly Ile Val Gly Leu Leu
                100                 105                 110

Thr Ser Asp Arg Pro Ala Gly Arg Cys Ile Phe Tyr Gly Met Ile Ala
                115                 120                 125

Asp Gly Thr His Thr Asn Pro Ala Ala Leu Arg Ile Ala His Arg Ala
                130                 135                 140

His Pro Gln Gly Leu Val Leu Val Thr Asp Ala Ile Pro Ala Leu Gly
145                 150                 155                 160

Leu Gly Asn Gly Arg His Thr Leu Gly Gln Gln Glu Val Glu Val Asp
                    165                 170                 175

Gly Leu Thr (2) INFORMATION FOR SEQ ID NO:2:

(i) SEQUENCE CHARACTERISTICS:
        (A) LENGTH: 90 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:2:

His Leu Glu Gly Pro Phe Ile Ser Lys Arg Gly His Pro Glu Ser Tyr
1               5                   10                  15

Gly Asn Ile Val Thr Pro Glu Leu Glu Val Ser Gly His Ser Ala Leu
                20                  25                  30

Glu Ala Val Ser Gly Ala Ile Thr His Leu Phe Asn Ala Met His His
                35                  40                  45

Arg Asp Pro Gly Gly Leu Leu Thr Ser Leu Tyr Gly Ile Asp Gly His
    50                  55                  60

Thr Ala Leu Arg Ile Ala Gly Leu Val Leu Val Thr Asp Ala Ile Ala
65                  70                  75                  80

Leu Gly Gly His Leu Gly Gln Val Gly Leu
                85                  90

(2) INFORMATION FOR SEQ ID NO:3:

(i) SEQUENCE CHARACTERISTICS:
        (A) LENGTH: 64 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:3:

Leu His Leu Glu Gly Pro Lys Gly Thr His Arg Ala Ala Asp Leu Asp
1               5                   10                  15

Val Thr Leu Pro Glu Glu Val Leu Ile Val Ser Gly His Ser Ala Leu
                20                  25                  30

Ala Gly Thr Phe Thr His Leu Asn Ala Met Pro Gly Leu Leu Ile Gly
                35                  40                  45
```

```
Ile Ala Asp Gly His Ala Arg Ala Arg Leu Leu Val Thr Asp Ala Gly
     50                  55                  60
```

(2) INFORMATION FOR SEQ ID NO:4:

(i) SEQUENCE CHARACTERISTICS:
        (A) LENGTH: 55 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:4:

```
Leu His Glu Pro Ser Glu Lys Gly His Arg Asp Leu Gly Asp Thr Glu
1                5                  10                  15

Ile Val Ser Gly His Ser Ala Ala Gly Ala Thr Phe Thr His Leu
             20                  25                  30

Asn Ala Met Pro Gly Gly Ile Asp Gly His Asn Arg Ile Leu Val Thr
             35                  40                  45

Asp Ile Ala Gly Leu Gly Thr
     50                  55
```

(2) INFORMATION FOR SEQ ID NO:5:

(i) SEQUENCE CHARACTERISTICS:
        (A) LENGTH: 49 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:5:

```
Cys Asp Cys His Pro Val Gly Ala Ala Gly Lys Thr Cys Asn Gln Thr
1                5                  10                  15

Thr Gly Gln Cys Pro Cys Lys Asp Gly Val Thr Gly Leu Thr Cys Asn
             20                  25                  30

Arg Cys Ala Pro Gly Phe Gln Gln Ser Arg Ser Pro Val Ala Pro Cys
             35                  40                  45

Val
```

(2) INFORMATION FOR SEQ ID NO:6:

(i) SEQUENCE CHARACTERISTICS:
        (A) LENGTH: 48 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:6:

```
Cys Asp Cys His Pro Val Gly Ala Ala Gly Lys Thr Cys Asn Gln Thr
1                5                  10                  15

Thr Gly Gln Cys Pro Cys Lys Asp Gly Val Thr Gly Leu Thr Cys Asn
             20                  25                  30

Arg Cys Ala Pro Gly Phe Gln Gln Ser Arg Ser Pro Val Ala Pro Cys
             35                  40                  45
```

(2) INFORMATION FOR SEQ ID NO:7:

(i) SEQUENCE CHARACTERISTICS:
        (A) LENGTH: 44 amino acids (B) TYPE: amino acid
            (C) STRANDEDNESS: Not Relevant
            (D) TOPOLOGY: unknown (ii) MOLECULE TYPE: peptide (xi) SEQUENCE DESCRIPTION: SEQ ID NO:7:

Cys Asp Cys His Pro Val Gly Ala Ala Gly Thr Cys Asn Gln Thr Thr
1               5                   10                  15

Gly Gln Cys Pro Cys Lys Asp Gly Val Thr Gly Thr Cys Asn Arg Cys
                20                  25                  30

Ala Lys Gly Gln Gln Ser Arg Ser Pro Ala Pro Cys
            35                  40

(2) INFORMATION FOR SEQ ID NO:8:

(i) SEQUENCE CHARACTERISTICS:
        (A) LENGTH: 35 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:8:

Cys Cys His Pro Val Gly Gly Cys Asn Gln Gly Gln Cys Cys Lys Gly
1               5                   10                  15

Val Thr Gly Thr Cys Asn Arg Cys Ala Lys Gly Gln Gln Ser Arg Ser
                20                  25                  30

Val Pro Cys
        35

(2) INFORMATION FOR SEQ ID NO:9:

(i) SEQUENCE CHARACTERISTICS:
        (A) LENGTH: 49 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:9:

His Ser Pro Ser Leu Ser Ala Glu Thr Pro Ile Pro Gly Pro Thr Glu
1               5                   10                  15

Asp Ser Ser Pro Val Gln Pro Gln Asp Cys Asp Ser His Cys Lys Pro
                20                  25                  30

Ala Arg Gly Ser Tyr Arg Ile Ser Leu Lys Lys Phe Cys Lys Lys Asp
            35                  40                  45

Tyr (2) INFORMATION FOR SEQ ID NO:10:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:10:

Ile Ser Pro Asp Cys Asp Ser Cys Lys Pro Ala Gly Tyr Ile Lys Lys
1               5                   10                  15

```
Cys Lys Lys Asp Tyr
            20

(2) INFORMATION FOR SEQ ID NO:11:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:11:

Pro Pro Thr Ser Ser Pro Asp Cys Asp Ser Cys Lys Gly Ile Lys Lys
1               5                   10                  15

Cys Lys Lys Asp Tyr
            20

(2) INFORMATION FOR SEQ ID NO:12:

(i) SEQUENCE CHARACTERISTICS:
        (A) LENGTH: 88 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:12:

Met Leu Val Gly Asp Ser Gly Val Gly Lys Thr Cys Leu Leu Val Arg
1               5                   10                  15

Phe Lys Asp Gly Ala Phe Leu Ala Gly Thr Phe Ile Ser Thr Val Gly
                20                  25                  30

Ile Asp Phe Arg Asn Lys Val Leu Asp Val Asp Gly Val Lys Ala Lys
            35                  40                  45

Leu Gln Met Trp Asp Thr Ala Gly Gln Glu Arg Phe Arg Ser Val Thr
        50                  55                  60

His Ala Tyr Tyr Arg Asp Ala His Ala Leu Leu Leu Tyr Asp Val
65                  70                  75                  80

Thr Asn Lys Ala Ser Phe Asp Asn
                85

(2) INFORMATION FOR SEQ ID NO:13:

(i) SEQUENCE CHARACTERISTICS:
        (A) LENGTH: 83 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:13:

Met Leu Val Gly Asp Ser Gly Val Gly Lys Thr Cys Leu Leu Val Arg
1               5                   10                  15

Phe Lys Asp Gly Ala Phe Leu Ala Gly Thr Phe Ile Ser Thr Val Gly
                20                  25                  30

Ile Asp Phe Arg Asn Lys Val Leu Asp Val Asp Gly Lys Lys Leu Gln
            35                  40                  45

Trp Asp Thr Ala Gly Gln Glu Arg Phe Arg Ser Val Thr His Ala Tyr
        50                  55                  60

Tyr Arg Asp Ala His Ala Leu Leu Leu Leu Tyr Asp Thr Asn Lys Ser
```

```
65                  70                  75                  80
```
Phe Asp Asn (2) INFORMATION FOR SEQ ID NO:14:

(i) SEQUENCE CHARACTERISTICS:
        (A) LENGTH: 83 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:14:

```
Phe Gln Asn His Phe Glu Pro Gly Val Tyr Val Cys Ala Lys Cys Gly
1               5                  10                  15

Tyr Glu Leu Phe Ser Ser Arg Ser Lys Tyr Ala His Ser Ser Pro Trp
                20                  25                  30

Pro Ala Phe Thr Glu Thr Ile His Ala Asp Ser Val Ala Lys Arg Pro
            35                  40                  45

Glu His Asn Arg Ser Glu Ala Leu Lys Val Ser Cys Gly Lys Cys Gly
        50                  55                  60

Asn Gly Leu Gly His Glu Phe Leu Asn Asp Gly Pro Lys Pro Gly Gln
65                  70                  75                  80

Ser Arg Phe
```

(2) INFORMATION FOR SEQ ID NO:15:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:15:

```
Phe Pro Gly Tyr Val Gly Leu Phe Ser Ser Lys Tyr Trp Pro Phe Thr
1               5                  10                  15

Ile Ala Ser Val Val Leu Gly His Phe Asp Gly Pro
                20                  25
```

(2) INFORMATION FOR SEQ ID NO:16:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:16:

```
Glu Gly Val Tyr Cys Ala Cys Asp Leu Ser Ser Lys Trp Pro Ala Phe
1               5                  10                  15

Glu Ala Cys Cys Leu Gly His Phe Gly Lys
                20                  25
```

(2) INFORMATION FOR SEQ ID NO:17:

(i) SEQUENCE CHARACTERISTICS:
        (A) LENGTH: 32 amino acids
        (B) TYPE: amino acid
        (C) STRANDEDNESS: Not Relevant (D) TOPOLOGY: unknown (ii) MOLECULE TYPE: peptide (xi) SEQUENCE DESCRIPTION: SEQ ID NO:17:

Phe His Phe Glu Gly Tyr Val Cys Cys Gly Glu Leu Phe Ser Lys Trp
1               5                   10                  15

Pro Ala Phe Glu Val Cys Cys Leu Gly His Phe Asn Asp Gly Pro Lys
            20                  25                  30

(2) INFORMATION FOR SEQ ID NO:18:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:18:

Phe Gly Tyr Val Gly Phe Ser Ser Lys Trp Pro Phe Thr Ile Asp Val
1               5                   10                  15

Gly Asn Leu Gly His Phe Asp Gly Pro Lys Gly Arg
            20                  25

(2) INFORMATION FOR SEQ ID NO:19:

(i) SEQUENCE CHARACTERISTICS:
        (A) LENGTH: 6803 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGAGCTCGGT TGGAAACCCC CCGAGGCATA ATAGGCGCTC GATAAATGTG CAATAGGTGA        60

ACATGTGGTG GCTTGCAGGC GTCTGGGGGG AGACAGCAGG TTCTGGGCTG GGCAGGGAAT       120

TATTGGATCA ACGGGCATCT TACAGGAAAG ACTCTCAGCT CCCTGCCGCC TAGGACTGTC       180

CAGCCCATCT ATGCCCTCTC CCCAGCCTGT GCCCCAAAGC TGGAGCTGCC ACTCTAGGGG       240

TGAGGGGTGG GGTGGGGAGG GGGAGGCGAA GCACTGCGGC CTGAGTTGCA GGTGGGGGGA       300

GGGGAGGCGG AGCTTCTTTG TTGCAGAAGG TGCCAGGAGG GGGCAGGGCC AGTGGAGAGG       360

TGGGAGGTGG GAGAGGCCCC AGCCAGGGGC TGGGACAGGT GGCTGGGTCC CTGGGGAGCA       420

ATAAGTCCCG CTTGGGCGCT GTGGGGAGGC CCTTCCTAAC TCCCAAACAC CATCTGTGAG       480

GGCTGGGGGT GGGGGCAGAG TAGCGTGTGC AGAGGACTGT TCCTGGGGAG AGGCCCTGTG       540

ACCAGCGGCC TCCTCCCTGG GGAGCTGGCG GTACAATGGC CCTCTGGGCC CACGGCCTCC       600

CGCCGCTGCT GCTGACCCAG ATGAACAATT GGGGCAGGGC TGAGCCCCAG GCACCTACTT       660

TCCCCCACCC CAGAAGCCAC CAGACGTTCT GCAGACCCCA GTCCTGGCTC ACAGGGAAGC       720

TGAGCTGGAG ACAAAGCCAG CCCCTCTGAT GAGGGTGGAA GAGGCTGCTG GCCACTGTCC       780

CTCTTGCAGC CTGGCTGGCA GCCAGTCTGG CAGTGGCCCT GACGTCCAGA GACAGCTTGG       840

GTTTCCCCAG AGGCTTGTCT CTGGCCAGTG GGACCCCTCT GTCAGGCCTG GCTTTTCTC       900

TCCACTGTCC CAGAATGATG ATCTCAGCCC CCATAGTCCC CCCAGGGTTC CTCCCACCCT       960

TAGGGTGGGG TGTCGGGGGG TGGGGGTTGG GAGCCAGAAG GACCTTGAAG AGGGTGGTTG      1020

GGACGTTTCA GGTTCTAAGC TTGACCCACA GAGCGGAGCG TGAGCCCCGT CAGGTTGAGG      1080

-continued

```
TCCCTCAACT TGTAAAGGAC ACAATTCCAT TCTCTTTATC AGGAAGCTGA GGGGCAGGGG      1140

CCCTGTGGCA GAGAGAGAGC CCCTTAGCCC TCTCTGTTCA GTCCTCCGGT GCCCCCATCC      1200

CTGTGCATCT GTGGCTGTCA CATGCAGATG TGTGGCAAGG AGAAGGTGCC CACCAGCCAG      1260

TGTCAGTTGC TCCAGGAGCC AAGCCAGGTG CCCTATCACC CTGTCTTCCC GTTCCTCCCC      1320

TCCATGGTCA GGCCCTCCTG CTCCCTCCTC TGGTCCTTCA GTTTCCCCTA GGAGGCTTCC      1380

GTGTCCTCCT GCCCCTCCTC TCCCCAACAG CGGGATGCGT CTACCTCTCC ATTCTCTTCC      1440

TCCTGGTCCT TGCTCATCTC TGGTCGTGTC CAGGGTAGCA CCCACGTGGC CTCCTCCACC      1500

AGCTGCAGGC CTGGCCTCCC ATCTGAAACG GGGCATTCAG GCCTCGATGC TGGCCCTGCA      1560

CGGAACTTGT TCCCTGCCCC TCCCTGGGAT GCTTGGCCTC CTCTGTCAAG GACCTGAAAG      1620

TCGGAGGGGA GGAGGTTTCT CTGACCAGAG CTGTTCCTGG ACCCTCTTTG GTGGTGTCGC      1680

TCCCAGGCAC AGCTACCCCA TCCCCAGCTA GTCCCCAGGC CACCCAGCTG GCTTCTGCC      1740

TCAGTTTCCC TGCCCAAACG TGCTGTGACG TAGGGCAGTG GGCTCCGGGT TGCGACCAGC      1800

CCCTTCCCAT GATTAAACCC TACTCCCTGC CCCTGCAGAG GGGTCCTCAA CAGCTAACCA      1860

AGCCCCCGAA CCCCAAGAAG CCACCCCATC CCACCCTCCA GCTTCCATGT CCTCCCTGCC      1920

AGCTGGGCCC GTGGCAGAGG TGCCCCTAGA AACTTGCAGA CCCAGGGAGC TTTGGGATCA      1980

GAATCTGGCC TGGTGCAGGG GATGCTGGCC TCATGTCTTA GCCCAGCTCA GGCCCATGGG      2040

GGTGCCCCCC TTCCTCAACA TGGGCAGGAG ACACTCCAAT TTGTGCAGCT CTCGACTTGG      2100

GCCTGATGCC ACTTGAGACT CATCAAATCC AACAGCTTCA GAGCGCGTGC TGAGTAACAG      2160

GCATCTGGCA GGTGAGGAAA CAGGAGCCCA AGACATGCAG CCAGAAATGG GGCAGTTGGA      2220

TTCAAAATTA GACCTGACCG AATCCTGGGT TCCTTCTACT CGAGTAGATG CTGCTTTGGG      2280

GATGACCCTT CAACTGGTGG TTACTTGGCT TCCCTACCTG GGGAACATCC AGGGCCTCTG      2340

CTGTCAGACC CGGGGCCTTG CCTGCCTGAT GGTCTTCAGG GAGGAGGCGA CCCAGACCCC      2400

CGTCCAGCAC GTGGCACAGC CCCAGGAGCA GTAAAGACCT GGCTGTGGGC CCAGGACCCT      2460

GCTGGGTGGT CCCCCACGGG CTGCGAAGGC TGAGCTGCCC CCTCCAGAC CCCTCCCGCC      2520

AGCGCATTCC TGGCTCCCCG GCCCCTCCCC TGGCTCCCGG GCCTCCCAGC CCCCTTCCCC      2580

GCTGGCCCAG CCCGCGTCTG AATCTGCTTC TGATTCCAGC TCTGCGATGA GGCCCCCTCC      2640

CCTCCCCTGC CTCCTTCCCG ACCCGAGCAG CCCCGCCCCC GGCTGGGCCC GGGCTTGCGC      2700

CTGCTGCGCC CCCCACCCCC TCCTGGCACA GCTCGTCCGC CCTCGCTGCA GCCGGGAGGA      2760

GGCGGCGGCC CGTGCACCGC AGGCCCCGCC CGCCCACGGC CCTTCCCGGG AGGCCGGGAG      2820

ACCTGCTCCG CCCCGGCCCTC GGTGGGTGAG TGCGAGCGGC GGGTGGGGCC TCCGCGGGCG      2880

GAGGCACCGG GAGCGGGGGC GACGCCTGTC ATCGCTCTAG GCCCAGCGGG AGGACGCGCC      2940

AACATCCCCG CTGCTGTGCT GGGCCGGGG CGTGCCCGCC GCTGCTCCCA CCTCTGGGCC      3000

GGGCTGGGGC CGCCCGGGGG CCCTGTTCCT CGGCATTGCG GGCCTGGTGG GCAGAGCCGC      3060

GGAGAGGGCT TCTTTTCCCC AAGGGCAGCG TCTTGGGGCC CGGCCACTGG CTGACCCGCA      3120

GCGGCTCCGG CCATGCCTGG CTGGCCCTGG GGCTGCTGC TGACGGCAGG CACGCTCTTC      3180

GCCGCCCTGA GTCCTGGGCC GCCGGCGCCC GCCGACCCCT GCCACGATGA GGGGGGTGCG      3240

CCCCGCGGCT GCGTGCCAGG ACTGGTGAAC GCCGCCCTGG GCCGCGAGGT GCTGGCTTCC      3300

AGCACGTGCG GGCGGCCGGC CACTCGGGCC TGCGACGCCT CCGACCCGCG ACGGGCACAC      3360

TCCCCCGCCC TCCTTACTTC CCCAGGGGGC ACGGCCAGCC CTCTGTGCTG GCGCTCGGAG      3420
```

-continued

```
TCCCTGCCTC GGGCGCCCCT CAACGTGACT CTCACGGTGC CCCTGGGCAA GGCTTTTGAG    3480

CTGGTCTTCG TGAGCCTGCG CTTCTGCTCA GCTCCCCCAG CCTCCGTGGC CCTGCTCAAG    3540

TCTCAGGACC ATGGCCGCAG CTGGGCCCCG CTGGGCTTCT TCTCCTCCCA CTGTGACCTG    3600

GACTATGGCC GTCTGCCTGC CCCTGCCAAT GGCCCAGCTG GCCCAGGGCC TGAGGCCCTG    3660

TGCTTCCCCG CACCCCTGGC CCAGCCTGAT GGCAGCGGCC TTCTGGCCTT CAGCATGCAG    3720

GACAGCAGCC CCCCAGGCCT GGACCTGGAC AGCAGCCCAG TGCTCCAAGA CTGGGTGACC    3780

GCCACCGACG TCCGTGTAGT GCTCACAAGG CCTAGCACGG CAGGTGACCC CAGGGACATG    3840

GAGGCCGTCG TCCCTTACTC CTACGCAGCC ACCGACCTCC AGGTGGGCGG GCGCTGCAAG    3900

TGCAATGGAC ATGCCTCACG GTGCCTGCTG GACACACAGG GCCACCTGAT CTGCGACTGT    3960

CGGCATGGCA CCGAGGGCCC TGACTGCGGC CGCTGCAAGC CCTTCTACTG CGACAGGCCA    4020

TGGCAGCGGG CCACTGCCCG GGAATCCCAC GCCTGCCTCG GTGAGGCCTT GGAGGGTGGC    4080

CTGGGGACCT TGGACACAAC CAGCCTGCCC CTGACCCATC CCTCCCTGCA GCTTGCTCCT    4140

GCAACGGCCA TGCCCGCCGC TGCCGCTTCA ACATGGAGCT GTACCGACTG TCCGCCGCC    4200

GCAGCGGGGG TGTCTGTCTC AACTGCCGGC ACAACACCGC CGGCCGCCAC TGCCACTACT    4260

GCCGGGAGGG CTTCTATCGA GACCCTGGCC GTGCCCTGAG TGACCGTCGG GCTTGCAGGG    4320

GTGAGCCACC ACCGGCCACC TGCAGGCCCT CACCCTCTGA CTTCCCAGAT CCCCAGACAG    4380

GCTTCTGACC AGGCCCTTCC CACCTCTGTC CTCAGCCTGC GACTGTCACC CGGTTGGTGC    4440

TGCTGGCAAG ACCTGCAACC AGACCACAGG CCAGTGTCCC TGCAAGGATG GCGTCACTGG    4500

CCTCACCTGC AACCGCTGCG CGCCTGGCTT CCAGCAAAGC CGCTCCCCAG TGGCGCCCTG    4560

TGTTAGTGAG TGACCCTGCC CCGCCTCAGC CACCAAGCCA AGGCCACCCC AGCTCCCTGC    4620

TGTTGTCCCG TCTATTCCCC GAGCCCTGCA GATCTCTCTG CCCCTCCATC GCAGGCCATT    4680

CTCCCTCCCT CTCTGCAGAG ACCCCTATCC CTGGACCCAC TGAGGACAGC AGCCCTGTGC    4740

AGCCCCAGGG TGAGTGGACA CAGGACAGGG CCCCAGACTG GCATGACTTT GGGGGAGGGG    4800

GCTCTGGGAG GAGAGGGTGG GGAAAGGGAG TCTGTGCCAG CCTCCCACCT TCTACCCAGA    4860

CTGTGACTCG CACTGCAAAC CTGCCCGTGG CAGCTACCGC ATCAGCCTAA GAAGTTCTG    4920

CAAGAAGGAC TATGGTAGGT GCCCTCAGGC CTCCCGCGGA CCTTCCCACC TTCCTCCTCT    4980

CCCTACCTTC CCTCCTCCGC CAGCTTCCCC TTGGAACGCC TTGACCCTTG CTGGGCCCCA    5040

AGGCCCATCC TCATCCCTCA GGTCCTCCAC GGGCAGCGAC CCCGCCCCTT CAGCCCCCAC    5100

TGCCCTCCTG GTGTCCTCCC CGTGCCTCCC CCTACCGCGG GCAGGCCGCC CCTTCCTGAC    5160

CCCGCCCCCT CTCGCTCTCC CCGCAGCGGT GCAGGTGGCG GTGGGTGCGC GCGGCGAGGC    5220

GCGCGGCGCG TGGACACGCT TCCCGGTGGC GGTGCTCGCC GTGTTCCGGA GCGGAGAGGA    5280

GCGCGCGCGG CGCGGGAGTA GCGCGCTGTG GGTGCCCGCC GGGGATGCGG CCTGCGGCTG    5340

CCCGCGCCTG CTCCCCGGCC GCCGCTACCT CCTGCTGGGG GGCGGGCCTG GAGCCGCGGC    5400

TGGGGGCGCG GGGGGCCGGG GGCCCGGGCT CATCGCCGCC CGCGGAAGCC TCGTGCTACC    5460

CTGGAGGGAC GCGTGGACGC GGCGCCTGCG GAGGCTGCAG CGACGCGAAC GGCGGGGGCG    5520

CTGCAGCGCC GCCTGAGCCC GCCGGCTGGG CAGGGCGGCC GCTGCTCCCA CATCTAGGCG    5580

CACGTTCACC CTGTGCCTTC GCCTGCCAAG GAGTCCTTGC TCGCGTCGCG CGTGTCGCCA    5640

CCTGGGCCGC CGCCCCGTCC CCGCCGGCAG CTCCCTCGGT ACCTCCCGTC TGGCCCTGGG    5700

GGGATGTGAC CGGCGCACGG ACAGCCCGCC CCGCACAGAG GCAGATGATA TGGCACACCC    5760

GGAGGACCCC ATGGTCTCCC GCCCTCTGGC TGTCGGCCCT GTCCCAGGGG CACTGGGATA    5820
```

```
CCCGGAAGGC TGTGAATCCT TCGTGATGCC GGGCCCTCTC GGGGATCTCA GATCATCCCC    5880

GGGGCCGCTG TGATGCACCC CCACCTGTGC GGCGACCCGC CAGGAGCGCA CTGACCTCCC    5940

CAAAGACTGT GGCCACCGCA GGCGCCTTGG ACCCCCATGG GGGACAGGGC GTCCCCTGCC    6000

TCCTGCAGCC CCACGAGGGC GGCGGCCTTG GCCCTGCGGC TGGGCGTCCG CGTCCGGGCG    6060

CCCCGCGGCG TCTGCTGCCG GGTCCCGTAA CTTTCTTGGC CGCCTGTGTC CCCGTCTGCC    6120

GGCTCCGTCC GGCCGTCCCT CTCTCTGCCG CGTCTCTGAC CCTCGGCGCC ACAGCTCCTC    6180

AGCTCAGGGC CCGTCCCAGA ACCTCCTTCC AGCCCTTCTC CCCCGACTCG GGAAGGGACG    6240

TCGTGCCCAC GCGGTTCCGG ATCCACGCGT GACCCGGCCG GACCGCGACT CCGACAGGCG    6300

GCTGTCCGGG CCCCCGATGC CCTCGGCAGG GCCGTGCCAC CCCCCGCCCC TTGTTGTCCC    6360

CCCGGGACCG GCACTGCCGT TTGCCTCCTC TCCGCACGGG ACCGGTTCCC GGCCGGCCCC    6420

AGCTTCCGCC GCTGCGGCCG CCGACCGTCA GCGCGCATGC CCAGAGCCGG GCAGGCCGGA    6480

GCCCCGCCGG CTCTCCGGGG TGGGCACAGG GCGACAGCTC GGCGGGGGCG GGGCCGAGCA    6540

CGCGCGTGCG CAGAAAGGCC GGCGCGGCAG GCTGAGGAGA AAGCGGCGCG CGGAGGTGGG    6600

TGCGCTCGGG GCGTGCGGGG GGCGCGCGGC GGGGTGGCGG GTGGCGGGGC CGGGTCCCCG    6660

CTGTCACCGG GGTCGGCGCG TGCTGGGGGC GGGAGCGTGG GGGCCGGGCT GCGTGCCCCA    6720

TTCGAGGCGG GGATCCCCGG CCACGCGCGG GTTGGGGGCT CCAGAGCCCG GCACCGCCCG    6780

GCGCTGCAGC TGCGGCTTGG CCT                                           6803

(2) INFORMATION FOR SEQ ID NO:20:

(i) SEQUENCE CHARACTERISTICS:
        (A) LENGTH: 1743 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1740

(xi) SEQUENCE DESCRIPTION: SEQ ID NO:20:

ATG CCT GGC TGG CCC TGG GGG CTG CTG CTG ACG GCA GGC ACG CTC TTC       48
Met Pro Gly Trp Pro Trp Gly Leu Leu Leu Thr Ala Gly Thr Leu Phe
 1               5                  10                  15

GCC GCC CTG AGT CCT GGG CCG CCG GCG CCC GCC GAC CCC TGC CAC GAT       96
Ala Ala Leu Ser Pro Gly Pro Pro Ala Pro Ala Asp Pro Cys His Asp
                20                  25                  30

GAG GGG GGT GCG CCC CGC GGC TGC GTG CCA GGA CTG GTG AAC GCC GCC      144
Glu Gly Gly Ala Pro Arg Gly Cys Val Pro Gly Leu Val Asn Ala Ala
             35                  40                  45

CTG GGC CGC GAG GTG CTG GCT TCC AGC ACG TGC GGG CGG CCG GCC ACT      192
Leu Gly Arg Glu Val Leu Ala Ser Ser Thr Cys Gly Arg Pro Ala Thr
         50                  55                  60

CGG GCC TGC GAC GCC TCC GAC CCG CGA CGG GCA CAC TCC CCC GCC CTC      240
Arg Ala Cys Asp Ala Ser Asp Pro Arg Arg Ala His Ser Pro Ala Leu
 65                  70                  75                  80

CTT ACT TCC CCA GGG GGC ACG GCC AGC CCT CTG TGC TGG CGC TCG GAG      288
Leu Thr Ser Pro Gly Gly Thr Ala Ser Pro Leu Cys Trp Arg Ser Glu
                 85                  90                  95

TCC CTG CCT CGG GCG CCC CTC AAC GTG ACT CTC ACG GTG CCC CTG GGC      336
Ser Leu Pro Arg Ala Pro Leu Asn Val Thr Leu Thr Val Pro Leu Gly
                100                 105                 110
```

-continued

```
AAG GCT TTT GAG CTG GTC TTC GTG AGC CTG CGC TTC TGC TCA GCT CCC      384
Lys Ala Phe Glu Leu Val Phe Val Ser Leu Arg Phe Cys Ser Ala Pro
            115                 120                 125

CCA GCC TCC GTG GCC CTG CTC AAG TCT CAG GAC CAT GGC CGC AGC TGG      432
Pro Ala Ser Val Ala Leu Leu Lys Ser Gln Asp His Gly Arg Ser Trp
        130                 135                 140

GCC CCG CTG GGC TTC TTC TCC TCC CAC TGT GAC CTG GAC TAT GGC CGT      480
Ala Pro Leu Gly Phe Phe Ser Ser His Cys Asp Leu Asp Tyr Gly Arg
145                 150                 155                 160

CTG CCT GCC CCT GCC AAT GGC CCA GCT GGC CCA GGG CCT GAG GCC CTG      528
Leu Pro Ala Pro Ala Asn Gly Pro Ala Gly Pro Gly Pro Glu Ala Leu
                165                 170                 175

TGC TTC CCC GCA CCC CTG GCC CAG CCT GAT GGC AGC GGC CTT CTG GCC      576
Cys Phe Pro Ala Pro Leu Ala Gln Pro Asp Gly Ser Gly Leu Leu Ala
            180                 185                 190

TTC AGC ATG CAG GAC AGC AGC CCC CCA GGC CTG GAC CTG GAC AGC AGC      624
Phe Ser Met Gln Asp Ser Ser Pro Pro Gly Leu Asp Leu Asp Ser Ser
        195                 200                 205

CCA GTG CTC CAA GAC TGG GTG ACC GCC ACC GAC GTC CGT GTA GTG CTC      672
Pro Val Leu Gln Asp Trp Val Thr Ala Thr Asp Val Arg Val Val Leu
    210                 215                 220

ACA AGG CCT AGC ACG GCA GGT GAC CCC AGG GAC ATG GAG GCC GTC GTC      720
Thr Arg Pro Ser Thr Ala Gly Asp Pro Arg Asp Met Glu Ala Val Val
225                 230                 235                 240

CCT TAC TCC TAC GCA GCC ACC GAC CTC CAG GTG GGC GGG CGC TGC AAG      768
Pro Tyr Ser Tyr Ala Ala Thr Asp Leu Gln Val Gly Gly Arg Cys Lys
                245                 250                 255

TGC AAT GGA CAT GCC TCA CGG TGC CTG CTG GAC ACA CAG GGC CAC CTG      816
Cys Asn Gly His Ala Ser Arg Cys Leu Leu Asp Thr Gln Gly His Leu
            260                 265                 270

ATC TGC GAC TGT CGG CAT GGC ACC GAG GGC CCT GAC TGC GGC CGC TGC      864
Ile Cys Asp Cys Arg His Gly Thr Glu Gly Pro Asp Cys Gly Arg Cys
        275                 280                 285

AAG CCC TTC TAC TGC GAC AGG CCA TGG CAG CGG GCC ACT GCC CGG GAA      912
Lys Pro Phe Tyr Cys Asp Arg Pro Trp Gln Arg Ala Thr Ala Arg Glu
    290                 295                 300

TCC CAC GCC TGC CTC GCT TGC TCC TGC AAC GGC CAT GCC CGC CGC TGC      960
Ser His Ala Cys Leu Ala Cys Ser Cys Asn Gly His Ala Arg Arg Cys
305                 310                 315                 320

CGC TTC AAC ATG GAG CTG TAC CGA CTG TCC GGC CGC CGC AGC GGG GGT     1008
Arg Phe Asn Met Glu Leu Tyr Arg Leu Ser Gly Arg Arg Ser Gly Gly
                325                 330                 335

GTC TGT CTC AAC TGC CGG CAC AAC ACC GCC GGC CGC CAC TGC CAC TAC     1056
Val Cys Leu Asn Cys Arg His Asn Thr Ala Gly Arg His Cys His Tyr
            340                 345                 350

TGC CGG GAG GGC TTC TAT CGA GAC CCT GGC CGT GCC CTG AGT GAC CGT     1104
Cys Arg Glu Gly Phe Tyr Arg Asp Pro Gly Arg Ala Leu Ser Asp Arg
        355                 360                 365

CGG GCT TGC AGG GCC TGC GAC TGT CAC CCG GTT GGT GCT GCT GGC AAG     1152
Arg Ala Cys Arg Ala Cys Asp Cys His Pro Val Gly Ala Ala Gly Lys
    370                 375                 380

ACC TGC AAC CAG ACC ACA GGC CAG TGT CCC TGC AAG GAT GGC GTC ACT     1200
Thr Cys Asn Gln Thr Thr Gly Gln Cys Pro Cys Lys Asp Gly Val Thr
385                 390                 395                 400

GGC CTC ACC TGC AAC CGC TGC GCG CCT GGC TTC CAG CAA AGC CGC TCC     1248
Gly Leu Thr Cys Asn Arg Cys Ala Pro Gly Phe Gln Gln Ser Arg Ser
                405                 410                 415

CCA GTG GCG CCC TGT GTT AAG ACC CCT ATC CCT GGA CCC ACT GAG GAC     1296
Pro Val Ala Pro Cys Val Lys Thr Pro Ile Pro Gly Pro Thr Glu Asp
```

-continued

```
                        420                       425                       430
AGC AGC CCT GTG CAG CCC CAG GAC TGT GAC TCG CAC TGC AAA CCT GCC          1344
Ser Ser Pro Val Gln Pro Gln Asp Cys Asp Ser His Cys Lys Pro Ala
            435                       440                       445

CGT GGC AGC TAC CGC ATC AGC CTA AAG AAG TTC TGC AAG AAG GAC TAT          1392
Arg Gly Ser Tyr Arg Ile Ser Leu Lys Lys Phe Cys Lys Lys Asp Tyr
        450                       455                       460

GCG GTG CAG GTG GCG GTG GGT GCG CGC GGC GAG GCG CGC GGC GCG TGG          1440
Ala Val Gln Val Ala Val Gly Ala Arg Gly Glu Ala Arg Gly Ala Trp
465                       470                       475                       480

ACA CGC TTC CCG GTG GCG GTG CTC GCC GTG TTC CGG AGC GGA GAG GAG          1488
Thr Arg Phe Pro Val Ala Val Leu Ala Val Phe Arg Ser Gly Glu Glu
                    485                       490                       495

CGC GCG CGG CGC GGG AGT AGC GCG CTG TGG GTG CCC GCC GGG GAT GCG          1536
Arg Ala Arg Arg Gly Ser Ser Ala Leu Trp Val Pro Ala Gly Asp Ala
                500                       505                       510

GCC TGC GGC TGC CCG CGC CTG CTC CCC GGC CGC CGC TAC CTC CTG CTG          1584
Ala Cys Gly Cys Pro Arg Leu Leu Pro Gly Arg Arg Tyr Leu Leu Leu
            515                       520                       525

GGG GGC GGG CCT GGA GCC GCG GCT GGG GGC GCG GGG GGC CGG GGG CCC          1632
Gly Gly Gly Pro Gly Ala Ala Gly Gly Ala Gly Gly Arg Gly Pro
        530                       535                       540

GGG CTC ATC GCC GCC CGC GGA AGC CTC GTG CTA CCC TGG AGG GAC GCG          1680
Gly Leu Ile Ala Ala Arg Gly Ser Leu Val Leu Pro Trp Arg Asp Ala
545                       550                       555                       560

TGG ACG CGG CGC CTG CGG AGG CTG CAG CGA CGC GAA CGG CGG GGG CGC          1728
Trp Thr Arg Arg Leu Arg Arg Leu Gln Arg Arg Glu Arg Arg Gly Arg
                    565                       570                       575

TGC AGC GCC GCC TGA                                                       1743
Cys Ser Ala Ala
            580

(2) INFORMATION FOR SEQ ID NO:21:

(i) SEQUENCE CHARACTERISTICS:
        (A) LENGTH: 580 amino acids
        (B) TYPE: amino acid
        (D) TOPOLOGY: linear (ii) MOLECULE TYPE: protein (xi) SEQUENCE DESCRIPTION: SEQ ID NO:21:

Met Pro Gly Trp Pro Trp Gly Leu Leu Leu Thr Ala Gly Thr Leu Phe
  1               5                  10                  15

Ala Ala Leu Ser Pro Gly Pro Ala Pro Ala Asp Pro Cys His Asp
                 20                  25                  30

Glu Gly Gly Ala Pro Arg Gly Cys Val Pro Gly Leu Val Asn Ala Ala
             35                  40                  45

Leu Gly Arg Glu Val Leu Ala Ser Ser Thr Cys Gly Arg Pro Ala Thr
         50                  55                  60

Arg Ala Cys Asp Ala Ser Asp Pro Arg Arg Ala His Ser Pro Ala Leu
 65                  70                  75                  80

Leu Thr Ser Pro Gly Gly Thr Ala Ser Pro Leu Cys Trp Arg Ser Glu
                 85                  90                  95

Ser Leu Pro Arg Ala Pro Leu Asn Val Thr Leu Thr Val Pro Leu Gly
                100                 105                 110

Lys Ala Phe Glu Leu Val Phe Val Ser Leu Arg Phe Cys Ser Ala Pro
            115                 120                 125

Pro Ala Ser Val Ala Leu Leu Lys Ser Gln Asp His Gly Arg Ser Trp
```

-continued

```
            130                 135                 140
Ala Pro Leu Gly Phe Phe Ser Ser His Cys Asp Leu Asp Tyr Gly Arg
145                 150                 155                 160
Leu Pro Ala Pro Ala Asn Gly Pro Ala Gly Pro Gly Pro Glu Ala Leu
                165                 170                 175
Cys Phe Pro Ala Pro Leu Ala Gln Pro Asp Gly Ser Gly Leu Leu Ala
            180                 185                 190
Phe Ser Met Gln Asp Ser Ser Pro Pro Gly Leu Asp Leu Asp Ser Ser
        195                 200                 205
Pro Val Leu Gln Asp Trp Val Thr Ala Thr Asp Val Arg Val Val Leu
    210                 215                 220
Thr Arg Pro Ser Thr Ala Gly Asp Pro Arg Asp Met Glu Ala Val Val
225                 230                 235                 240
Pro Tyr Ser Tyr Ala Ala Thr Asp Leu Gln Val Gly Gly Arg Cys Lys
                245                 250                 255
Cys Asn Gly His Ala Ser Arg Cys Leu Leu Asp Thr Gln Gly His Leu
            260                 265                 270
Ile Cys Asp Cys Arg His Gly Thr Glu Gly Pro Asp Cys Gly Arg Cys
        275                 280                 285
Lys Pro Phe Tyr Cys Asp Arg Pro Trp Gln Arg Ala Thr Ala Arg Glu
    290                 295                 300
Ser His Ala Cys Leu Ala Cys Ser Cys Asn Gly His Ala Arg Arg Cys
305                 310                 315                 320
Arg Phe Asn Met Glu Leu Tyr Arg Leu Ser Gly Arg Arg Ser Gly Gly
                325                 330                 335
Val Cys Leu Asn Cys Arg His Asn Thr Ala Gly Arg His Cys His Tyr
            340                 345                 350
Cys Arg Glu Gly Phe Tyr Arg Asp Pro Gly Arg Ala Leu Ser Asp Arg
        355                 360                 365
Arg Ala Cys Arg Ala Cys Asp Cys His Pro Val Gly Ala Ala Gly Lys
    370                 375                 380
Thr Cys Asn Gln Thr Thr Gly Gln Cys Pro Cys Lys Asp Gly Val Thr
385                 390                 395                 400
Gly Leu Thr Cys Asn Arg Cys Ala Pro Gly Phe Gln Gln Ser Arg Ser
                405                 410                 415
Pro Val Ala Pro Cys Val Lys Thr Pro Ile Pro Gly Pro Thr Glu Asp
            420                 425                 430
Ser Ser Pro Val Gln Pro Gln Asp Cys Asp Ser His Cys Lys Pro Ala
        435                 440                 445
Arg Gly Ser Tyr Arg Ile Ser Leu Lys Lys Phe Cys Lys Lys Asp Tyr
    450                 455                 460
Ala Val Gln Val Ala Val Gly Ala Arg Gly Glu Ala Arg Gly Ala Trp
465                 470                 475                 480
Thr Arg Phe Pro Val Ala Val Leu Ala Val Phe Arg Ser Gly Glu Glu
                485                 490                 495
Arg Ala Arg Arg Gly Ser Ser Ala Leu Trp Val Pro Ala Gly Asp Ala
            500                 505                 510
Ala Cys Gly Cys Pro Arg Leu Leu Pro Gly Arg Arg Tyr Leu Leu Leu
        515                 520                 525
Gly Gly Gly Pro Gly Ala Ala Gly Gly Ala Gly Gly Arg Gly Pro
    530                 535                 540
Gly Leu Ile Ala Ala Arg Gly Ser Leu Val Leu Pro Trp Arg Asp Ala
545                 550                 555                 560
```

-continued

```
Trp Thr Arg Arg Leu Arg Arg Leu Gln Arg Arg Glu Arg Arg Gly Arg
            565                 570                 575

Cys Ser Ala Ala
            580
```

(2) INFORMATION FOR SEQ ID NO:22:

(i) SEQUENCE CHARACTERISTICS:
        (A) LENGTH: 606 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:22:

```
Met Pro Arg Arg Gly Ala Glu Gly Pro Leu Ala Leu Leu Leu Ala Ala
1               5                   10                  15

Ala Trp Leu Ala Gln Pro Leu Arg Gly Gly Tyr Pro Gly Leu Asn Met
            20                  25                  30

Phe Ala Val Gln Thr Ala Gln Pro Asp Pro Cys Tyr Asp Glu His Gly
        35                  40                  45

Leu Pro Arg Arg Cys Ile Pro Asp Phe Val Asn Ser Ala Phe Gly Lys
    50                  55                  60

Glu Val Lys Val Ser Ser Thr Cys Gly Lys Pro Pro Ser Arg Tyr Cys
65                  70                  75                  80

Val Val Thr Glu Lys Gly Glu Gln Val Arg Ser Cys His Leu Cys
                85                  90                  95

Asn Ala Ser Asp Pro Lys Arg Ala His Pro Pro Ser Phe Leu Thr Asp
            100                 105                 110

Leu Asn Asn Pro His Asn Leu Thr Cys Trp Gln Ser Asp Ser Tyr Val
        115                 120                 125

Gln Tyr Pro His Asn Val Thr Leu Thr Leu Ser Leu Gly Lys Lys Phe
    130                 135                 140

Glu Val Thr Tyr Val Ser Leu Gln Phe Cys Ser Pro Arg Pro Glu Ser
145                 150                 155                 160

Met Ala Ile Tyr Lys Ser Met Asp Tyr Gly Lys Thr Trp Val Pro Phe
                165                 170                 175

Gln Phe Tyr Ser Thr Gln Cys Arg Lys Met Tyr Asn Lys Pro Ser Arg
            180                 185                 190

Ala Ala Ile Thr Lys Gln Asn Glu Gln Glu Ala Ile Cys Thr Asp Ser
        195                 200                 205

His Thr Asp Val Arg Pro Leu Ser Gly Gly Leu Ile Ala Phe Ser Thr
    210                 215                 220

Leu Asp Gly Arg Pro Thr Ala His Asp Phe Asp Asn Ser Pro Val Leu
225                 230                 235                 240

Gln Asp Trp Val Thr Ala Thr Asp Ile Lys Val Thr Phe Ser Arg Leu
                245                 250                 255

His Thr Phe Gly Asp Glu Asn Glu Asp Asp Ser Glu Leu Ala Arg Asp
            260                 265                 270

Ser Tyr Phe Tyr Ala Val Ser Asp Leu Gln Val Gly Gly Arg Cys Lys
        275                 280                 285

Cys Asn Gly His Ala Ser Arg Cys Val Arg Asp Arg Asp Asp Asn Leu
    290                 295                 300

Val Cys Asp Cys Lys His Asn Thr Ala Gly Pro Glu Cys Asp Arg Cys
305                 310                 315                 320
```

-continued

```
Lys Pro Phe His Tyr Asp Arg Pro Trp Gln Arg Ala Thr Ala Arg Glu
            325                 330                 335

Ala Asn Glu Cys Val Ala Cys Asn Cys Asn Leu His Ala Arg Arg Cys
        340                 345                 350

Arg Phe Asn Met Glu Leu Tyr Lys Leu Ser Gly Arg Lys Ser Gly Gly
        355                 360                 365

Val Cys Leu Asn Cys Arg His Asn Thr Ala Gly Arg His Cys His Tyr
    370                 375                 380

Cys Lys Glu Gly Phe Tyr Arg Asp Leu Ser Lys Pro Ile Ser His Arg
385                 390                 395                 400

Lys Ala Cys Lys Glu Cys Asp Cys His Pro Val Gly Ala Ala Gly Gln
                405                 410                 415

Thr Cys Asn Gln Thr Thr Gly Gln Cys Pro Cys Lys Asp Gly Val Thr
            420                 425                 430

Gly Ile Thr Cys Asn Arg Cys Ala Lys Gly Tyr Gln Gln Ser Arg Ser
            435                 440                 445

Pro Ile Ala Pro Cys Ile Lys Ile Pro Ala Ala Pro Pro Thr Ala
        450                 455                 460

Ala Ser Ser Thr Glu Glu Pro Ala Asp Cys Asp Ser Tyr Cys Lys Ala
465                 470                 475                 480

Ser Lys Gly Lys Leu Lys Ile Asn Met Lys Lys Tyr Cys Lys Lys Asp
                485                 490                 495

Tyr Ala Val Gln Ile His Ile Leu Lys Ala Glu Lys Asn Ala Asp Trp
                500                 505                 510

Trp Lys Phe Thr Val Asn Ile Ile Ser Val Tyr Lys Gln Gly Ser Asn
            515                 520                 525

Arg Leu Arg Arg Gly Asp Gln Thr Leu Trp Val His Ala Lys Asp Ile
    530                 535                 540

Ala Cys Lys Cys Pro Lys Val Lys Pro Met Lys Lys Tyr Leu Leu Leu
545                 550                 555                 560

Gly Ser Thr Glu Asp Ser Pro Asp Gln Ser Gly Ile Ile Ala Asp Lys
                565                 570                 575

Ser Ser Leu Val Ile Gln Trp Arg Asp Thr Trp Ala Arg Arg Leu Arg
            580                 585                 590

Lys Phe Gln Gln Arg Glu Lys Lys Gly Lys Cys Arg Lys Ala
            595                 600                 605
```

(2) INFORMATION FOR SEQ ID NO:23:

(i) SEQUENCE CHARACTERISTICS:
        (A) LENGTH: 581 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:23:

```
Leu Arg Leu Leu Leu Thr Thr Ser Val Leu Arg Leu Ala Arg Ala Ala
1               5                   10                  15

Asn Pro Glu Val Ala Gln Gln Thr Pro Pro Asp Pro Cys Tyr Asp Glu
            20                  25                  30

Ser Gly Ala Pro Arg Arg Cys Ile Pro Glu Phe Val Asn Ala Ala Phe
        35                  40                  45

Gly Lys Glu Val Gln Ala Ser Ser Thr Cys Gly Lys Pro Pro Thr Arg
    50                  55                  60
```

```
His Cys Asp Ala Ser Asp Pro Arg Arg Ala His Pro Pro Ala Tyr Leu
 65                  70                  75                  80

Thr Asp Leu Asn Thr Ala Ala Asn Met Thr Cys Trp Arg Ser Glu Thr
                 85                  90                  95

Leu His His Leu Pro His Asn Val Thr Leu Thr Leu Ser Leu Gly Lys
                100                 105                 110

Lys Phe Glu Val Val Tyr Val Ser Leu Gln Phe Cys Ser Pro Arg Pro
            115                 120                 125

Glu Ser Thr Ala Ile Phe Lys Ser Met Asp Tyr Gly Lys Thr Trp Val
130                 135                 140

Pro Tyr Gln Tyr Tyr Ser Ser Gln Cys Arg Lys Ile Tyr Gly Lys Pro
145                 150                 155                 160

Ser Lys Ala Thr Val Thr Lys Gln Asn Glu Gln Ala Leu Cys Thr
                165                 170                 175

Asp Gly Leu Thr Asp Leu Tyr Pro Leu Thr Gly Gly Leu Ile Ala Phe
            180                 185                 190

Ser Thr Leu Asp Gly Arg Pro Ser Ala Gln Asp Phe Asp Ser Ser Pro
            195                 200                 205

Val Leu Gln Asp Trp Val Thr Ala Thr Asp Ile Arg Val Val Phe Ser
210                 215                 220

Arg Pro His Leu Phe Arg Glu Leu Gly Gly Arg Glu Ala Gly Glu Glu
225                 230                 235                 240

Asp Gly Gly Ala Gly Ala Thr Pro Tyr Tyr Tyr Ser Val Gly Glu Leu
                245                 250                 255

Gln Val Gly Gly Arg Cys Lys Cys Asn Gly His Ala Ser Arg Cys Val
            260                 265                 270

Lys Asp Lys Glu Gln Lys Leu Val Cys Asp Cys Lys His Asn Thr Glu
            275                 280                 285

Gly Pro Glu Cys Asp Arg Cys Lys Pro Phe His Tyr Asp Arg Pro Trp
290                 295                 300

Gln Arg Ala Ser Ala Arg Glu Ala Asn Glu Cys Leu Ala Cys Asn Cys
305                 310                 315                 320

Asn Leu His Ala Arg Arg Cys Arg Phe Asn Met Glu Leu Tyr Lys Leu
            325                 330                 335

Ser Gly Arg Lys Ser Gly Gly Val Cys Leu Asn Cys Arg His Asn Thr
            340                 345                 350

Ala Gly Arg His Cys His Tyr Cys Lys Glu Gly Phe Tyr Arg Asp Leu
            355                 360                 365

Ser Lys Ser Ile Thr Asp Arg Lys Ala Cys Lys Ala Cys Asp Cys His
370                 375                 380

Pro Val Gly Ala Ala Gly Lys Thr Cys Asn Gln Thr Thr Gly Gln Cys
385                 390                 395                 400

Pro Cys Lys Asp Gly Val Thr Gly Leu Thr Cys Asn Arg Cys Ala Lys
            405                 410                 415

Gly Phe Gln Gln Ser Arg Ser Pro Val Ala Pro Cys Ile Lys Ile Pro
            420                 425                 430

Ala Ile Asn Pro Thr Ser Leu Val Thr Ser Thr Glu Ala Pro Ala Asp
            435                 440                 445

Cys Asp Ser Tyr Cys Lys Pro Ala Lys Gly Asn Tyr Lys Ile Asn Met
            450                 455                 460

Lys Lys Tyr Cys Lys Lys Asp Tyr Val Val Gln Val Asn Ile Leu Glu
465                 470                 475                 480
```

-continued

```
Met Glu Thr Val Ala Asn Trp Ala Lys Phe Thr Ile Asn Ile Leu Ser
            485                 490                 495

Val Tyr Lys Cys Arg Asp Glu Arg Val Lys Arg Gly Asp Asn Phe Leu
            500                 505                 510

Trp Ile His Leu Lys Asp Leu Ser Cys Lys Cys Pro Lys Ile Gln Ile
            515                 520                 525

Ser Lys Lys Tyr Leu Val Met Gly Ile Ser Glu Asn Ser Thr Asp Arg
            530                 535                 540

Pro Gly Leu Met Ala Asp Lys Asn Ser Leu Val Ile Gln Trp Arg Asp
545                 550                 555                 560

Ala Trp Thr Arg Arg Leu Arg Lys Leu Gln Arg Arg Glu Lys Lys Gly
            565                 570                 575

Lys Cys Val Lys Pro
            580
```

(2) INFORMATION FOR SEQ ID NO:24:

(i) SEQUENCE CHARACTERISTICS:
        (A) LENGTH: 5894 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..5053

(xi) SEQUENCE DESCRIPTION: SEQ ID NO:24:

```
G AAG GTC CTG GTG ACG GTC CTG GAA CTC TTC CTG CCA TTG CTG TTT        46
  Lys Val Leu Val Thr Val Leu Glu Leu Phe Leu Pro Leu Leu Phe
  1               5                  10                  15

TCT GGG ATC CTC ATC TGG CTC CGC TTG AAG ATT CAG TCG GAA AAT GTG     94
Ser Gly Ile Leu Ile Trp Leu Arg Leu Lys Ile Gln Ser Glu Asn Val
                20                  25                  30

CCC AAC GCC ACC ATC TAC CCG GGC CAG TCC ATC CAG GAG CTG CCT CTG    142
Pro Asn Ala Thr Ile Tyr Pro Gly Gln Ser Ile Gln Glu Leu Pro Leu
            35                  40                  45

TTC TTC ACC TTC CCT CCG CCA GGA GAC ACC TGG GAG CTT GCC TAC ATC    190
Phe Phe Thr Phe Pro Pro Pro Gly Asp Thr Trp Glu Leu Ala Tyr Ile
        50                  55                  60

CCT TCT CAC AGT GAC GCT GCC AAG GCC GTC ACT GAG ACA GTG CGC AGG    238
Pro Ser His Ser Asp Ala Ala Lys Ala Val Thr Glu Thr Val Arg Arg
    65                  70                  75

GCA CTT GTG ATC AAC ATG CGA GTG CGC GGC TTT CCC TCC GAG AAG GAC    286
Ala Leu Val Ile Asn Met Arg Val Arg Gly Phe Pro Ser Glu Lys Asp
80                  85                  90                  95

TTT GAG GAC TAC ATT AGG TAC GAC AAC TGC TCG TCC AGC GTG CTG GCC    334
Phe Glu Asp Tyr Ile Arg Tyr Asp Asn Cys Ser Ser Ser Val Leu Ala
                100                 105                 110

GCC GTG GTC TTC GAG CAC CCC TTC AAC CAC AGC AAG GAG CCC CTG CCG    382
Ala Val Val Phe Glu His Pro Phe Asn His Ser Lys Glu Pro Leu Pro
            115                 120                 125

CTG GCG GTG AAA TAT CAC CTA CGG TTC AGT TAC ACA CGG AGA AAT TAC    430
Leu Ala Val Lys Tyr His Leu Arg Phe Ser Tyr Thr Arg Arg Asn Tyr
        130                 135                 140

ATG TGG ACC CAA ACA GGC TCC TTT TTC CTG AAA GAG ACA GAA GGC TGG    478
Met Trp Thr Gln Thr Gly Ser Phe Phe Leu Lys Glu Thr Glu Gly Trp
    145                 150                 155

CAC ACT ACT TCC CTT TTC CCG CTT TTC CCA AAC CCA GGA CCA AGG GAA    526
```

-continued

```
His Thr Thr Ser Leu Phe Pro Leu Phe Pro Asn Pro Gly Pro Arg Glu
160                 165                 170                 175

CTA ACA TCC CCT GAT GGC GGA GAA CCT GGG TAC ATC CGG GAA GGC TTC         574
Leu Thr Ser Pro Asp Gly Gly Glu Pro Gly Tyr Ile Arg Glu Gly Phe
                180                 185                 190

CTG GCC GTG CAG CAT GCT GTG GAC CGG GCC ATC ATG GAG TAC CAT GCC         622
Leu Ala Val Gln His Ala Val Asp Arg Ala Ile Met Glu Tyr His Ala
            195                 200                 205

GAT GCC GCC ACA CGC CAG CTG TTC CAG AGA CTG ACG GTG ACC ATC AAG         670
Asp Ala Ala Thr Arg Gln Leu Phe Gln Arg Leu Thr Val Thr Ile Lys
        210                 215                 220

AGG TTC CCG TAC CCG CCG TTC ATC GCA GAC CCC TTC CTC GTG GCC ATC         718
Arg Phe Pro Tyr Pro Pro Phe Ile Ala Asp Pro Phe Leu Val Ala Ile
    225                 230                 235

CAG TAC CAG CTG CCC CTG CTG CTG CTC AGC TTC ACC TAC ACC GCG             766
Gln Tyr Gln Leu Pro Leu Leu Leu Leu Ser Phe Thr Tyr Thr Ala
240                 245                 250                 255

CTC ACC ATT GCC CGT GCT GTC GTG CAG GAG AAG GAA AGG AGG CTG AAG         814
Leu Thr Ile Ala Arg Ala Val Val Gln Glu Lys Glu Arg Arg Leu Lys
                260                 265                 270

GAG TAC ATG CGC ATG ATG GGG CTC AGC AGC TGG CTG CAC TGG AGT GCC         862
Glu Tyr Met Arg Met Met Gly Leu Ser Ser Trp Leu His Trp Ser Ala
            275                 280                 285

TGG TTC CTC TTG TTC TTC CTC TTC CTC ATC GCC GCC TCC TTC ATG             910
Trp Phe Leu Leu Phe Phe Leu Phe Leu Leu Ile Ala Ala Ser Phe Met
        290                 295                 300

ACC CTG CTC TTC TGT GTC AAG GTG AAG CCA AAT GTA GCC GTG CTG TCC         958
Thr Leu Leu Phe Cys Val Lys Val Lys Pro Asn Val Ala Val Leu Ser
    305                 310                 315

CGC AGC GAC CCC TCC CTG GTG CTC GCC TTC CTG CTG TGC TTC GCC ATC        1006
Arg Ser Asp Pro Ser Leu Val Leu Ala Phe Leu Leu Cys Phe Ala Ile
320                 325                 330                 335

TCT ACC ATC TCC TTC AGC TTC ATG GTC AGC ACC TTC TTC AGC AAA GCC        1054
Ser Thr Ile Ser Phe Ser Phe Met Val Ser Thr Phe Phe Ser Lys Ala
                340                 345                 350

AAC ATG GCA GCA GCC TTC GGA GGC TTC CTC TAC TTC TTC ACC TAC ATC        1102
Asn Met Ala Ala Ala Phe Gly Gly Phe Leu Tyr Phe Phe Thr Tyr Ile
            355                 360                 365

CCC TAC TTC TTC GTG GCC CCT CGG TAC AAC TGG ATG ACT CTG AGC CAG        1150
Pro Tyr Phe Phe Val Ala Pro Arg Tyr Asn Trp Met Thr Leu Ser Gln
        370                 375                 380

AAG CTC TGC TCC TGC CTC CTG TCT AAT GTC GCC ATG GCA ATG GGA GCC        1198
Lys Leu Cys Ser Cys Leu Leu Ser Asn Val Ala Met Ala Met Gly Ala
    385                 390                 395

CAG CTC ATT GGG AAA TTT GAG GCG AAA GGC ATG GGC ATC CAG TGG CGA        1246
Gln Leu Ile Gly Lys Phe Glu Ala Lys Gly Met Gly Ile Gln Trp Arg
400                 405                 410                 415

GAC CTC CTG AGT CCC GTC AAC GTG GAC GAC GAC TTC TGC TTC GGG CAG        1294
Asp Leu Leu Ser Pro Val Asn Val Asp Asp Asp Phe Cys Phe Gly Gln
                420                 425                 430

GTG CTG GGG ATG CTG CTG CTG GAC TCT GTG CTC TAT GGC CTG GTG ACC        1342
Val Leu Gly Met Leu Leu Leu Asp Ser Val Leu Tyr Gly Leu Val Thr
            435                 440                 445

TGG TAC ATG GAG GCC GTC TTC CCA GGG CAG TTC GGC GTG CCT CAG CCC        1390
Trp Tyr Met Glu Ala Val Phe Pro Gly Gln Phe Gly Val Pro Gln Pro
        450                 455                 460

TGG TAC TTC TTC ATC ATG CCC TCC TAT TGG TGT GGG AAG CCA AGG GCG        1438
Trp Tyr Phe Phe Ile Met Pro Ser Tyr Trp Cys Gly Lys Pro Arg Ala
    465                 470                 475
```

```
                                                         -continued

GTT GCA GGG AAG GAG GAA GAA GAC AGT GAC CCC GAG AAA GCA CTC AGA        1486
Val Ala Gly Lys Glu Glu Glu Asp Ser Asp Pro Glu Lys Ala Leu Arg
480                 485                 490                 495

AAC GAG TAC TTT GAA GCC GAG CCA GAG GAC CTG GTG GCG GGG ATC AAG        1534
Asn Glu Tyr Phe Glu Ala Glu Pro Glu Asp Leu Val Ala Gly Ile Lys
                500                 505                 510

ATC AAG CAC CTG TCC AAG GTG TTC AGG GTG GGA AAT AAG GAC AGG GCG        1582
Ile Lys His Leu Ser Lys Val Phe Arg Val Gly Asn Lys Asp Arg Ala
            515                 520                 525

GCC GTC AGA GAC CTG AAC CTC AAC CTG TAC GAG GGA CAG ATC ACC GTC        1630
Ala Val Arg Asp Leu Asn Leu Asn Leu Tyr Glu Gly Gln Ile Thr Val
        530                 535                 540

CTG CTG GGC CAC AAC GGT GCC GGG AAG ACC ACC ACC CTC TCC ATG CTC        1678
Leu Leu Gly His Asn Gly Ala Gly Lys Thr Thr Thr Leu Ser Met Leu
    545                 550                 555

ACA GGT CTC TTT CCC CCC ACC AGT GGA CGG GCA TAC ATC AGC GGG TAT        1726
Thr Gly Leu Phe Pro Pro Thr Ser Gly Arg Ala Tyr Ile Ser Gly Tyr
560                 565                 570                 575

GAA ATT TCC CAG GAC ATG GTT CAG ATC CGG AAG AGC CTG GGC CTG TGC        1774
Glu Ile Ser Gln Asp Met Val Gln Ile Arg Lys Ser Leu Gly Leu Cys
                580                 585                 590

CCG CAG CAC GAC ATC CTG TTT GAC AAC TTG ACA GTC GCA GAG CAC CTT        1822
Pro Gln His Asp Ile Leu Phe Asp Asn Leu Thr Val Ala Glu His Leu
            595                 600                 605

TAT TTC TAC GCC CAG CTG AAG GGC CTG TCA CGT CAG AAG TGC CCT GAA        1870
Tyr Phe Tyr Ala Gln Leu Lys Gly Leu Ser Arg Gln Lys Cys Pro Glu
        610                 615                 620

GAA GTC AAG CAG ATG CTG CAC ATC ATC GGC CTG GAG GAC AAG TGG AAC        1918
Glu Val Lys Gln Met Leu His Ile Ile Gly Leu Glu Asp Lys Trp Asn
    625                 630                 635

TCA CGG AGC CGC TTC CTG AGC GGG GGC ATG AGG CGC AAG CTC TCC ATC        1966
Ser Arg Ser Arg Phe Leu Ser Gly Gly Met Arg Arg Lys Leu Ser Ile
640                 645                 650                 655

GGC ATC GCC CTC ATC GCA GGC TCC AAG GTG CTG ATA CTG GAC GAG CCC        2014
Gly Ile Ala Leu Ile Ala Gly Ser Lys Val Leu Ile Leu Asp Glu Pro
                660                 665                 670

ACC TCG GGC ATG GAC GCC ATC TCC AGG AGG GCC ATC TGG GAT CTT CTT        2062
Thr Ser Gly Met Asp Ala Ile Ser Arg Arg Ala Ile Trp Asp Leu Leu
            675                 680                 685

CAG CGG CAG AAA AGT GAC CGC ACC ATC GTG CTG ACC ACC CAC TTC ATG        2110
Gln Arg Gln Lys Ser Asp Arg Thr Ile Val Leu Thr Thr His Phe Met
        690                 695                 700

GAC GAG GCT GAC CTG CTG GGA GAC CGC ATC GCC ATC ATG GCC AAG GGG        2158
Asp Glu Ala Asp Leu Leu Gly Asp Arg Ile Ala Ile Met Ala Lys Gly
    705                 710                 715

GAG CTG CAG TGC TGC GGG TCC TCG CTG TTC CTC AAG CAG AAA TAC GGT        2206
Glu Leu Gln Cys Cys Gly Ser Ser Leu Phe Leu Lys Gln Lys Tyr Gly
720                 725                 730                 735

GCC GGC TAT CAC ATG ACG CTG GTG AAG GAG CCG CAC TGC AAC CCG GAA        2254
Ala Gly Tyr His Met Thr Leu Val Lys Glu Pro His Cys Asn Pro Glu
                740                 745                 750

GAC ATC TCC CAG CTG GTC CAC CAC CAC GTG CCC AAC GCC ACG CTG GAG        2302
Asp Ile Ser Gln Leu Val His His His Val Pro Asn Ala Thr Leu Glu
            755                 760                 765

AGC AGC GCT GGG GCC GAG CTG TCT TTC ATC CTT CCC AGA GAG AGC ACG        2350
Ser Ser Ala Gly Ala Glu Leu Ser Phe Ile Leu Pro Arg Glu Ser Thr
        770                 775                 780

CAC AGG TTT GAA GGT CTC TTT GCT AAA CTG GAG AAG AAG CAG AAA GAG        2398
His Arg Phe Glu Gly Leu Phe Ala Lys Leu Glu Lys Lys Gln Lys Glu
    785                 790                 795
```

-continued

| | |
|---|---|
| CTG GGC ATT GCC AGC TTT GGG GCA TCC ATC ACC ACC ATG GAG GAA GTC<br>Leu Gly Ile Ala Ser Phe Gly Ala Ser Ile Thr Thr Met Glu Glu Val<br>800                        805                        810                        815 | 2446 |
| TTC CTT CGG GTC GGG AAG CTG GTG GAC AGC AGT ATG GAC ATC CAG GCC<br>Phe Leu Arg Val Gly Lys Leu Val Asp Ser Ser Met Asp Ile Gln Ala<br>                    820                        825                        830 | 2494 |
| ATC CAG CTC CCT GCC CTG CAG TAC CAG CAC GAG AGG CGC GCC AGC GAC<br>Ile Gln Leu Pro Ala Leu Gln Tyr Gln His Glu Arg Arg Ala Ser Asp<br>                835                        840                        845 | 2542 |
| TGG GCT GTG GAC AGC AAC CTC TGT GGG GCC ATG GAC CCC TCC GAC GGC<br>Trp Ala Val Asp Ser Asn Leu Cys Gly Ala Met Asp Pro Ser Asp Gly<br>        850                        855                        860 | 2590 |
| ATT GGA GCC CTC ATC GAG GAG GAG CGC ACC GCT GTC AAG CTC AAC ACT<br>Ile Gly Ala Leu Ile Glu Glu Glu Arg Thr Ala Val Lys Leu Asn Thr<br>865                        870                        875 | 2638 |
| GGG CTC GCC CTG CAC TGC CAG CAA TTC TGG GCC ATG TTC CTG AAG AAG<br>Gly Leu Ala Leu His Cys Gln Gln Phe Trp Ala Met Phe Leu Lys Lys<br>880                        885                        890                        895 | 2686 |
| GCC GCA TAC AGC TGG CGC GAG TGG AAA ATG GTG GCG GCA CAG GTC CTG<br>Ala Ala Tyr Ser Trp Arg Glu Trp Lys Met Val Ala Ala Gln Val Leu<br>                900                        905                        910 | 2734 |
| GTG CCT CTG ACC TGC GTC ACC CTG GCC CTC CTG GCC ATC AAC TAC TCC<br>Val Pro Leu Thr Cys Val Thr Leu Ala Leu Leu Ala Ile Asn Tyr Ser<br>                915                        920                        925 | 2782 |
| TCG GAG CTC TTC GAC GAC CCC ATG CTG AGG CTG ACC TTG GGC GAG TAC<br>Ser Glu Leu Phe Asp Asp Pro Met Leu Arg Leu Thr Leu Gly Glu Tyr<br>        930                        935                        940 | 2830 |
| GGC AGA ACC GTC GTG CCC TTC TCA GTT CCC GGG ACC TCC CAG CTG GGT<br>Gly Arg Thr Val Val Pro Phe Ser Val Pro Gly Thr Ser Gln Leu Gly<br>945                        950                        955 | 2878 |
| CAG CAG CTG TCA GAG CAT CTG AAA GAC GCA CTG CAG GCT GAG GGA CAG<br>Gln Gln Leu Ser Glu His Leu Lys Asp Ala Leu Gln Ala Glu Gly Gln<br>960                        965                        970                        975 | 2926 |
| GAG CCC CGC GAG GTG CTC GGT GAC CTG GAG GAG TTC TTG ATC TTC AGG<br>Glu Pro Arg Glu Val Leu Gly Asp Leu Glu Glu Phe Leu Ile Phe Arg<br>                980                        985                        990 | 2974 |
| GCT TCT GTG GAG GGG GGC GGC TTT AAT GAG CGG TGC CTT GTG GCA GCG<br>Ala Ser Val Glu Gly Gly Gly Phe Asn Glu Arg Cys Leu Val Ala Ala<br>        995                        1000                        1005 | 3022 |
| TCC TTC AGA GAT GTG GGA GAG CGC ACG GTC GTC AAC GCC TTG TTC AAC<br>Ser Phe Arg Asp Val Gly Glu Arg Thr Val Val Asn Ala Leu Phe Asn<br>              1010                        1015                        1020 | 3070 |
| AAC CAG GCG TAC CAC TCT CCA GCC ACT GCC CTG GCC GTC GTG GAC AAC<br>Asn Gln Ala Tyr His Ser Pro Ala Thr Ala Leu Ala Val Val Asp Asn<br>1025                      1030                        1035 | 3118 |
| CTT CTG TTC AAG CTG CTG TGC GGG CCT CAC GCC TCC ATT GTG GTC TCC<br>Leu Leu Phe Lys Leu Leu Cys Gly Pro His Ala Ser Ile Val Val Ser<br>1040                      1045                        1050                        1055 | 3166 |
| AAC TTC CCC CAG CCC CGG AGC GCC CTG CAG GCT GCC AAG GAC CAG TTT<br>Asn Phe Pro Gln Pro Arg Ser Ala Leu Gln Ala Ala Lys Asp Gln Phe<br>              1060                        1065                        1070 | 3214 |
| AAC GAG GGC CGG AAG GGA TTC GAC ATT GCC CTC AAC CTG CTC TTC GCC<br>Asn Glu Gly Arg Lys Gly Phe Asp Ile Ala Leu Asn Leu Leu Phe Ala<br>                1075                        1080                        1085 | 3262 |
| ATG GCA TTC TTG GCC AGC ACG TTC TCC ATC CTG GCG GTC AGC GAG AGG<br>Met Ala Phe Leu Ala Ser Thr Phe Ser Ile Leu Ala Val Ser Glu Arg<br>        1090                        1095                        1100 | 3310 |
| GCC GTG CAG GCC AAG CAT GTG CAG TTT GTG AGT GGA GTC CAC GTG GCC<br>Ala Val Gln Ala Lys His Val Gln Phe Val Ser Gly Val His Val Ala | 3358 |

```
                   1105                1110                1115
         AGT TTC TGG CTC TCT GCT CTG CTG TGG GAC CTC ATC TCC TTC CTC ATC       3406
         Ser Phe Trp Leu Ser Ala Leu Leu Trp Asp Leu Ile Ser Phe Leu Ile
         1120                1125                1130                1135

CCC AGT CTG CTG CTG CTG GTG GTG TTT AAG GCC TTC GAC GTG CGT GCC       3454
         Pro Ser Leu Leu Leu Leu Val Val Phe Lys Ala Phe Asp Val Arg Ala
                         1140                1145                1150

TTC ACG CGG GAC GGC CAC ATG GCT GAC ACC CTG CTG CTG CTC CTG CTC       3502
         Phe Thr Arg Asp Gly His Met Ala Asp Thr Leu Leu Leu Leu Leu Leu
                             1155                1160                1165

TAC GGC TGG GCC ATC ATC CCC CTC ATG TAC CTG ATG AAC TTC TTC TTC       3550
         Tyr Gly Trp Ala Ile Ile Pro Leu Met Tyr Leu Met Asn Phe Phe Phe
                     1170                1175                1180

TTG GGG GCG GCC ACT GCC TAC ACG AGG CTG ACC ATC TTC AAC ATC CTG       3598
         Leu Gly Ala Ala Thr Ala Tyr Thr Arg Leu Thr Ile Phe Asn Ile Leu
                 1185                1190                1195

TCA GGC ATC GCC ACC TTC CTG ATG GTC ACC ATC ATG CGC ATC CCA GCT       3646
         Ser Gly Ile Ala Thr Phe Leu Met Val Thr Ile Met Arg Ile Pro Ala
         1200                1205                1210                1215

GTA AAA CTG GAA GAA CTT TCC AAA ACC CTG GAT CAC GTG TTC CTG GTG       3694
         Val Lys Leu Glu Glu Leu Ser Lys Thr Leu Asp His Val Phe Leu Val
                         1220                1225                1230

CTG CCC AAC CAC TGT CTG GGG ATG GCA GTC AGC AGT TTC TAC GAG AAC       3742
         Leu Pro Asn His Cys Leu Gly Met Ala Val Ser Ser Phe Tyr Glu Asn
                     1235                1240                1245

TAC GAG ACG CGG AGG TAC TGC ACC TCC TCC GAG GTC GCC GCC CAC TAC       3790
         Tyr Glu Thr Arg Arg Tyr Cys Thr Ser Ser Glu Val Ala Ala His Tyr
                 1250                1255                1260

TGC AAG AAA TAT AAC ATC CAG TAC CAG GAG AAC TTC TAT GCC TGG AGC       3838
         Cys Lys Lys Tyr Asn Ile Gln Tyr Gln Glu Asn Phe Tyr Ala Trp Ser
         1265                1270                1275

GCC CCG GGG GTC GGC CGG TTT GTG GCC TCC ATG GCC GCC TCA GGG TGC       3886
         Ala Pro Gly Val Gly Arg Phe Val Ala Ser Met Ala Ala Ser Gly Cys
         1280                1285                1290                1295

GCC TAC CTC ATC CTG CTC TTC CTC ATC GAG ACC AAC CTG CTT CAG AGA       3934
         Ala Tyr Leu Ile Leu Leu Phe Leu Ile Glu Thr Asn Leu Leu Gln Arg
                         1300                1305                1310

CTC AGG GGC ATC CTC TGC GCC CTC CGG AGG AGG CGG ACA CTG ACA GAA       3982
         Leu Arg Gly Ile Leu Cys Ala Leu Arg Arg Arg Arg Thr Leu Thr Glu
                     1315                1320                1325

TTA TAC ACC CGG ATG CCT GTG CTT CCT GAG GAC CAA GAT GTA GCG GAC       4030
         Leu Tyr Thr Arg Met Pro Val Leu Pro Glu Asp Gln Asp Val Ala Asp
                 1330                1335                1340

GAG AGG ACC CGC ATC CTG GCC CCC AGC CCG GAC TCC CTG CTC CAC ACA       4078
         Glu Arg Thr Arg Ile Leu Ala Pro Ser Pro Asp Ser Leu Leu His Thr
         1345                1350                1355

CCT CTG ATT ATC AAG GAG CTC TCC AAG GTG TAC GAG CAG CGG GTG CCC       4126
         Pro Leu Ile Ile Lys Glu Leu Ser Lys Val Tyr Glu Gln Arg Val Pro
         1360                1365                1370                1375

CTC CTG GCC GTG GAC AGG CTC TCC CTC GCG GTG CAG AAA GGG GAG TGC       4174
         Leu Leu Ala Val Asp Arg Leu Ser Leu Ala Val Gln Lys Gly Glu Cys
                         1380                1385                1390

TTC GGC CTG CTG GGC TTC AAT GGA GCC GGG AAG ACC ACG ACT TTC AAA       4222
         Phe Gly Leu Leu Gly Phe Asn Gly Ala Gly Lys Thr Thr Thr Phe Lys
                     1395                1400                1405

ATG CTG ACC GGG GAG GAG AGC CTC ACT TCT GGG GAT GCC TTT GTC GGG       4270
         Met Leu Thr Gly Glu Glu Ser Leu Thr Ser Gly Asp Ala Phe Val Gly
                 1410                1415                1420

GGT CAC AGA ATC AGC TCT GAT GTC GGA AAG GTG CGG CAG CGG ATC GGC       4318
```

-continued

```
Gly His Arg Ile Ser Ser Asp Val Gly Lys Val Arg Gln Arg Ile Gly
    1425                1430                1435

TAC TGC CCG CAG TTT GAT GCC TTG CTG GAC CAC ATG ACA GGC CGG GAG       4366
Tyr Cys Pro Gln Phe Asp Ala Leu Leu Asp His Met Thr Gly Arg Glu
1440                1445                1450                1455

ATG CTG GTC ATG TAC GCT CGG CTC CGG GGC ATC CCT GAG CGC CAC ATC       4414
Met Leu Val Met Tyr Ala Arg Leu Arg Gly Ile Pro Glu Arg His Ile
                1460                1465                1470

GGG GCC TGC GTG GAG AAC ACT CTG CGG GGC CTG CTG CTG GAG CCA CAT       4462
Gly Ala Cys Val Glu Asn Thr Leu Arg Gly Leu Leu Leu Glu Pro His
            1475                1480                1485

GCC AAC AAG CTG GTC AGG ACG TAC AGT GGT GGT AAC AAG CGG AAG CTG       4510
Ala Asn Lys Leu Val Arg Thr Tyr Ser Gly Gly Asn Lys Arg Lys Leu
        1490                1495                1500

AGC ACC GGC ATC GCC CTG ATC GGA GAG CCT GCT GTC ATC TTC CTG GAC       4558
Ser Thr Gly Ile Ala Leu Ile Gly Glu Pro Ala Val Ile Phe Leu Asp
    1505                1510                1515

GAG CCG TCC ACT GGC ATG GAC CCC GTG GCC CGG CGC CTG CTT TGG GAC       4606
Glu Pro Ser Thr Gly Met Asp Pro Val Ala Arg Arg Leu Leu Trp Asp
1520                1525                1530                1535

ACC GTG GCA CGA GCC CGA GAG TCT GGC AAG GCC ATC ATC ATC ACC TCC       4654
Thr Val Ala Arg Ala Arg Glu Ser Gly Lys Ala Ile Ile Ile Thr Ser
                1540                1545                1550

CAC AGC ATG GAG GAG TGT GAG GCC CTG TGC ACC CGG CTG GCC ATC ATG       4702
His Ser Met Glu Glu Cys Glu Ala Leu Cys Thr Arg Leu Ala Ile Met
            1555                1560                1565

GTG CAG GGG CAG TTC AAG TGC CTG GGC AGC CCC CAG CAC CTC AAG AGC       4750
Val Gln Gly Gln Phe Lys Cys Leu Gly Ser Pro Gln His Leu Lys Ser
        1570                1575                1580

AAG TTC GGC AGC GGC TAC TCC CTG CGG GCC AAG GTG CAG AGT GAA GGG       4798
Lys Phe Gly Ser Gly Tyr Ser Leu Arg Ala Lys Val Gln Ser Glu Gly
    1585                1590                1595

CAA CAG GAG GCG CTG GAG GAG TTC AAG GCC TTC GTG GAC CTG ACC TTT       4846
Gln Gln Glu Ala Leu Glu Glu Phe Lys Ala Phe Val Asp Leu Thr Phe
1600                1605                1610                1615

CCA GGC AGC GTC CTG GAA GAT GAG CAC CAA GGC ATG GTC CAT TAC CAC       4894
Pro Gly Ser Val Leu Glu Asp Glu His Gln Gly Met Val His Tyr His
                1620                1625                1630

CTG CCG GGC CGT GAC CTC AGC TGG GCG AAG GTT TTC GGT ATT CTG GAG       4942
Leu Pro Gly Arg Asp Leu Ser Trp Ala Lys Val Phe Gly Ile Leu Glu
            1635                1640                1645

AAA GCC AAG GAA AAG TAC GGC GTG GAC GAC TAC TCC GTG AGC CAG ATC       4990
Lys Ala Lys Glu Lys Tyr Gly Val Asp Asp Tyr Ser Val Ser Gln Ile
        1650                1655                1660

TCG CTG GAA CAG GTC TTC CTG AGC TTC GCC CAC CTG CAG CCG CCC ACC       5038
Ser Leu Glu Gln Val Phe Leu Ser Phe Ala His Leu Gln Pro Pro Thr
    1665                1670                1675

GCA GAG GAG GGG CGA TGAGGGGTGG CGGCTGTCTC GCCATCAGGC AGGGACAGGA       5093
Ala Glu Glu Gly Arg
1680

CGGGCAAGCA GGGCCCATCT TACATCCTCT CTCTCCAAGT TTATCTCATC CTTTATTTTT     5153

AATCACTTTT TTCTATGATG GATATGAAAA ATTCAAGGCA GTATGCACAG AATGGACGAG     5213

TGCAGCCCAG CCCTCATGCC CAGGATCAGC ATGCGCATCT CCATGTCTGC ATACTCTGGA     5273

GTTCACTTTC CCAGAGCTGG GGCAGGCCGG GCAGTCTGCG GGCAAGCTCC GGGGTCTCTG     5333

GGTGGAGAGC TGACCCAGGA AGGGCTGCAG CTGAGCTGGG GGTTGAATTT CTCCAGGCAC     5393

TCCCTGGAGA GAGGACCCAG TGACTTGTCC AAGTTTACAC ACGACACTAA TCTCCCCTGG     5453
```

```
GGAGGAAGCG GGAAGCCAGC CAGGTTGAAC TGTAGCGAGG CCCCCAGGCC GCCAGGAATG      5513

GACCATGCAG ATCACTGTCA GTGGAGGGAA GCTGCTGACT GTGATTAGGT GCTGGGGTCT      5573

TAGCGTCCAG CGCAGCCCGG GGGCATCCTG GAGGCTCTGC TCCTTAGGGC ATGGTAGTCA      5633

CCGCGAAGCC GGGCACCGTC CCACAGCATC TCCTAGAAGC AGCCGGCACA GGAGGGAAGG      5693

TGGCCAGGCT CGAAGCAGTC TCTGTTTCCA GCACTGCACC CTCAGGAAGT CGCCCGCCCC      5753

AGGACACGCA GGGACCACCC TAAGGGCTGG GTGGCTGTCT CAAGGACACA TTGAATACGT      5813

TGTGACCATC CAGAAAATAA ATGCTGAGGG GACACAAAAA AAAAAAAAAA AAAAAAAAAA      5873

AAAAAAAAAA AAAAAAAAAA A                                               5894
```

(2) INFORMATION FOR SEQ ID NO:25:

(i) SEQUENCE CHARACTERISTICS:
        (A) LENGTH: 1684 amino acids
        (B) TYPE: amino acid
        (D) TOPOLOGY: linear (ii) MOLECULE TYPE: protein (xi) SEQUENCE DESCRIPTION: SEQ ID NO:25:

```
Lys Val Leu Val Thr Val Leu Glu Leu Phe Leu Pro Leu Leu Phe Ser
  1               5                  10                  15

Gly Ile Leu Ile Trp Leu Arg Leu Lys Ile Gln Ser Glu Asn Val Pro
             20                  25                  30

Asn Ala Thr Ile Tyr Pro Gly Gln Ser Ile Gln Glu Leu Pro Leu Phe
         35                  40                  45

Phe Thr Phe Pro Pro Pro Gly Asp Thr Trp Glu Leu Ala Tyr Ile Pro
     50                  55                  60

Ser His Ser Asp Ala Ala Lys Ala Val Thr Glu Thr Val Arg Arg Ala
 65                  70                  75                  80

Leu Val Ile Asn Met Arg Val Arg Gly Phe Pro Ser Glu Lys Asp Phe
                 85                  90                  95

Glu Asp Tyr Ile Arg Tyr Asp Asn Cys Ser Ser Ser Val Leu Ala Ala
            100                 105                 110

Val Val Phe Glu His Pro Phe Asn His Ser Lys Glu Pro Leu Pro Leu
        115                 120                 125

Ala Val Lys Tyr His Leu Arg Phe Ser Tyr Thr Arg Arg Asn Tyr Met
    130                 135                 140

Trp Thr Gln Thr Gly Ser Phe Leu Lys Glu Thr Glu Gly Trp His
145                 150                 155                 160

Thr Thr Ser Leu Phe Pro Leu Phe Pro Asn Pro Gly Pro Arg Glu Leu
                165                 170                 175

Thr Ser Pro Asp Gly Gly Glu Pro Gly Tyr Ile Arg Glu Gly Phe Leu
            180                 185                 190

Ala Val Gln His Ala Val Asp Arg Ala Ile Met Glu Tyr His Ala Asp
        195                 200                 205

Ala Ala Thr Arg Gln Leu Phe Gln Arg Leu Thr Val Thr Ile Lys Arg
    210                 215                 220

Phe Pro Tyr Pro Pro Phe Ile Ala Asp Pro Phe Leu Val Ala Ile Gln
225                 230                 235                 240

Tyr Gln Leu Pro Leu Leu Leu Leu Ser Phe Thr Tyr Thr Ala Leu
                245                 250                 255

Thr Ile Ala Arg Ala Val Val Gln Glu Lys Glu Arg Arg Leu Lys Glu
            260                 265                 270
```

-continued

```
Tyr Met Arg Met Met Gly Leu Ser Ser Trp Leu His Trp Ser Ala Trp
            275                 280                 285

Phe Leu Leu Phe Phe Leu Phe Leu Leu Ile Ala Ala Ser Phe Met Thr
            290                 295                 300

Leu Leu Phe Cys Val Lys Val Lys Pro Asn Val Ala Val Leu Ser Arg
305                 310                 315                 320

Ser Asp Pro Ser Leu Val Leu Ala Phe Leu Leu Cys Phe Ala Ile Ser
                325                 330                 335

Thr Ile Ser Phe Ser Phe Met Val Ser Thr Phe Phe Ser Lys Ala Asn
            340                 345                 350

Met Ala Ala Ala Phe Gly Gly Phe Leu Tyr Phe Phe Thr Tyr Ile Pro
            355                 360                 365

Tyr Phe Phe Val Ala Pro Arg Tyr Asn Trp Met Thr Leu Ser Gln Lys
            370                 375                 380

Leu Cys Ser Cys Leu Leu Ser Asn Val Ala Met Ala Met Gly Ala Gln
385                 390                 395                 400

Leu Ile Gly Lys Phe Glu Ala Lys Gly Met Gly Ile Gln Trp Arg Asp
                405                 410                 415

Leu Leu Ser Pro Val Asn Val Asp Asp Phe Cys Phe Gly Gln Val
                420                 425                 430

Leu Gly Met Leu Leu Asp Ser Val Leu Tyr Gly Leu Val Thr Trp
            435                 440                 445

Tyr Met Glu Ala Val Phe Pro Gly Gln Phe Gly Val Pro Gln Pro Trp
450                 455                 460

Tyr Phe Phe Ile Met Pro Ser Tyr Trp Cys Gly Lys Pro Arg Ala Val
465                 470                 475                 480

Ala Gly Lys Glu Glu Glu Asp Ser Asp Pro Glu Lys Ala Leu Arg Asn
                485                 490                 495

Glu Tyr Phe Glu Ala Glu Pro Asp Leu Val Ala Gly Ile Lys Ile
                500                 505                 510

Lys His Leu Ser Lys Val Phe Arg Val Gly Asn Lys Asp Arg Ala Ala
            515                 520                 525

Val Arg Asp Leu Asn Leu Asn Leu Tyr Glu Gly Gln Ile Thr Val Leu
530                 535                 540

Leu Gly His Asn Gly Ala Gly Lys Thr Thr Thr Leu Ser Met Leu Thr
545                 550                 555                 560

Gly Leu Phe Pro Pro Thr Ser Gly Arg Ala Tyr Ile Ser Gly Tyr Glu
                565                 570                 575

Ile Ser Gln Asp Met Val Gln Ile Arg Lys Ser Leu Gly Leu Cys Pro
                580                 585                 590

Gln His Asp Ile Leu Phe Asp Asn Leu Thr Val Ala Glu His Leu Tyr
            595                 600                 605

Phe Tyr Ala Gln Leu Lys Gly Leu Ser Arg Gln Lys Cys Pro Glu Glu
            610                 615                 620

Val Lys Gln Met Leu His Ile Ile Gly Leu Glu Asp Lys Trp Asn Ser
625                 630                 635                 640

Arg Ser Arg Phe Leu Ser Gly Gly Met Arg Arg Lys Leu Ser Ile Gly
                645                 650                 655

Ile Ala Leu Ile Ala Gly Ser Lys Val Leu Ile Leu Asp Glu Pro Thr
            660                 665                 670

Ser Gly Met Asp Ala Ile Ser Arg Arg Ala Ile Trp Asp Leu Leu Gln
            675                 680                 685

Arg Gln Lys Ser Asp Arg Thr Ile Val Leu Thr Thr His Phe Met Asp
```

-continued

```
        690                 695                 700
Glu Ala Asp Leu Leu Gly Asp Arg Ile Ala Ile Met Ala Lys Gly Glu
705                 710                 715                 720

Leu Gln Cys Cys Gly Ser Ser Leu Phe Leu Lys Gln Lys Tyr Gly Ala
            725                 730                 735

Gly Tyr His Met Thr Leu Val Lys Glu Pro His Cys Asn Pro Glu Asp
            740                 745                 750

Ile Ser Gln Leu Val His His Val Pro Asn Ala Thr Leu Glu Ser
            755                 760                 765

Ser Ala Gly Ala Glu Leu Ser Phe Ile Leu Pro Arg Glu Ser Thr His
770                 775                 780

Arg Phe Glu Gly Leu Phe Ala Lys Leu Glu Lys Gln Lys Glu Leu
785                 790                 795                 800

Gly Ile Ala Ser Phe Gly Ala Ser Ile Thr Thr Met Glu Glu Val Phe
            805                 810                 815

Leu Arg Val Gly Lys Leu Val Asp Ser Ser Met Asp Ile Gln Ala Ile
            820                 825                 830

Gln Leu Pro Ala Leu Gln Tyr Gln His Glu Arg Arg Ala Ser Asp Trp
            835                 840                 845

Ala Val Asp Ser Asn Leu Cys Gly Ala Met Asp Pro Ser Asp Gly Ile
850                 855                 860

Gly Ala Leu Ile Glu Glu Arg Thr Ala Val Lys Leu Asn Thr Gly
865                 870                 875                 880

Leu Ala Leu His Cys Gln Gln Phe Trp Ala Met Phe Leu Lys Lys Ala
            885                 890                 895

Ala Tyr Ser Trp Arg Glu Trp Lys Met Val Ala Ala Gln Val Leu Val
            900                 905                 910

Pro Leu Thr Cys Val Thr Leu Ala Leu Leu Ala Ile Asn Tyr Ser Ser
            915                 920                 925

Glu Leu Phe Asp Asp Pro Met Leu Arg Leu Thr Leu Gly Glu Tyr Gly
            930                 935                 940

Arg Thr Val Val Pro Phe Ser Val Pro Gly Thr Ser Gln Leu Gly Gln
945                 950                 955                 960

Gln Leu Ser Glu His Leu Lys Asp Ala Leu Gln Ala Glu Gly Gln Glu
            965                 970                 975

Pro Arg Glu Val Leu Gly Asp Leu Glu Glu Phe Leu Ile Phe Arg Ala
            980                 985                 990

Ser Val Glu Gly Gly Phe Asn Glu Arg Cys Leu Val Ala Ala Ser
            995                 1000                1005

Phe Arg Asp Val Gly Glu Arg Thr Val Val Asn Ala Leu Phe Asn Asn
            1010                1015                1020

Gln Ala Tyr His Ser Pro Ala Thr Ala Leu Ala Val Val Asp Asn Leu
1025                1030                1035                1040

Leu Phe Lys Leu Leu Cys Gly Pro His Ala Ser Ile Val Val Ser Asn
            1045                1050                1055

Phe Pro Gln Pro Arg Ser Ala Leu Gln Ala Ala Lys Asp Gln Phe Asn
            1060                1065                1070

Glu Gly Arg Lys Gly Phe Asp Ile Ala Leu Asn Leu Leu Phe Ala Met
            1075                1080                1085

Ala Phe Leu Ala Ser Thr Phe Ser Ile Leu Ala Val Ser Glu Arg Ala
            1090                1095                1100

Val Gln Ala Lys His Val Gln Phe Val Ser Gly Val His Val Ala Ser
1105                1110                1115                1120
```

```
Phe Trp Leu Ser Ala Leu Leu Trp Asp Leu Ile Ser Phe Leu Ile Pro
            1125                1130                1135

Ser Leu Leu Leu Leu Val Val Phe Lys Ala Phe Asp Val Arg Ala Phe
            1140                1145                1150

Thr Arg Asp Gly His Met Ala Asp Thr Leu Leu Leu Leu Leu Leu Tyr
            1155                1160                1165

Gly Trp Ala Ile Ile Pro Leu Met Tyr Leu Met Asn Phe Phe Phe Leu
            1170                1175                1180

Gly Ala Ala Thr Ala Tyr Thr Arg Leu Thr Ile Phe Asn Ile Leu Ser
1185                1190                1195                1200

Gly Ile Ala Thr Phe Leu Met Val Thr Ile Met Arg Ile Pro Ala Val
            1205                1210                1215

Lys Leu Glu Glu Leu Ser Lys Thr Leu Asp His Val Phe Leu Val Leu
            1220                1225                1230

Pro Asn His Cys Leu Gly Met Ala Val Ser Ser Phe Tyr Glu Asn Tyr
            1235                1240                1245

Glu Thr Arg Arg Tyr Cys Thr Ser Ser Glu Val Ala Ala His Tyr Cys
            1250                1255                1260

Lys Lys Tyr Asn Ile Gln Tyr Gln Glu Asn Phe Tyr Ala Trp Ser Ala
1265                1270                1275                1280

Pro Gly Val Gly Arg Phe Val Ala Ser Met Ala Ala Ser Gly Cys Ala
            1285                1290                1295

Tyr Leu Ile Leu Leu Phe Leu Ile Glu Thr Asn Leu Leu Gln Arg Leu
            1300                1305                1310

Arg Gly Ile Leu Cys Ala Leu Arg Arg Arg Thr Leu Thr Glu Leu
            1315                1320                1325

Tyr Thr Arg Met Pro Val Leu Pro Glu Asp Gln Asp Val Ala Asp Glu
            1330                1335                1340

Arg Thr Arg Ile Leu Ala Pro Ser Pro Asp Ser Leu Leu His Thr Pro
1345                1350                1355                1360

Leu Ile Ile Lys Glu Leu Ser Lys Val Tyr Glu Gln Arg Val Pro Leu
            1365                1370                1375

Leu Ala Val Asp Arg Leu Ser Leu Ala Val Gln Lys Gly Glu Cys Phe
            1380                1385                1390

Gly Leu Leu Gly Phe Asn Gly Ala Gly Lys Thr Thr Thr Phe Lys Met
            1395                1400                1405

Leu Thr Gly Glu Glu Ser Leu Thr Ser Gly Asp Ala Phe Val Gly Gly
            1410                1415                1420

His Arg Ile Ser Ser Asp Val Gly Lys Val Arg Gln Arg Ile Gly Tyr
1425                1430                1435                1440

Cys Pro Gln Phe Asp Ala Leu Leu Asp His Met Thr Gly Arg Glu Met
            1445                1450                1455

Leu Val Met Tyr Ala Arg Leu Arg Gly Ile Pro Glu Arg His Ile Gly
            1460                1465                1470

Ala Cys Val Glu Asn Thr Leu Arg Gly Leu Leu Leu Glu Pro His Ala
            1475                1480                1485

Asn Lys Leu Val Arg Thr Tyr Ser Gly Gly Asn Lys Arg Lys Leu Ser
            1490                1495                1500

Thr Gly Ile Ala Leu Ile Gly Glu Pro Ala Val Ile Phe Leu Asp Glu
1505                1510                1515                1520

Pro Ser Thr Gly Met Asp Pro Val Ala Arg Arg Leu Leu Trp Asp Thr
            1525                1530                1535
```

-continued

```
Val Ala Arg Ala Arg Glu Ser Gly Lys Ala Ile Ile Ile Thr Ser His
            1540                1545                1550

Ser Met Glu Glu Cys Glu Ala Leu Cys Thr Arg Leu Ala Ile Met Val
            1555                1560                1565

Gln Gly Gln Phe Lys Cys Leu Gly Ser Pro Gln His Leu Lys Ser Lys
            1570                1575                1580

Phe Gly Ser Gly Tyr Ser Leu Arg Ala Lys Val Gln Ser Glu Gly Gln
1585                1590                1595                1600

Gln Glu Ala Leu Glu Glu Phe Lys Ala Phe Val Asp Leu Thr Phe Pro
                1605                1610                1615

Gly Ser Val Leu Glu Asp Glu His Gln Gly Met Val His Tyr His Leu
            1620                1625                1630

Pro Gly Arg Asp Leu Ser Trp Ala Lys Val Phe Gly Ile Leu Glu Lys
            1635                1640                1645

Ala Lys Glu Lys Tyr Gly Val Asp Asp Tyr Ser Val Ser Gln Ile Ser
            1650                1655                1660

Leu Glu Gln Val Phe Leu Ser Phe Ala His Leu Gln Pro Pro Thr Ala
1665                1670                1675                1680

Glu Glu Gly Arg
```

(2) INFORMATION FOR SEQ ID NO:26:

(i) SEQUENCE CHARACTERISTICS:
        (A) LENGTH: 1375 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:26:

```
Cys Met Glu Glu Glu Pro Thr His Leu Arg Leu Gly Val Ser Ile Gln
1               5                  10                  15

Asn Leu Val Lys Val Tyr Arg Asp Gly Met Lys Val Ala Val Asp Gly
            20                  25                  30

Leu Ala Leu Asn Phe Tyr Glu Gly Gln Ile Thr Ser Phe Leu Gly His
            35                  40                  45

Asn Gly Ala Gly Lys Thr Thr Thr Met Ser Ile Leu Thr Gly Leu Phe
50                  55                  60

Pro Pro Thr Ser Gly Thr Ala Tyr Ile Leu Gly Lys Asp Ile Arg Ser
65                  70                  75                  80

Glu Met Ser Ser Ile Arg Gln Asn Leu Gly Val Cys Pro Gln His Asn
                85                  90                  95

Val Leu Phe Asp Met Leu Thr Val Glu Glu His Ile Trp Phe Tyr Ala
            100                 105                 110

Arg Leu Lys Gly Leu Ser Glu Lys His Val Lys Ala Glu Met Glu Gln
            115                 120                 125

Met Ala Leu Asp Val Gly Leu Pro Pro Ser Lys Leu Lys Ser Lys Thr
            130                 135                 140

Ser Gln Leu Ser Gly Gly Met Gln Arg Lys Leu Ser Val Ala Leu Ala
145                 150                 155                 160

Phe Val Gly Gly Ser Lys Val Val Ile Leu Asp Glu Pro Thr Ala Gly
                165                 170                 175

Val Asp Pro Tyr Ser Arg Arg Gly Ile Trp Glu Leu Leu Leu Lys Tyr
            180                 185                 190

Arg Gln Gly Arg Thr Ile Ile Leu Ser Thr His His Met Asp Glu Ala
```

-continued

```
            195                 200                 205
Asp Ile Leu Gly Asp Arg Ile Ala Ile Ile Ser His Gly Lys Leu Cys
    210                 215                 220
Cys Val Gly Ser Ser Leu Phe Leu Lys Asn Gln Leu Gly Thr Gly Tyr
225                 230                 235                 240
Tyr Leu Thr Leu Val Lys Lys Asp Val Glu Ser Ser Leu Ser Ser Cys
            245                 250                 255
Arg Asn Ser Ser Ser Thr Val Ser Cys Leu Lys Lys Glu Asp Ser Val
            260                 265                 270
Ser Gln Ser Ser Ser Asp Ala Gly Leu Gly Ser Asp His Glu Ser Asp
            275                 280                 285
Thr Leu Thr Ile Asp Val Ser Ala Ile Ser Asn Leu Ile Arg Lys His
            290                 295                 300
Val Ser Glu Ala Arg Leu Val Glu Asp Ile Gly His Glu Leu Thr Tyr
305                 310                 315                 320
Val Leu Pro Tyr Glu Ala Ala Lys Glu Gly Ala Phe Val Glu Leu Phe
            325                 330                 335
His Glu Ile Asp Asp Arg Leu Ser Asp Leu Gly Ile Ser Ser Tyr Gly
            340                 345                 350
Ile Ser Glu Thr Thr Leu Glu Glu Ile Phe Leu Lys Val Ala Glu Glu
            355                 360                 365
Ser Gly Val Asp Ala Glu Thr Ser Asp Gly Thr Leu Pro Ala Arg Arg
370                 375                 380
Asn Arg Arg Ala Phe Gly Asp Lys Gln Ser Cys Leu His Pro Phe Thr
385                 390                 395                 400
Glu Asp Asp Ala Val Asp Pro Asn Asp Ser Asp Ile Asp Pro Glu Ser
            405                 410                 415
Arg Glu Thr Asp Leu Leu Ser Gly Met Asp Gly Lys Gly Ser Tyr Gln
            420                 425                 430
Leu Lys Gly Trp Lys Leu Thr Gln Gln Gln Phe Val Ala Leu Leu Trp
            435                 440                 445
Lys Arg Leu Leu Ile Ala Arg Arg Ser Arg Lys Gly Phe Phe Ala Gln
            450                 455                 460
Ile Val Leu Pro Ala Val Phe Val Cys Ile Ala Leu Val Phe Ser Leu
465                 470                 475                 480
Ile Val Pro Pro Phe Gly Lys Tyr Pro Ser Leu Glu Leu Gln Pro Trp
            485                 490                 495
Met Tyr Asn Glu Gln Tyr Thr Phe Val Ser Asn Asp Ala Pro Glu Asp
            500                 505                 510
Met Gly Thr Gln Glu Leu Leu Asn Ala Leu Thr Lys Asp Pro Gly Phe
            515                 520                 525
Gly Thr Arg Cys Met Glu Gly Asn Pro Ile Pro Asp Thr Pro Cys Leu
            530                 535                 540
Ala Gly Glu Glu Asp Trp Thr Ile Ser Pro Val Pro Gln Ser Ile Val
545                 550                 555                 560
Asp Leu Phe Gln Asn Gly Asn Trp Thr Met Lys Asn Pro Ser Pro Ala
            565                 570                 575
Cys Gln Cys Ser Ser Asp Lys Ile Lys Lys Met Leu Pro Val Cys Pro
            580                 585                 590
Pro Gly Ala Gly Gly Leu Pro Pro Gln Arg Lys Gln Lys Thr Ala
            595                 600                 605
Asp Ile Leu Gln Asn Leu Thr Gly Arg Asn Ile Ser Asp Tyr Leu Val
            610                 615                 620
```

-continued

```
Lys Thr Tyr Val Gln Ile Ile Ala Lys Ser Leu Lys Asn Lys Ile Trp
625                 630                 635                 640

Val Asn Glu Phe Arg Tyr Gly Gly Phe Ser Leu Gly Val Ser Asn Ser
            645                 650                 655

Gln Ala Leu Pro Pro Ser His Glu Val Asn Asp Ala Ile Lys Gln Met
            660                 665                 670

Lys Lys Leu Leu Lys Leu Thr Lys Asp Thr Ser Ala Asp Arg Phe Leu
            675                 680                 685

Ser Ser Leu Gly Arg Phe Met Ala Gly Leu Asp Thr Lys Asn Asn Val
690                 695                 700

Lys Val Trp Phe Asn Asn Lys Gly Trp His Ala Ile Ser Ser Phe Leu
705                 710                 715                 720

Asn Val Ile Asn Asn Ala Ile Leu Arg Ala Asn Leu Gln Lys Gly Glu
                725                 730                 735

Asn Pro Ser Gln Tyr Gly Ile Thr Ala Phe Asn His Pro Leu Asn Leu
                740                 745                 750

Thr Lys Gln Gln Leu Ser Glu Val Ala Leu Met Thr Thr Ser Val Asp
                755                 760                 765

Val Leu Val Ser Ile Cys Val Ile Phe Ala Met Ser Phe Val Pro Ala
770                 775                 780

Ser Phe Val Val Phe Leu Ile Gln Glu Arg Val Ser Lys Ala Lys His
785                 790                 795                 800

Leu Gln Phe Ile Ser Gly Val Lys Pro Val Ile Tyr Trp Leu Ser Asn
                805                 810                 815

Phe Val Trp Asp Met Cys Asn Tyr Val Val Pro Ala Thr Leu Val Ile
                820                 825                 830

Ile Ile Phe Ile Cys Phe Gln Gln Lys Ser Tyr Val Ser Ser Thr Asn
                835                 840                 845

Leu Pro Val Leu Ala Leu Leu Leu Leu Tyr Gly Trp Ser Ile Thr
850                 855                 860

Pro Leu Met Tyr Pro Ala Ser Phe Val Phe Lys Ile Pro Ser Thr Ala
865                 870                 875                 880

Tyr Val Val Leu Thr Ser Val Asn Leu Phe Ile Gly Ile Asn Gly Ser
                885                 890                 895

Val Ala Thr Phe Val Leu Glu Leu Phe Thr Asn Asn Lys Leu Asn Asp
                900                 905                 910

Ile Asn Asp Ile Leu Lys Ser Val Phe Leu Ile Phe Pro His Phe Cys
                915                 920                 925

Leu Gly Arg Gly Leu Ile Asp Met Val Lys Asn Gln Ala Met Ala Asp
930                 935                 940

Ala Leu Glu Arg Phe Gly Glu Asn Arg Phe Val Ser Pro Leu Ser Trp
945                 950                 955                 960

Asp Leu Val Gly Arg Asn Leu Phe Ala Met Ala Val Glu Gly Val Val
                965                 970                 975

Phe Phe Leu Ile Thr Val Leu Ile Gln Tyr Arg Phe Phe Ile Arg Pro
                980                 985                 990

Arg Pro Val Lys Ala Lys Leu Pro Pro Leu Asn Asp Glu Asp Glu Asp
            995                 1000                1005

Val Arg Arg Glu Arg Gln Arg Ile Leu Asp Gly Gly Gln Asn Asp
        1010                1015                1020

Ile Leu Glu Ile Lys Glu Leu Thr Lys Ile Tyr Arg Arg Lys Arg Lys
1025                1030                1035                1040
```

-continued

```
Pro Ala Val Asp Arg Ile Cys Ile Gly Ile Pro Pro Gly Glu Cys Phe
                1045                1050                1055

Gly Leu Leu Gly Val Asn Gly Ala Gly Lys Ser Thr Thr Phe Lys Met
                1060                1065                1070

Leu Thr Gly Asp Thr Pro Val Thr Arg Gly Asp Ala Phe Leu Asn Lys
                1075                1080                1085

Asn Ser Ile Leu Ser Asn Ile His Glu Val His Gln Asn Met Gly Tyr
                1090                1095                1100

Cys Pro Gln Phe Asp Ala Ile Thr Glu Leu Leu Thr Gly Arg Glu His
1105                1110                1115                1120

Val Glu Phe Phe Ala Leu Leu Arg Gly Val Pro Glu Lys Glu Val Gly
                1125                1130                1135

Lys Phe Gly Glu Trp Ala Ile Arg Lys Leu Gly Leu Val Lys Tyr Gly
                1140                1145                1150

Glu Lys Tyr Ala Ser Asn Tyr Ser Gly Gly Asn Lys Arg Lys Leu Ser
                1155                1160                1165

Thr Ala Met Ala Leu Ile Gly Gly Pro Pro Val Val Phe Leu Asp Glu
                1170                1175                1180

Pro Thr Thr Gly Met Asp Pro Lys Ala Arg Arg Phe Leu Trp Asn Cys
1185                1190                1195                1200

Ala Leu Ser Ile Val Lys Glu Gly Arg Ser Val Val Leu Thr Ser His
                1205                1210                1215

Ser Met Glu Glu Cys Glu Ala Leu Cys Thr Arg Met Ala Ile Met Val
                1220                1225                1230

Asn Gly Arg Phe Arg Cys Leu Gly Ser Val Gln His Leu Lys Asn Arg
                1235                1240                1245

Phe Gly Asp Gly Tyr Thr Ile Val Val Arg Ile Ala Gly Ser Asn Pro
                1250                1255                1260

Asp Leu Lys Pro Val Gln Glu Phe Phe Gly Leu Ala Phe Pro Gly Ser
1265                1270                1275                1280

Val Leu Lys Glu Lys His Arg Asn Met Leu Gln Tyr Gln Leu Pro Ser
                1285                1290                1295

Ser Leu Ser Ser Leu Ala Arg Ile Phe Ser Ile Leu Ser Gln Ser Lys
                1300                1305                1310

Lys Arg Leu His Ile Glu Asp Tyr Ser Val Ser Gln Thr Thr Leu Asp
                1315                1320                1325

Gln Val Phe Val Asn Phe Ala Lys Asp Gln Ser Asp Asp His Leu
                1330                1335                1340

Lys Asp Leu Ser Leu His Lys Asn Gln Thr Val Val Asp Val Ala Val
1345                1350                1355                1360

Leu Thr Ser Phe Leu Gln Asp Glu Lys Val Lys Glu Ser Tyr Val
                1365                1370                1375
```

(2) INFORMATION FOR SEQ ID NO:27:

(i) SEQUENCE CHARACTERISTICS:
        (A) LENGTH: 1457 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:27:

```
Met Glu Glu Glu Pro Thr His Leu Pro Leu Val Val Cys Val Asp Lys
1               5                   10                  15
```

-continued

```
Leu Thr Lys Val Tyr Lys Asn Asp Lys Leu Ala Leu Asn Lys Leu
             20                  25                  30

Ser Leu Asn Leu Tyr Glu Asn Gln Val Val Ser Phe Leu Gly His Asn
         35                  40                  45

Gly Ala Gly Lys Thr Thr Thr Met Ser Ile Leu Thr Gly Leu Phe Pro
     50                  55                  60

Pro Thr Ser Gly Ser Ala Thr Ile Tyr Gly His Asp Ile Arg Thr Glu
 65                  70                  75                  80

Met Asp Glu Ile Arg Lys Asn Leu Gly Met Cys Pro Gln His Asn Val
                 85                  90                  95

Leu Phe Asp Arg Leu Thr Val Glu Glu His Leu Trp Phe Tyr Ser Arg
            100                 105                 110

Leu Lys Ser Met Ala Gln Glu Glu Ile Arg Lys Glu Thr Asp Lys Met
        115                 120                 125

Ile Glu Asp Leu Glu Leu Ser Asn Lys Arg His Ser Leu Val Gln Thr
    130                 135                 140

Leu Ser Gly Gly Met Lys Arg Lys Leu Ser Val Ala Ile Ala Phe Val
145                 150                 155                 160

Gly Gly Ser Arg Ala Ile Ile Leu Asp Glu Pro Thr Ala Gly Val Asp
                165                 170                 175

Pro Tyr Ala Arg Arg Ala Ile Trp Asp Leu Ile Leu Lys Tyr Lys Pro
            180                 185                 190

Gly Arg Thr Ile Leu Leu Ser Thr His His Met Asp Glu Ala Asp Leu
        195                 200                 205

Leu Gly Asp Arg Ile Ala Ile Ile Ser His Gly Lys Leu Lys Cys Cys
    210                 215                 220

Gly Ser Pro Leu Phe Leu Lys Gly Ala Tyr Xaa Asp Gly Tyr Arg Leu
225                 230                 235                 240

Thr Leu Val Lys Gln Pro Ala Glu Pro Gly Thr Ser Gln Glu Pro Gly
                245                 250                 255

Leu Ala Ser Ser Pro Ser Gly Cys Pro Arg Leu Ser Ser Cys Ser Glu
            260                 265                 270

Pro Gln Val Ser Gln Phe Ile Arg Lys His Val Ala Ser Ser Leu Leu
        275                 280                 285

Val Ser Asp Thr Ser Thr Glu Leu Ser Tyr Ile Leu Pro Ser Glu Ala
    290                 295                 300

Val Lys Lys Gly Ala Phe Glu Arg Leu Phe Gln Gln Leu Glu His Ser
305                 310                 315                 320

Leu Asp Ala Leu His Leu Ser Ser Phe Gly Leu Met Asp Thr Thr Leu
                325                 330                 335

Glu Glu Val Phe Leu Lys Val Ser Glu Asp Gln Ser Leu Glu Asn
            340                 345                 350

Ser Glu Ala Asp Val Lys Glu Ser Arg Lys Asp Val Leu Pro Gly Ala
        355                 360                 365

Glu Gly Leu Thr Ala Val Gly Gln Ala Gly Asn Leu Ala Arg Cys
    370                 375                 380

Ser Glu Leu Ala Gln Ser Gln Ala Ser Leu Gln Ser Ala Ser Ser Val
385                 390                 395                 400

Gly Ser Ala Arg Gly Glu Glu Gly Thr Gly Tyr Ser Asp Gly Tyr Gly
                405                 410                 415

Asp Tyr Arg Pro Leu Phe Asp Asn Leu Gln Asp Pro Asp Asn Val Ser
            420                 425                 430

Leu Gln Glu Ala Glu Met Glu Ala Leu Ala Gln Val Gly Gln Gly Ser
```

```
                435                 440                 445
Arg Lys Leu Glu Gly Trp Trp Leu Lys Met Arg Gln Phe His Gly Leu
        450                 455                 460

Leu Val Lys Arg Phe His Cys Ala Arg Arg Asn Ser Lys Ala Leu Cys
465                 470                 475                 480

Ser Gln Ile Leu Leu Pro Ala Phe Phe Val Cys Val Ala Met Thr Val
                485                 490                 495

Ala Leu Ser Val Pro Glu Ile Gly Asp Leu Pro Pro Leu Val Leu Ser
        500                 505                 510

Pro Ser Gln Tyr His Asn Tyr Thr Gln Pro Arg Gly Asn Phe Ile Pro
        515                 520                 525

Tyr Ala Asn Glu Glu Arg Gln Glu Tyr Arg Leu Arg Leu Ser Pro Asp
530                 535                 540

Ala Ser Pro Gln Gln Leu Val Ser Thr Phe Arg Leu Pro Ser Gly Val
545                 550                 555                 560

Gly Ala Thr Cys Val Leu Lys Ser Pro Ala Asn Gly Ser Leu Gly Pro
                565                 570                 575

Met Leu Asn Leu Ser Ser Gly Glu Ser Arg Leu Leu Ala Ala Arg Phe
                580                 585                 590

Phe Asp Ser Met Cys Leu Glu Ser Phe Thr Gln Gly Leu Pro Leu Ser
                595                 600                 605

Asn Phe Val Pro Pro Pro Ser Pro Ala Pro Ser Asp Ser Pro Val
        610                 615                 620

Xaa Pro Asp Glu Asp Ser Leu Gln Ala Trp Asn Met Ser Leu Pro Pro
625                 630                 635                 640

Thr Ala Gly Pro Glu Thr Trp Thr Ser Ala Pro Ser Leu Pro Arg Leu
                645                 650                 655

Val His Glu Pro Val Arg Cys Thr Cys Ser Ala Gln Gly Thr Gly Phe
                660                 665                 670

Ser Cys Pro Ser Ser Val Gly Gly His Pro Pro Gln Met Arg Val Val
        675                 680                 685

Thr Gly Asp Ile Leu Thr Asp Ile Thr Gly His Asn Val Ser Glu Tyr
        690                 695                 700

Leu Leu Phe Thr Ser Asp Arg Phe Arg Leu His Arg Tyr Gly Ala Ile
705                 710                 715                 720

Thr Phe Gly Asn Val Gln Lys Ser Ile Pro Ala Ser Phe Gly Ala Arg
                725                 730                 735

Val Pro Pro Met Val Arg Lys Ile Ala Val Arg Arg Val Ala Gln Val
                740                 745                 750

Leu Tyr Asn Asn Lys Gly Tyr His Ser Met Pro Thr Tyr Leu Asn Ser
        755                 760                 765

Leu Asn Asn Ala Ile Leu Arg Ala Asn Leu Pro Lys Ser Lys Gly Asn
        770                 775                 780

Pro Ala Ala Tyr Xaa Ile Thr Val Thr Asn His Pro Met Asn Lys Thr
785                 790                 795                 800

Ser Ala Ser Leu Ser Leu Asp Tyr Leu Leu Gln Gly Thr Asp Val Val
                805                 810                 815

Ile Ala Ile Phe Ile Ile Val Ala Met Ser Phe Val Pro Ala Ser Phe
                820                 825                 830

Val Val Phe Leu Val Ala Glu Lys Ser Thr Lys Ala Lys His Leu Gln
                835                 840                 845

Phe Val Ser Gly Cys Asn Pro Val Ile Tyr Trp Leu Ala Asn Tyr Val
        850                 855                 860
```

-continued

```
Trp Asp Met Leu Asn Tyr Leu Val Pro Ala Thr Cys Cys Val Ile Ile
865                 870                 875                 880

Leu Phe Val Phe Asp Leu Pro Ala Tyr Thr Ser Pro Thr Asn Phe Pro
            885                 890                 895

Ala Val Leu Ser Leu Phe Leu Leu Tyr Gly Trp Ser Ile Thr Pro Ile
            900                 905                 910

Met Tyr Pro Ala Ser Phe Trp Phe Glu Val Pro Ser Ser Ala Tyr Val
            915                 920                 925

Phe Leu Ile Val Ile Asn Leu Phe Ile Gly Ile Thr Ala Thr Val Ala
            930                 935                 940

Thr Phe Leu Leu Gln Leu Phe Glu His Asp Lys Asp Leu Lys Val Val
945                 950                 955                 960

Asn Ser Tyr Leu Lys Ser Cys Phe Leu Ile Phe Pro Asn Tyr Asn Leu
                965                 970                 975

Gly His Gly Leu Met Glu Met Ala Tyr Asn Glu Tyr Ile Asn Glu Tyr
                980                 985                 990

Tyr Ala Lys Ile Gly Gln Phe Asp Lys Met Lys Ser Pro Phe Glu Trp
                995                 1000                1005

Asp Ile Val Thr Arg Gly Leu Val Ala Met Thr Val Glu Gly Phe Val
            1010                1015                1020

Gly Phe Phe Leu Thr Ile Met Cys Gln Tyr Asn Phe Leu Arg Gln Pro
1025                1030                1035                1040

Gln Arg Leu Pro Val Ser Thr Lys Pro Val Glu Asp Val Asp Val
                1045                1050                1055

Ala Ser Glu Arg Gln Arg Val Leu Arg Gly Asp Ala Asp Asn Asp Met
            1060                1065                1070

Val Lys Ile Glu Asn Leu Thr Lys Val Tyr Lys Ser Arg Lys Ile Gly
            1075                1080                1085

Arg Ile Leu Ala Val Asp Arg Leu Cys Leu Gly Val Cys Val Pro Gly
            1090                1095                1100

Glu Cys Phe Gly Leu Leu Gly Val Asn Gly Ala Gly Lys Thr Ser Thr
1105                1110                1115                1120

Phe Lys Met Leu Thr Gly Asp Glu Ser Thr Thr Gly Gly Glu Ala Phe
            1125                1130                1135

Val Asn Gly His Ser Val Leu Lys Asp Leu Leu Gln Val Gln Gln Ser
            1140                1145                1150

Leu Gly Tyr Cys Pro Gln Phe Asp Val Pro Val Asp Glu Leu Thr Ala
            1155                1160                1165

Arg Glu His Leu Gln Leu Tyr Thr Arg Leu Arg Cys Ile Pro Trp Lys
1170                1175                1180

Asp Glu Ala Gln Val Val Lys Trp Ala Leu Glu Lys Leu Glu Leu Thr
1185                1190                1195                1200

Lys Tyr Ala Asp Lys Pro Ala Gly Thr Tyr Ser Gly Gly Asn Lys Arg
            1205                1210                1215

Lys Leu Ser Thr Ala Ile Ala Leu Ile Gly Tyr Pro Ala Phe Ile Phe
            1220                1225                1230

Leu Asp Glu Pro Thr Thr Gly Met Asp Pro Lys Ala Arg Arg Phe Leu
            1235                1240                1245

Trp Asn Leu Ile Leu Asp Leu Ile Lys Thr Gly Arg Ser Val Val Leu
            1250                1255                1260

Thr Ser His Ser Met Glu Glu Cys Glu Ala Leu Cys Thr Arg Leu Ala
1265                1270                1275                1280
```

-continued

```
Ile Met Val Asn Gly Arg Leu His Cys Leu Gly Ser Ile Gln His Leu
            1285                1290                1295

Lys Asn Arg Phe Gly Asp Gly Tyr Met Ile Thr Val Arg Thr Lys Ser
        1300                1305                1310

Ser Gln Asn Val Lys Asp Val Arg Phe Phe Asn Arg Asn Phe Pro
        1315                1320            1325

Glu Ala His Ala Gln Gly Lys Thr Pro Tyr Lys Val Gln Tyr Gln Leu
    1330                1335                1340

Lys Ser Glu His Ile Ser Leu Ala Gln Val Phe Ser Lys Met Glu Gln
1345                1350                1355                1360

Val Val Gly Val Leu Gly Ile Glu Asp Tyr Ser Val Ser Gln Thr Thr
                1365                1370                1375

Leu Asp Asn Val Phe Val Asn Phe Ala Lys Lys Gln Ser Asp Asn Val
                1380                1385                1390

Glu Gln Gln Glu Ala Glu Pro Ser Ser Leu Pro Ser Pro Leu Gly Leu
            1395                1400                1405

Leu Ser Leu Leu Arg Pro Arg Pro Ala Pro Thr Glu Leu Arg Ala Leu
        1410                1415                1420

Val Ala Asp Glu Pro Glu Asp Leu Asp Thr Glu Asp Glu Gly Leu Ile
1425                1430                1435                1440

Ser Phe Glu Glu Glu Arg Ala Gln Leu Ser Phe Asn Thr Asp Thr Leu
            1445                1450                1455

Cys
```

(2) INFORMATION FOR SEQ ID NO:28:

(i) SEQUENCE CHARACTERISTICS:
        (A) LENGTH: 1548 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 49..1271

(xi) SEQUENCE DESCRIPTION: SEQ ID NO:28:

```
GGCGGCTAGC GGCGAGGCCC CTTCCTGTAC CTTCAGGGAT CGGCCACC ATG TCC CAC        57
                                                    Met Ser His
                                                      1

CGG AAG TTT TCC GCC CCT CGG CAC GGA CAC CTG GGC TTC CTG CCC CAT       105
Arg Lys Phe Ser Ala Pro Arg His Gly His Leu Gly Phe Leu Pro His
        5                   10                  15

AAG AGG AGC CAC CGG CAC CGG GGC AAG GTG AAG ACG TGG CCG CGG GAT       153
Lys Arg Ser His Arg His Arg Gly Lys Val Lys Thr Trp Pro Arg Asp
 20                  25                  30                  35

GAC CCC AGC CAG CCC GTG CAC CTC ACG GCC TTC CTG GGC TAC AAG GCG       201
Asp Pro Ser Gln Pro Val His Leu Thr Ala Phe Leu Gly Tyr Lys Ala
                40                  45                  50

GGC ATG ACC CAC ACC CTG CGG GAG GTG CAC CGG CCG GGG CTC AAA ATT       249
Gly Met Thr His Thr Leu Arg Glu Val His Arg Pro Gly Leu Lys Ile
            55                  60                  65

TCC AAA CGG GAG GAG GTG GAG GCG GTG ACA ATT GTA GAA ACG CCG CCC       297
Ser Lys Arg Glu Glu Val Glu Ala Val Thr Ile Val Glu Thr Pro Pro
        70                  75                  80

CTA GTG GTG GTG GGC GTG GTG GGC TAC GTG GCC ACC CCT CGA GGT CTC       345
Leu Val Val Val Gly Val Val Gly Tyr Val Ala Thr Pro Arg Gly Leu
    85                  90                  95
```

```
CGG AGC TTC AAG ACC ATC TTT GCA GAA CAC CTC AGT GAT GAG TGC CGG      393
Arg Ser Phe Lys Thr Ile Phe Ala Glu His Leu Ser Asp Glu Cys Arg
100             105                 110                 115

CGC CGA TTC TAC AAG GAC TGG CAC AAG AGC AAG AAG AAA GCC TTC ACC      441
Arg Arg Phe Tyr Lys Asp Trp His Lys Ser Lys Lys Lys Ala Phe Thr
                120                 125                 130

AAG GCC TGC AAG AGG TGG CGG GAC ACA GAC GGG AAA AAG CAG CTA CAG      489
Lys Ala Cys Lys Arg Trp Arg Asp Thr Asp Gly Lys Lys Gln Leu Gln
            135                 140                 145

AAG GAC TTC GCC GCC ATG AAG AAG TAC TGC AAG GTC ATT CGG GTC ATT      537
Lys Asp Phe Ala Ala Met Lys Lys Tyr Cys Lys Val Ile Arg Val Ile
        150                 155                 160

GTC CAC ACT CAG ATG AAA CTG CTG CCC TTC CGG CAG AAG AAG GCC CAC      585
Val His Thr Gln Met Lys Leu Leu Pro Phe Arg Gln Lys Lys Ala His
    165                 170                 175

ATC ATG GAG ATC CAG CTG AAC GGT GGC ACG GTG GCC GAG AAG GTG GCC      633
Ile Met Glu Ile Gln Leu Asn Gly Gly Thr Val Ala Glu Lys Val Ala
180                 185                 190                 195

TGG GCC CAG GCC CGG CTG GAG AAG CAG GTG CCC GTG CAC AGC GTG TTC      681
Trp Ala Gln Ala Arg Leu Glu Lys Gln Val Pro Val His Ser Val Phe
                200                 205                 210

AGC CAG AGT GAG GTC ATT GAT GTC ATT GCT GTC ACC AAG GGT CGA GGC      729
Ser Gln Ser Glu Val Ile Asp Val Ile Ala Val Thr Lys Gly Arg Gly
            215                 220                 225

GTC AAA GGG GTC ACA AGC CGC TGG CAT ACC AAG AAG CTG CCG CGC AAG      777
Val Lys Gly Val Thr Ser Arg Trp His Thr Lys Lys Leu Pro Arg Lys
        230                 235                 240

ACC CAT AAG GGC CTG CGC AAG GTG GCC TGC ATT GGC GCC TGG CAC CCC      825
Thr His Lys Gly Leu Arg Lys Val Ala Cys Ile Gly Ala Trp His Pro
    245                 250                 255

GCC CGC GTG GGC TGC TCC ATT GCT CGG GCC GGG CAG AAG GGC TAT CAC      873
Ala Arg Val Gly Cys Ser Ile Ala Arg Ala Gly Gln Lys Gly Tyr His
260                 265                 270                 275

CAC CGC ACG GAG CTC AAC AAG AAG ATC TTC CGC ATC GGC AGG GGC CCG      921
His Arg Thr Glu Leu Asn Lys Lys Ile Phe Arg Ile Gly Arg Gly Pro
                280                 285                 290

CAC ATG GAG GAC GGG AAG CTG GTG AAG AAC AAT GCA TCC ACC AGC TAC      969
His Met Glu Asp Gly Lys Leu Val Lys Asn Asn Ala Ser Thr Ser Tyr
            295                 300                 305

GAC GTG ACT GCC AAG TCC ATC ACA CCG CTG GGT GGC TTC CCC CAC TAC     1017
Asp Val Thr Ala Lys Ser Ile Thr Pro Leu Gly Gly Phe Pro His Tyr
        310                 315                 320

GGG GAA GTG AAC AAC GAC TTC GTC ATG CTG AAG GGT TGT ATT GCT GGT     1065
Gly Glu Val Asn Asn Asp Phe Val Met Leu Lys Gly Cys Ile Ala Gly
    325                 330                 335

ACC AAG AAG CGG GTC ATT ACG CTG AGA AAG TCC CTC CTG GTG CAT CAC     1113
Thr Lys Lys Arg Val Ile Thr Leu Arg Lys Ser Leu Leu Val His His
340                 345                 350                 355

AGT CGC CAA GCC GTG GAG AAT ATT GAG CTC AAG TTC ATT GAC ACC ACC     1161
Ser Arg Gln Ala Val Glu Asn Ile Glu Leu Lys Phe Ile Asp Thr Thr
                360                 365                 370

TCC AAG TTC GGC CAT GGC CGC TTC CAG ACA GCC CAA GAG AAG AGG GCC     1209
Ser Lys Phe Gly His Gly Arg Phe Gln Thr Ala Gln Glu Lys Arg Ala
            375                 380                 385

TTC ATG GGC CCC CAA AAG AAG CAT CTG GAG AAG GAA ACG CCG GAG ACC     1257
Phe Met Gly Pro Gln Lys Lys His Leu Glu Lys Glu Thr Pro Glu Thr
        390                 395                 400

TCG GGA GAC TTG TA GGCTGTGTGG GGTGGATGAA CCCTGAAGCG CACCGCACTG     1311
Ser Gly Asp Leu
```

-continued

```
                    405

TCTGCCCCAA TGTCTAACAA AGGCCGGAGG CGACTCTTCC TGCGAGGTCT CAGAGCGCTG    1371

TGTAACCGCC CAAGGGGTTC ACCTTGCCTG CTGCCTAGAC AAAGCCGATT CATTAAGACA    1431

GGGGAATTGC AATAGAGAAA GAGTAATTCA CACAGAGCTG GCTGTGCGGG AGACCGGAGT    1491

TTTATGTTTT ATTATTACTC AAATCGATCT CTTTGAGCAA AAAAAAAAAA AAAAAAA      1548

(2) INFORMATION FOR SEQ ID NO:29:

(i) SEQUENCE CHARACTERISTICS:
        (A) LENGTH: 407 amino acids
        (B) TYPE: amino acid
        (D) TOPOLOGY: linear (ii) MOLECULE TYPE: protein (xi) SEQUENCE DESCRIPTION: SEQ ID NO:29:

Met Ser His Arg Lys Phe Ser Ala Pro Arg His Gly His Leu Gly Phe
 1               5                  10                  15

Leu Pro His Lys Arg Ser His Arg His Arg Gly Lys Val Lys Thr Trp
                20                  25                  30

Pro Arg Asp Asp Pro Ser Gln Pro Val His Leu Thr Ala Phe Leu Gly
            35                  40                  45

Tyr Lys Ala Gly Met Thr His Thr Leu Arg Glu Val His Arg Pro Gly
        50                  55                  60

Leu Lys Ile Ser Lys Arg Glu Val Glu Ala Val Thr Ile Val Glu
 65                  70                  75                  80

Thr Pro Pro Leu Val Val Val Gly Val Val Gly Tyr Val Ala Thr Pro
                85                  90                  95

Arg Gly Leu Arg Ser Phe Lys Thr Ile Phe Ala Glu His Leu Ser Asp
                100                 105                 110

Glu Cys Arg Arg Arg Phe Tyr Lys Asp Trp His Lys Ser Lys Lys Lys
            115                 120                 125

Ala Phe Thr Lys Ala Cys Lys Arg Trp Arg Asp Thr Asp Gly Lys Lys
130                 135                 140

Gln Leu Gln Lys Asp Phe Ala Ala Met Lys Lys Tyr Cys Lys Val Ile
145                 150                 155                 160

Arg Val Ile Val His Thr Gln Met Lys Leu Leu Pro Phe Arg Gln Lys
                165                 170                 175

Lys Ala His Ile Met Glu Ile Gln Leu Asn Gly Gly Thr Val Ala Glu
                180                 185                 190

Lys Val Ala Trp Ala Gln Ala Arg Leu Glu Lys Gln Val Pro Val His
                195                 200                 205

Ser Val Phe Ser Gln Ser Glu Val Ile Asp Val Ile Ala Val Thr Lys
            210                 215                 220

Gly Arg Gly Val Lys Gly Val Thr Ser Arg Trp His Thr Lys Lys Leu
225                 230                 235                 240

Pro Arg Lys Thr His Lys Gly Leu Arg Lys Val Ala Cys Ile Gly Ala
                245                 250                 255

Trp His Pro Ala Arg Val Gly Cys Ser Ile Ala Arg Ala Gly Gln Lys
                260                 265                 270

Gly Tyr His His Arg Thr Glu Leu Asn Lys Lys Ile Phe Arg Ile Gly
            275                 280                 285

Arg Gly Pro His Met Glu Asp Gly Lys Leu Val Lys Asn Asn Ala Ser
290                 295                 300
```

```
Thr Ser Tyr Asp Val Thr Ala Lys Ser Ile Thr Pro Leu Gly Gly Phe
305                 310                 315                 320

Pro His Tyr Gly Glu Val Asn Asn Asp Phe Val Met Leu Lys Gly Cys
            325                 330                 335

Ile Ala Gly Thr Lys Lys Arg Val Ile Thr Leu Arg Lys Ser Leu Leu
            340                 345                 350

Val His His Ser Arg Gln Ala Val Glu Asn Ile Glu Leu Lys Phe Ile
            355                 360                 365

Asp Thr Thr Ser Lys Phe Gly His Gly Arg Phe Gln Thr Ala Gln Glu
    370                 375                 380

Lys Arg Ala Phe Met Gly Pro Gln Lys Lys His Leu Glu Lys Glu Thr
385                 390                 395                 400

Pro Glu Thr Ser Gly Asp Leu
                405
```

(2) INFORMATION FOR SEQ ID NO:30:

(i) SEQUENCE CHARACTERISTICS:
        (A) LENGTH: 403 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:30:

```
Met Ser His Arg Lys Phe Ser Ala Pro Arg His Gly Ser Leu Gly Phe
1               5                   10                  15

Leu Pro Arg Lys Arg Ser Ser Arg His Arg Gly Lys Val Lys Ser Phe
            20                  25                  30

Pro Lys Asp Asp Pro Ser Lys Pro Val His Leu Thr Ala Phe Leu Gly
            35                  40                  45

Tyr Lys Ala Gly Met Thr His Ile Val Arg Glu Val Asp Arg Pro Gly
    50                  55                  60

Ser Lys Val Asn Lys Lys Glu Val Val Glu Ala Val Thr Ile Val Glu
65                  70                  75                  80

Thr Pro Pro Met Val Val Gly Ile Val Gly Tyr Val Glu Thr Pro
                85                  90                  95

Arg Gly Leu Arg Thr Phe Lys Thr Val Phe Ala Glu His Ile Ser Asp
            100                 105                 110

Glu Cys Lys Arg Arg Phe Tyr Lys Asn Trp His Lys Ser Lys Lys Lys
            115                 120                 125

Ala Phe Thr Lys Tyr Cys Lys Lys Trp Gln Asp Glu Asp Gly Lys Lys
130                 135                 140

Gln Leu Glu Lys Asp Phe Ser Ser Met Lys Lys Tyr Cys Gln Val Ile
145                 150                 155                 160

Arg Val Ile Ala His Thr Gln Met Arg Leu Leu Pro Leu Arg Gln Lys
            165                 170                 175

Lys Ala His Leu Met Glu Ile Gln Val Asn Gly Gly Thr Val Ala Glu
            180                 185                 190

Lys Leu Asp Trp Ala Arg Glu Arg Leu Glu Gln Gln Val Pro Val Asn
            195                 200                 205

Gln Val Phe Gly Gln Asp Glu Met Ile Asp Val Ile Gly Val Thr Lys
            210                 215                 220

Gly Lys Gly Tyr Lys Gly Val Thr Ser Arg Trp His Thr Lys Lys Leu
225                 230                 235                 240
```

```
Pro Arg Lys Thr His Arg Gly Leu Arg Lys Val Ala Cys Ile Gly Ala
            245                 250                 255

Trp His Pro Ala Arg Val Ala Phe Ser Val Ala Arg Ala Gly Gln Lys
            260                 265                 270

Gly Tyr His His Arg Thr Glu Ile Asn Lys Lys Ile Tyr Lys Ile Gly
            275                 280                 285

Gln Gly Tyr Leu Ile Lys Asp Gly Lys Leu Ile Lys Asn Asn Ala Ser
        290                 295                 300

Thr Asp Tyr Asp Leu Ser Asp Lys Ser Ile Asn Pro Leu Gly Gly Phe
305                 310                 315                 320

Val His Tyr Gly Glu Val Thr Asn Asp Phe Val Met Leu Lys Gly Cys
            325                 330                 335

Val Val Gly Thr Lys Lys Arg Val Leu Thr Leu Arg Lys Ser Leu Leu
            340                 345                 350

Val Gln Thr Lys Arg Arg Ala Leu Glu Lys Ile Asp Leu Lys Phe Ile
            355                 360                 365

Asp Thr Thr Ser Lys Phe Gly His Gly Arg Phe Gln Thr Met Glu Glu
370                 375                 380

Lys Lys Ala Phe Met Gly Pro Leu Lys Lys Asp Arg Ile Ala Lys Glu
385                 390                 395                 400

Glu Gly Ala (2) INFORMATION FOR SEQ ID NO:31:

(i) SEQUENCE CHARACTERISTICS:
        (A) LENGTH: 403 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:31:

Met Ser His Arg Lys Phe Ser Ala Pro Arg His Gly Ser Leu Gly Phe
1               5                   10                  15

Leu Pro Arg Lys Arg Ser Arg His Arg Gly Lys Val Lys Ser Phe
                20                  25                  30

Pro Lys Asp Asp Ser Ser Lys Pro Val His Leu Thr Ala Phe Leu Gly
            35                  40                  45

Tyr Lys Ala Gly Met Thr His Ile Val Arg Glu Val Asp Arg Pro Gly
50                  55                  60

Ser Lys Val Asn Lys Lys Glu Val Val Glu Ala Val Thr Ile Val Glu
65                  70                  75                  80

Thr Pro Pro Met Val Ile Val Gly Ile Val Gly Tyr Val Glu Thr Pro
            85                  90                  95

Arg Gly Leu Arg Thr Phe Lys Thr Ile Phe Ala Glu His Ile Ser Asp
            100                 105                 110

Glu Cys Lys Arg Arg Phe Tyr Lys Asn Trp His Lys Ser Lys Lys Lys
            115                 120                 125

Ala Phe Thr Lys Tyr Cys Lys Lys Trp Gln Asp Ala Asp Gly Lys Lys
            130                 135                 140

Gln Leu Glu Arg Asp Phe Ser Ser Met Lys Lys Tyr Cys Gln Val Ile
145                 150                 155                 160

Arg Val Ile Ala His Thr Gln Met Arg Leu Leu Pro Leu Arg Gln Lys
            165                 170                 175

Lys Ala His Leu Met Glu Val Gln Val Asn Gly Gly Thr Val Ala Glu
```

-continued

```
                180                 185                 190
Lys Leu Asp Trp Ala Arg Glu Arg Leu Glu Gln Gln Val Pro Val Asn
            195                 200                 205

Gln Val Phe Gly Gln Asp Glu Met Ile Asp Val Ile Gly Val Thr Lys
        210                 215                 220

Gly Lys Gly Tyr Lys Gly Val Thr Ser Arg Trp His Thr Lys Leu
225                 230                 235                 240

Pro Arg Lys Thr His Arg Gly Leu Arg Lys Val Ala Cys Ile Gly Ala
                245                 250                 255

Trp His Pro Ala Arg Val Ala Phe Ser Val Ala Arg Ala Gly Gln Lys
            260                 265                 270

Gly Tyr His His Arg Thr Glu Ile Asn Lys Lys Ile Tyr Lys Ile Gly
        275                 280                 285

Gln Gly Tyr Leu Ile Lys Asp Gly Lys Leu Ile Lys Asn Asn Ala Ser
    290                 295                 300

Thr Asp Tyr Asp Leu Ser Asp Lys Ser Ile Asn Pro Leu Gly Gly Phe
305                 310                 315                 320

Val His Tyr Gly Glu Val Thr Asn Asp Phe Val Met Leu Lys Gly Cys
                325                 330                 335

Val Val Gly Thr Lys Lys Arg Val Leu Thr Leu Arg Lys Ser Leu Leu
            340                 345                 350

Val Gln Thr Lys Arg Arg Ala Leu Glu Lys Ile Asp Leu Lys Phe Ile
        355                 360                 365

Asp Thr Thr Ser Lys Phe Gly His Gly Arg Phe Gln Thr Val Glu Glu
    370                 375                 380

Lys Lys Ala Phe Met Gly Pro Leu Lys Lys Asp Arg Ile Ala Lys Glu
385                 390                 395                 400

Glu Gly Ala
```

(2) INFORMATION FOR SEQ ID NO:32:

(i) SEQUENCE CHARACTERISTICS:
        (A) LENGTH: 403 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:32:

```
Met Ser His Arg Lys Phe Ser Ala Pro Arg His Gly Ser Leu Gly Phe
1               5                   10                  15

Leu Pro Arg Lys Arg Ser Ser Arg His Arg Gly Lys Val Lys Ser Phe
            20                  25                  30

Pro Lys Asp Asp Ala Ser Lys Pro Val His Leu Thr Ala Phe Leu Gly
        35                  40                  45

Tyr Lys Ala Gly Met Thr His Ile Val Arg Glu Val Asp Arg Pro Gly
    50                  55                  60

Ser Lys Val Asn Lys Lys Glu Val Val Glu Ala Val Thr Ile Val Glu
65              70                  75                  80

Thr Pro Pro Met Val Val Gly Ile Val Gly Tyr Val Glu Thr Pro
                85                  90                  95

Arg Gly Leu Arg Thr Phe Lys Thr Val Phe Ala Glu His Ile Ser Asp
            100                 105                 110

Glu Cys Lys Arg Arg Phe Tyr Lys Asn Trp His Lys Ser Lys Lys Lys
        115                 120                 125
```

```
Ala Phe Thr Lys Tyr Cys Lys Lys Trp Gln Asp Thr Gly Lys Lys
    130                 135                 140

Gln Leu Glu Lys Asp Phe Asn Ser Met Lys Lys Tyr Cys Gln Val Ile
145                 150                 155                 160

Arg Ile Ile Ala His Thr Gln Met Arg Leu Leu Pro Leu Arg Gln Lys
                    165                 170                 175

Lys Ala His Leu Met Glu Ile Gln Val Asn Gly Gly Thr Val Ala Glu
                180                 185                 190

Lys Leu Asp Trp Ala Arg Glu Arg Leu Glu Gln Val Pro Val Ser
    195                 200                 205

Gln Val Phe Gly Gln Asp Glu Met Ile Asp Val Ile Gly Val Thr Lys
    210                 215                 220

Gly Lys Gly Tyr Lys Gly Val Thr Ser Arg Trp His Thr Lys Lys Leu
225                 230                 235                 240

Pro Arg Lys Thr His Arg Gly Leu Arg Lys Val Ala Cys Ile Gly Ala
                245                 250                 255

Trp His Pro Ala Arg Val Ala Phe Thr Val Ala Arg Ala Gly Gln Lys
                260                 265                 270

Gly Tyr His His Arg Thr Glu Ile Asn Lys Lys Ile Tyr Lys Ile Gly
                275                 280                 285

Gln Gly Tyr Leu Ile Lys Asp Gly Lys Leu Ile Lys Asn Asn Ala Ser
    290                 295                 300

Thr Asp Tyr Asp Leu Ser Asp Lys Ser Ile Asn Pro Leu Gly Gly Phe
305                 310                 315                 320

Val His Tyr Gly Glu Val Thr Asn Asp Phe Ile Met Leu Lys Gly Cys
                325                 330                 335

Val Val Gly Thr Lys Lys Arg Val Leu Thr Leu Arg Lys Ser Leu Leu
                340                 345                 350

Val Gln Thr Lys Arg Arg Ala Leu Glu Lys Ile Asp Leu Lys Phe Ile
                355                 360                 365

Asp Thr Thr Ser Lys Phe Gly His Gly Arg Phe Gln Thr Met Glu Glu
                370                 375                 380

Lys Lys Ala Phe Met Gly Pro Leu Lys Lys Asp Arg Ile Ala Lys Glu
385                 390                 395                 400

Glu Gly Ala (2) INFORMATION FOR SEQ ID NO:33:

(i) SEQUENCE CHARACTERISTICS:
        (A) LENGTH: 468 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..357

(xi) SEQUENCE DESCRIPTION: SEQ ID NO:33:

CGG GAC ACC AAG TTT AGG GAG GAC TGC CCG CCG GAT CGC GAG GAA CTG      48
Arg Asp Thr Lys Phe Arg Glu Asp Cys Pro Pro Asp Arg Glu Glu Leu
  1               5                  10                  15

GGC CGC CAC AGC TGG GCT GTC CTC CAC ACC CTG GCC GCC TAC TAC CCC      96
Gly Arg His Ser Trp Ala Val Leu His Thr Leu Ala Ala Tyr Tyr Pro
             20                  25                  30
```

```
GAC CTG CCC ACC CCA GAA CAG CAG CAA GAC ATG GCC CAG TTC ATA CAT        144
Asp Leu Pro Thr Pro Glu Gln Gln Gln Asp Met Ala Gln Phe Ile His
        35                  40                  45

TTA TTT TCT AAG TTT TAC CCC TGT GAG GAG TGT GCT GAA GAC CTA AGA        192
Leu Phe Ser Lys Phe Tyr Pro Cys Glu Glu Cys Ala Glu Asp Leu Arg
    50                  55                  60

AAA AGG CTG TGC AGG AAC CAC CCA GAC ACC CGC ACC CGG GCA TGC TTC        240
Lys Arg Leu Cys Arg Asn His Pro Asp Thr Arg Thr Arg Ala Cys Phe
65                  70                  75                  80

ACA CAG TGG CTG TGC CAC CTG CAC AAT GAA GTG AAC CGC AAG CTG GGC        288
Thr Gln Trp Leu Cys His Leu His Asn Glu Val Asn Arg Lys Leu Gly
                85                  90                  95

AAG CCT GAC TTC GAC TGC TCA AAA GTG GAT GAG CGC TGG CGC GAC GGC        336
Lys Pro Asp Phe Asp Cys Ser Lys Val Asp Glu Arg Trp Arg Asp Gly
            100                 105                 110

TGG AAG GAT GGC TCC TGT GAC TAGAGGGTGG TCAGCCAGAG CTCATGGGAC           387
Trp Lys Asp Gly Ser Cys Asp
        115

AGCTAGCCAG GCATGGTTGG ATAGGGGCAG GGCACTCATT AAAGTGCATC ACAGCCAGAA      447

AAAAAAAAAA AAAAAAAAA A                                                 468

(2) INFORMATION FOR SEQ ID NO:34:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:34:

Arg Asp Thr Lys Phe Arg Glu Asp Cys Pro Pro Asp Arg Glu Glu Leu
1               5                   10                  15

Gly Arg His Ser Trp Ala Val Leu His Thr Leu Ala Ala Tyr Tyr Pro
            20                  25                  30

Asp Leu Pro Thr Pro Glu Gln Gln Gln Asp Met Ala Gln Phe Ile His
        35                  40                  45

Leu Phe Ser Lys Phe Tyr Pro Cys Glu Glu Cys Ala Glu Asp Leu Arg
    50                  55                  60

Lys Arg Leu Cys Arg Asn His Pro Asp Thr Arg Thr Arg Ala Cys Phe
65                  70                  75                  80

Thr Gln Trp Leu Cys His Leu His Asn Glu Val Asn Arg Lys Leu Gly
                85                  90                  95

Lys Pro Asp Phe Asp Cys Ser Lys Val Asp Glu Arg Trp Arg Asp Gly
            100                 105                 110

Trp Lys Asp Gly Ser Cys Asp
        115

(2) INFORMATION FOR SEQ ID NO:35:

(i) SEQUENCE CHARACTERISTICS:
        (A) LENGTH: 125 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:35:

Met Arg Thr Gln Gln Lys Arg Asp Ile Lys Phe Arg Glu Asp Cys Pro
1               5                   10                  15
```

```
Gln Asp Arg Glu Glu Leu Gly Arg Asn Thr Trp Ala Phe Leu His Thr
             20                  25                  30

Leu Ala Ala Tyr Tyr Pro Asp Met Pro Thr Pro Glu Gln Gln Gln Asp
         35                  40                  45

Met Ala Gln Phe Ile His Ile Phe Ser Lys Phe Tyr Pro Cys Glu Glu
     50                  55                  60

Cys Ala Glu Asp Ile Arg Lys Arg Ile Asp Arg Ser Gln Pro Asp Thr
 65                  70                  75                  80

Ser Thr Arg Val Ser Phe Ser Gln Trp Leu Cys Arg Leu His Asn Glu
                 85                  90                  95

Val Asn Arg Lys Leu Gly Lys Pro Asp Phe Asp Cys Ser Arg Val Asp
             100                 105                 110

Glu Arg Trp Arg Asp Gly Trp Lys Asp Gly Ser Cys Asp
             115                 120                 125
```

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:36:

TGACGCCGTG CCCATCCAGT                                          20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:37:

CAGCGTGGTG TTATGTTCCT                                          20

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:38:

TTGGGCCTGT GCTGAACTAC                                          20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:39:

CGGCAAGCTG GTGATTAACA                                                    20

(2) INFORMATION FOR SEQ ID NO:40:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:40:

CGGCAGAGGA TGCTGTGT                                                      18

(2) INFORMATION FOR SEQ ID NO:41:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:41:

GCGGAGCCAC CTTCATCA                                                      18

(2) INFORMATION FOR SEQ ID NO:42:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:42:

GACGCTGGTG AAGGAGC                                                       17

(2) INFORMATION FOR SEQ ID NO:43:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:43:

TCGCTGACCG CCAGGAT                                                       17

(2) INFORMATION FOR SEQ ID NO:44:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:44:

CTGTCGGGAA GGTCTCACTG                                                  20

(2) INFORMATION FOR SEQ ID NO:45:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:45:

GTTCACCGCC TTGGAGGATT                                                  20

(2) INFORMATION FOR SEQ ID NO:46:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:46:

GTGTGGGGAA GACCTGTCTG                                                  20

(2) INFORMATION FOR SEQ ID NO:47:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:47:

AGGAGGCCTT GTTGGTGACA                                                  20

(2) INFORMATION FOR SEQ ID NO:48:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:48:

ACGGACACCT GGGCTTC                                                     17

(2) INFORMATION FOR SEQ ID NO:49:

(i) SEQUENCE CHARACTERISTICS:
            (A) LENGTH: 17 base pairs
            (B) TYPE: nucleic acid
            (C) STRANDEDNESS: single (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:49:

AAACGGGAGG AGGTGGA                                                          17

(2) INFORMATION FOR SEQ ID NO:50:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:50:

TGTGGCTATG AGCTGTTCTC                                                       20

(2) INFORMATION FOR SEQ ID NO:51:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide  primer"

(xi) SEQUENCE DESCRIPTION: SEQ ID NO:51:

GCAGTCCCGA TTCTGAATAT                                                       20

(2) INFORMATION FOR SEQ ID NO:52:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:52:

CATTGCCCGT GCTGTCGTG                                                        19

(2) INFORMATION FOR SEQ ID NO:53:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer"

(xi) SEQUENCE DESCRIPTION: SEQ ID NO:53:

CATCGCCGCC TCCTTCATG                                                        19

(2) INFORMATION FOR SEQ ID NO:54:

(i) SEQUENCE CHARACTERISTICS:
            (A) LENGTH: 18 base pairs
            (B) TYPE: nucleic acid

```
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:54:

GCGGAGCCAC CTTCATCA                                                 18

(2) INFORMATION FOR SEQ ID NO:55:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:55:

GACGCTGGTG AAGGAGC                                                  17

(2) INFORMATION FOR SEQ ID NO:56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:56:

ATCCTGGCGG TCAGCGA                                                  17

(2) INFORMATION FOR SEQ ID NO:57:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:57:

AGGGATTCGA CATTGCC                                                  17

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:58:

CTTCAGAGAC TCAGGGGCAT                                               20

(2) INFORMATION FOR SEQ ID NO:59:

(i) SEQUENCE CHARACTERISTICS:
        (A) LENGTH: 17 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:59:

GCCTGTCATC GCTCTAG                                                17

(2) INFORMATION FOR SEQ ID NO:60:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:60:

CAGTCGCAGG CCCTGCA                                                17

(2) INFORMATION FOR SEQ ID NO:61:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:61:

GAGGACGCGC CAACATC                                                17

(2) INFORMATION FOR SEQ ID NO:62:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:62:

CGGCAGTAGT GGCAGTG                                                17

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:63:

CCTGCCTCGC TTGCTCCTGC                                             20

(2) INFORMATION FOR SEQ ID NO:64:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:64:

CGGGCAGCCG CAGGCCGCAT                                           20

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:65:

CCTGCAACGG CCATGCCCGC                                           20

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:66:

GCATCCCCGG CGGGCACCCA                                           20

(2) INFORMATION FOR SEQ ID NO:67:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:67:

GTTCGTACGA GAATCGCT                                             18

(2) INFORMATION FOR SEQ ID NO:68:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Kozak Initiation Sequence"

(xi) SEQUENCE DESCRIPTION: SEQ ID NO:68:

CCACCATGT                                                        9

(2) INFORMATION FOR SEQ ID NO:69:
```

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:69:

TGGCCCAGTT CATACATTTA                                               20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:70:

TTACCCCTGT GAGGAGTGTG                                               20

(2) INFORMATION FOR SEQ ID NO:71:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:71:

His Arg Asp Leu Lys Pro Glu Asn
1               5

(2) INFORMATION FOR SEQ ID NO:72:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:72:

GTCCTTCTTG CAGAACT                                                  17

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO:73:

AGACAGCCCA AGAGAAGAGG                                               20
```

What is claimed is:

1. An isolated human netrin (hNET) polypeptide comprising the amino acid sequence set forth in SEQ ID NO:21 or a polypeptide having conservative amino acid substitutions of SEQ ID NO:21.

2. The isolated human netrin (hNET) polypeptide of claim 1, wherein the polypeptide comprises the sequence set forth in SEQ ID NO:21.

3. A composition comprising the isolated human netrin polypeptide of any of claims 1 to 2, and a carrier.

4. The composition of claim 3, wherein the carrier is a pharmaceutically acceptable carrier.

5. An isolated human netrin polypeptide, produced by the method comprising:

a) introducing into a host cell a nucleic acid encoding a polypeptide of any of claims 1 to 2, growing the cell under conditions suitable for transcription and translation of the nucleic acid, thereby producing the netrin polypeptide; and b) isolating the polypeptide so produced.

6. A human netrin polypeptide of claim 5, wherein the nucleic acid further comprises nucleotide sequences that encode additional amino-terminal or carboxy-terminal amino acids which function as tags for immunopurity purification.

* * * * *